US008093362B2

(12) United States Patent
Ochiai et al.

(10) Patent No.: US 8,093,362 B2
(45) Date of Patent: *Jan. 10, 2012

(54) ANTI-PERP RECOMBINANT ANTIBODY

(75) Inventors: Atsushi Ochiai, Kashiwa (JP); Emi Hosaka, Stuttgart (DE); Kazuyasu Nakamura, Machida (JP); Akiko Furuya, Machida (JP); Yuji Ohki, Machida (JP)

(73) Assignees: Kyowa Hakko Kirin Co., Ltd., Tokyo (JP); Japan as Represented by President of National Cancer Center, Tokyo (JP)

( * ) Notice: Subject to any disclaimer, the term of this patent is extended or adjusted under 35 U.S.C. 154(b) by 588 days.

This patent is subject to a terminal disclaimer.

(21) Appl. No.: 11/634,209

(22) Filed: Dec. 6, 2006

(65) Prior Publication Data
US 2008/0267953 A1 Oct. 30, 2008

(30) Foreign Application Priority Data

Dec. 6, 2005 (JP) ............................. P. 2005-352297

(51) Int. Cl.
*C07K 16/00* (2006.01)
*C12P 21/08* (2006.01)
*C12P 21/04* (2006.01)
*A61K 39/395* (2006.01)
*A61K 39/00* (2006.01)

(52) U.S. Cl. ............... 530/387.9; 530/387.1; 530/387.3; 530/388.1; 424/130.1; 424/133.1; 424/139.1; 424/141.1; 435/69.6

(58) Field of Classification Search .................. None
See application file for complete search history.

(56) References Cited

U.S. PATENT DOCUMENTS

| 5,714,350 A | 2/1998 | Co et al. | |
|---|---|---|---|
| 2006/0286090 A1* | 12/2006 | Attardi et al. | 424/131.1 |
| 2009/0169547 A1* | 7/2009 | Sahin et al. | 424/133.1 |

FOREIGN PATENT DOCUMENTS

| WO | 01/10883 A1 | 2/2001 |
|---|---|---|
| WO | 01/90353 A1 | 11/2001 |
| WO | 02/060317 A2 | 8/2002 |
| WO | 03/057160 A2 | 7/2003 |
| WO | 2005/121338 A1 | 12/2005 |

OTHER PUBLICATIONS

Lewin. Genes IV. 1990. Oxford University Press, p. 810.*
Rudikoff, Guisti, Cook, and Scharff. Single amino acid substitution altering antigen-binding specificity. Proceedings of the National Academy of Sciences, 1982. vol. 79, pp. 1979-1983.*
MacCallum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity-determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, McKay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Novus Biologicals Catalog, 2005. p. 160.*
Rabbit Polyclonal anti-PERP NB500-231 Antibody SPEC Sheet. 2006 Novus Biologicals. 2 pages.*
Wright, Shin, and Morrison. Genetically engineered antibodies: progress and prospects. Critical Reviews in Immunology, 1992. vol. 12, pp. 125-168.*
EP Office Action issued in 05749067.4 on Dec. 29, 2008.
Supplementary European Search Report issued in 05749067.4 on Jun. 25, 2007.
International Search Report issued in PCT/JP2005/010405 on Sep. 20, 2005.
Laura D. Attardi et al., "PERP, an apoptosis-associated target of p53, is a novel member of the PMP-22/gas3 family", Genes & Development, 2000, 14:704-718.
Homepage of Pro Sci Incorporated, online, retrieved on Mar. 31, 2004, Internet http://www.prosci-inc.com/Antibody-TDS/2451%20PERP.html.
S.J. McKenzie et al., "Generation and characterization of monoclonal antibodies specific for the human *neu* oncogene product, p185", Oncogene, 1989, 4(5): 543-548.
P.R. Tempest et al., "Reshaping a human monoclonal antibody to inhibit human respiratory syncytial virus infection in vivo", Biotechnology, 1991, 9(3): 266-271.
International Search Report issued in PCT/JP2006/324385 on Feb. 6, 2007.

(Continued)

*Primary Examiner* — Anne M. Gussow
(74) *Attorney, Agent, or Firm* — Sughrue Mion, PLLC

(57) ABSTRACT

An antibody which binds to a polypeptide encoded by human PERP (p53 apoptosis effector related to PMP-22) gene which is considered to be related to incidence of cancer or the like is desired. The present invention provides a gene recombinant antibody which has no consensus sequence of an N-linked sugar chain in a variable region, specifically recognizes three-dimensional structure of an extracellular region of a polypeptide encoded by the PERP gene and binds to the extracellular region. The antibody is useful for treatment of various diseases expressing a polypeptide encoded by the PERP gene.

16 Claims, 18 Drawing Sheets

OTHER PUBLICATIONS

Man Sung Co et al., "Genetically Engineered Deglycosylation of the Variable Domain Increases the Affinity of an Anti-CD33 Monoclonal Antibody", Molecular Immunology, 1993, 30(15): 1361-1367.

Non-Final Office Action mailed Feb. 19, 2010, in U.S. Appl. No. 11/628,745.

Campbell, Monoclonal Antibody Technology, 1984, Chapter 1, pp. 1-32.

Paul, Fundamental Immunology: Third Edition, 1993, pp. 292-295.

Marques, Michelle R. et al., "Mice Lacking the p53/p63 Target Gene Perp are Resistant to Papilloma Development", Aug. 2005, Cancer Research, vol. 65, No. 15, pp. 6551-6556.

Presta, Leonard G., "Selection, design, and engineering of therapeutic antibodies", Journal of Allergy and Clinical Immunology, vol. 116, No. 4, Oct. 1, 2005, pp. 731-736.

Extended European Search Report issued Mar. 30, 2010, in counterpart European Application No. 06834140.3.

"Rabbit Polyclonal anti-PERP: NB500-231" Novus Biologicals Inc., Jun. 5, 2004, 1 page.

Carter, P. et al., "Humanization of an anti-p185$^{HER2}$ antibody for human cancer therapy", Proceedings of the National Academy of Sciences of USA, vol. 89, May 1, 1992, pp. 4285-4289.

Atsushi Ochiai et al., Restriction Requirement mailed Sep. 24, 2009, in U.S. Appl. No. 11/628,745.

Atsushi Ochiai et al., Response to Restriction Requirement filed Oct. 23, 2009, in U.S. Appl. No. 11/628,745.

PERP Antibody Catalog No. NB500-231, Novus Biological Inc., Jun. 5, 2004, retrieved from http://web.archive.org/web/20040605025257/http://www.novus-biologicals.com.

Atsushi Ochiai et al., 1.111 Amendment and Statement of Availability filed Aug. 19, 2010, in U.S. Appl. No. 11/628,745.

Atsushi Ochiai et al., Final Office Action mailed Nov. 3, 2010, in U.S. Appl. No. 11/628,745.

EP 06834140.3 European Examination Report issued Sep. 28, 2010, in the name of Kyowa Hakko Kirin Co., Ltd. et al.

Atsushi Ochiai et al., RCE filed Apr. 6, 2011, in U.S. Appl. No. 11/628,745.

"Alphabetical Product List", website of Novus Biologicals, Nov. 15, 2003 (retrieved on Feb. 3, 2011), retrieved from http://web.archive.org/web/20031115052225/www.novus-biologicals.com/alpha.php/P/140.

AU 2005252521 Australian Examination Report issued on Sep. 22, 2009 (in the name of Japan as represented by President of National Cancer Center and Kyowa Hakko Kogyo Co., Ltd.).

EP 05749067.4 Office Action issued on Dec. 13, 2007 (in the name of Kyowa Hakko Kogyo Co., Ltd.).

EP 05749067.4 Office Action issued on Mar. 12, 2010 (in the name of Kyowa Hakko Kirin Co., Ltd.).

JP 2006-514511 Office Action issued Feb. 8, 2011 (in the name of Kyowa Hakko Kirin Co., Ltd.—with English-language translation).

"Novus Biologicals-PERP Antibody", website of Novus Biologicals, [retrieved on Jun. 23, 2005], retrieved from the Internet <URL:http://www.novus-biologicals.com/data_sheet.php/4400/S/PERP/0>.

Atsushi Ochiai et al., 1.116 Amendment filed Feb. 3, 2011, in U.S. Appl. No. 11/628,745.

Atsushi Ochiai et al., Advisory Action mailed Mar. 3, 2011, in U.S. Appl. No. 11/628,745.

Atsushi Ochiai et al., Notice of Allowance mailed Mar. 4, 2011, in U.S. Appl. No. 11/628,745.

* cited by examiner

FIG. 2
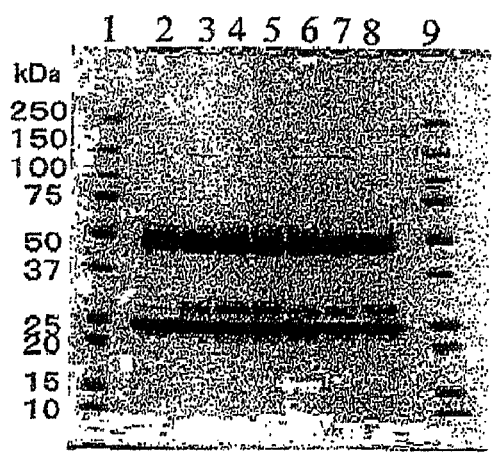
A
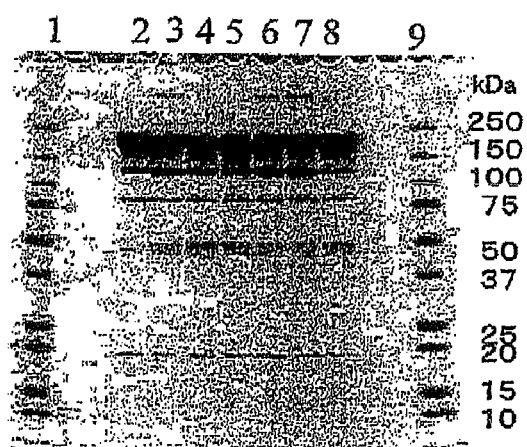
B

FIG. 12
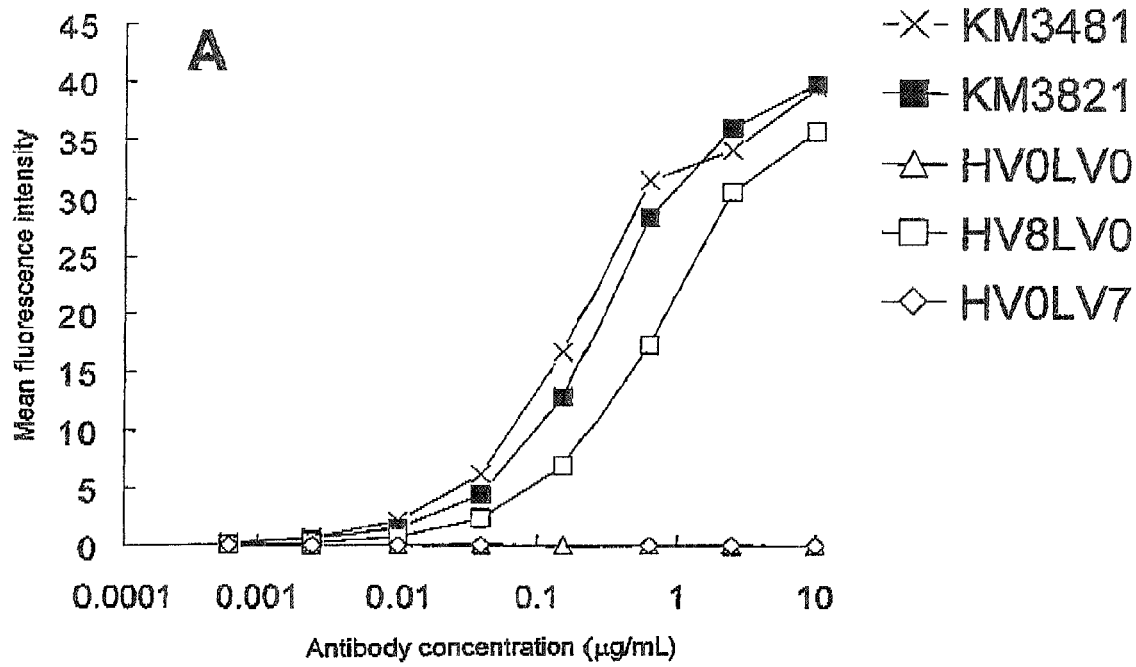
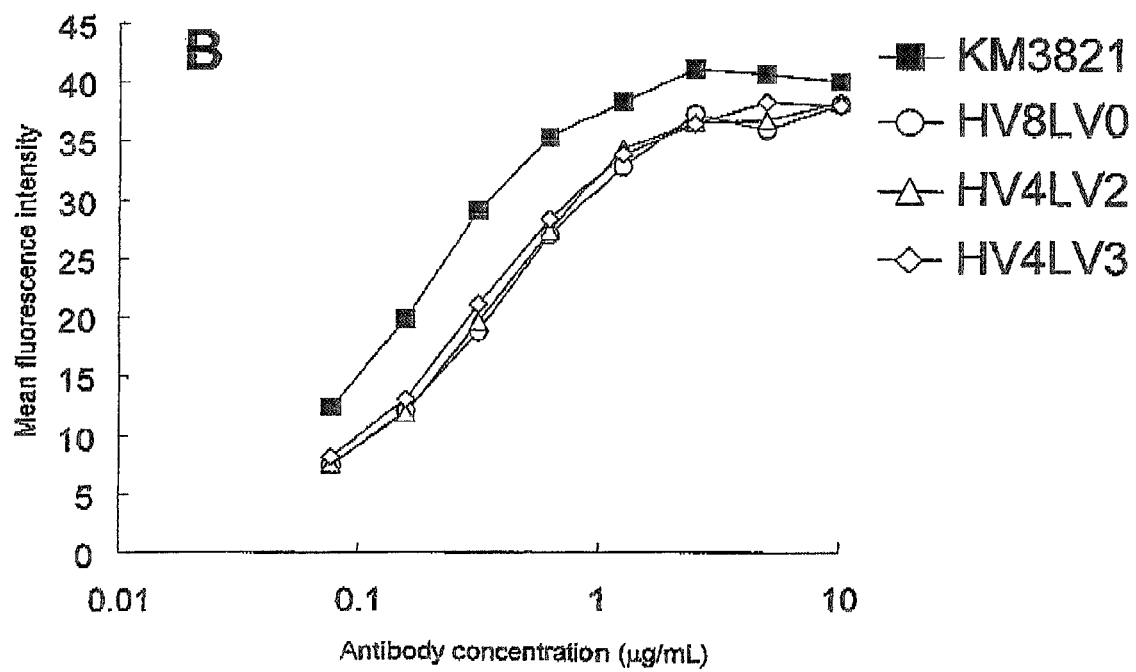

FIG. 15　Human lung cancer cell line PC-9

FIG. 16    Human pancreatic cancer cell line BxPC-3

FIG. 17  CHO/PERP (KC9033)

ANTI-PERP RECOMBINANT ANTIBODY

FIELD OF THE INVENTION

The present invention relates to a gene recombinant antibody which has no consensus sequence of an N-linked sugar chain in a variable region, specifically recognizes three-dimensional structure of an extracellular region of a polypeptide encoded by PERP (p53 apoptosis effector related to PMP-22) gene and binds to the extracellular region, or the antibody fragment thereof; and an agent for treating cancer using the gene recombinant antibody or the antibody fragment. Also, the present invention relates to a DNA encoding the gene recombinant antibody; a vector comprising the DNA; a transformant obtainable by transformation of the vector; and a process for producing the antibody which comprises culturing the transformant.

BACKGROUND OF THE INVENTION

A nucleotide sequence of PERP (hereinafter also referred to as THW or PIGPC1) has been already known (Patent references 1 to 13) and a polypeptide encoded by the PERP gene is presumed to be a protein comprising 193 amino acids and a 4-transmembrane protein from its primary sequence. It has been known that the polypeptide encoded by PERP gene is a protein related to p53-dependent apoptosis (Non-patent reference 1). It has been also shown that, in thymus cells and nerve cells prepared from PERP gene knockout mice, apoptosis induction upon damage of DNA is partially inhibited (Non-patent reference 2). It has been also reported that PERP is a gene which lowers its expression in highly metastatic cancer cells (Non-patent reference 3).

As an antibody binding to a polypeptide encoded by the PERP gene (hereinafter referred to as "anti-PERP antibody"), a polyclonal antibody prepared from an intracellular partial peptide in the C terminal or a partial peptide of the first extracellular loop in a PERP gene product as an immunogen has been known (Non-patent references 4 and 5). These polyclonal antibodies have been shown to be applicable to Western blotting or immunohistostaining. Up to now, no antibody which recognizes the three-dimensional structure of an extracellular region of polypeptide encoded by PERP gene and binds to the extracellular region has been known.

It has been known that, when an antibody of non-human animals such as a mouse antibody is administered to human, it is usually recognized as a xenobiotic substance and accordingly, a human antibody against a mouse antibody (human anti-mouse antibody: HAMA) is induced in human body. It has been known that HAMA reacts with the administered mouse antibody to induce side effects (Non-patent references 6 to 9), promotes the disappearance of the mouse antibody from the body (Non-patent references 7, 10 and 11) and reduces the therapeutic effect of the mouse antibody (Non-patent references 12 and 13).

In order to solve these problems, it has been attempted to prepare a humanized antibody such as a human chimeric antibody or a humanized antibody from an antibody of non-human animals by using genetic recombination techniques.

In comparison with an antibody of non-human animals such as a mouse antibody, the human chimeric antibody or the humanized antibody has various advantages in clinical application to human. It has been reported, for example, that, in experiments using monkeys, immunogenicity of the human chimeric antibody or the humanized is lowered and its half-life period in blood becomes longer in comparison with a mouse antibody (Non-patent references 14 and 15). Thus it is expected that, in comparison with the antibody of non-human animals, the human chimeric antibody or the humanized antibody has little side effects in human and its therapeutic effect lasts for a long period.

In addition, since the human chimeric antibody or the humanized antibody is prepared by using genetic recombination techniques, it can be prepared as molecules in various forms. For example, when the γ1 subclass is used as a heavy chain (hereinafter referred to as "H chain") constant region (hereinafter referred to as "C region") (H chain C region will be referred to as "CH") of a human antibody, it is possible to prepare a human chimeric antibody and a humanized antibody having a high effector function such as antibody-dependent cellular cytotoxicity (hereinafter referred to as "ADCC") (Non-patent reference 14) and prolonged half-life in blood can be expected in comparison with a mouse antibody (Non-patent reference 15). Particularly, in the treatment where expressed cell numbers of polypeptide encoded by the PERP gene are decreased, high cytotoxic activity such as complement-dependent cytotoxic activity (hereinafter referred to as "CDC activity") and ADCC activity via Fc region of an antibody (region which is in the downstream of a hinge region of the antibody H chain) is important to the therapeutic effect and, therefore, the human chimeric antibody and the humanized antibody is preferred in comparison with the antibody of non-human animals such as a mouse antibody (Non-patent references 16 and 17).

Moreover, as a result of the progress in protein engineering and genetic engineering in recent years, the human chimeric antibody or the humanized antibody can also be prepared as antibody fragment having a low molecular weight such as Fab, Fab', F(ab')$_2$, a single chain antibody (hereinafter referred to as "scFv") (Non-patent reference 18), a dimerized V region fragment (hereinafter be referred to as "diabody") (Non-patent reference 19), a disulfide stabilized V region fragment (hereinafter referred to as "dsFv") (Non-patent reference 20), a peptide comprising CDR (Non-patent reference 21) and the like, and these antibody fragments are better in transition to target tissues than whole antibody molecules (Non-patent reference 22).

The above-described facts show that, as an antibody to be used for clinical application to human, a human chimeric antibody, a humanized antibody or the antibody fragment thereof is preferred than an antibody of non-human animals such as a mouse antibody. Many proteins, including antibodies, existing in living organisms are modified by sugar chains. Sugar chains are classified into an N-linked sugar chain which specifically binds to an asparagine residue and an O-linked sugar chain which binds to a serine residue and a threonine residue. Particularly, in sugar proteins having an N-linked sugar chain, a consensus sequence (asparagine-any amino acid-serine or threonine) comprising three amino acid residues to which the sugar chain binds is present (Non-patent reference 23). However, it is not always true that an N-linked sugar chain binds to all consensus sequences. For example, in two consensus sequences of N-linked sugar chain in human TNF-α receptor II of maturation type, 100% N-linked sugar chain is bound in one of them while, in the other, N-linked sugar chain is bound in a possibility of as low as about 50% (Non-patent reference 24). The same phenomenon is also confirmed in bovine DNase I and, further, when a host cell for the production of genetic recombinant product changes, a pattern of sugar chain binding greatly changes and, even in the same amino acid sequence, addition of sugar chain is not constant depending upon the environment for protein expression (Non-patent reference 25).

Usually, a constant region of human antibody of IgG type has one consensus sequence of N-linked sugar chain. However, in an antibody having a consensus sequence of an N-linked sugar chain even in its variable region, binding of sugar chain changes and it becomes difficult to stably provide an antibody which is uniform as a pharmaceutical. Furthermore, there are some cases where sugar chain is essential for binding of proteins. For example, it has been reported that, in LFA-3 (lymphocyte function-associated antigen 3), an N-linked sugar chain is necessary for binding of LFA-3 to CD2 and there is a possibility that, when a sugar chain is bound to a variable region which is a binding site of an antibody, the binding activity of the antibody to the antigen is changed (Non-patent reference 26).

(Patent reference 1) WO98/55508
(Patent reference 2) WO99/54461
(Patent reference 3) WO00/55350
(Patent reference 4) WO01/22920
(Patent reference 5) WO01/66719
(Patent reference 6) WO00/61612
(Patent reference 7) WO02/00174
(Patent reference 8) WO02/47534
(Patent reference 9) US2003-0064947
(Patent reference 10) US2003-0065157
(Patent reference 11) WO00/55629
(Patent reference 12) WO02/60317
(Patent reference 13) US2002-0119463
(Non-patent reference 1) *Genes & Development*, 14, 704 (2000)
(Non-patent reference 2) *Curr. Biol.*, 13, 1985 (2003)
(Non-patent reference 3) *Anticancer Research*, 20, 2801 (2000)
(Non-patent reference 4) Home page of Pro Sci Incorporated, on line, retrieved on Mar. 31, 2004, internet <www.prosci-inc.com/Antibody-TDS/2451%20PERP.html>
(Non-patent reference 5) Home page of Novus Biologicals, Inc., on line, retrieved on Mar. 31, 2004, internet <www.novus-biologicals.com/print_data_sheet.php/4400>)
(Non-patent reference 6) *J. Clin. Oncol.*, 2, 881 (1984)
(Non-patent reference 7) *Blood*, 65, 1349 (1985)
(Non-patent reference 8) *J. Natl. Cancer Inst.*, 80, 932 (1988)
(Non-patent reference 9) *Proc. Natl. Acad. Sci. USA*, 82, 1242 (1985)
(Non-patent reference 10) *J. Nucl. Med.*, 26, 1011 (1985)
(Non-patent reference 11) *J. Natl. Cancer Inst.*, 80, 937 (1988)
(Non-patent reference 12) *J. Immunol.*, 135, 1530 (1985)
(Non-patent reference 13) *Cancer Res.*, 46, 6489 (1986)
(Non-patent reference 14) *Cancer Res.*, 56, 1118 (1996)
(Non-patent reference 15) *Immunol.*, 85, 668 (1995)
(Non-patent reference 16) *J. Immunol.*, 144, 1382 (1990)
(Non-patent reference 17) *Nature*, 322, 323 (1988)
(Non-patent reference 18) *Science*, 242, 423 (1988)
(Non-patent reference 19) *Nature Biotechnol.*, 15, 629 (1997)
(Non-patent reference 20) *Molecular Immunol.*, 32, 249 (1995)
(Non-patent reference 21) *J. Biol. Chem.*, 271, 2966 (1996)
(Non-patent reference 22) *Cancer Res.*, 52, 3402 (1992)
(Non-patent reference 23) *Biochem. J.*, 195, 639 (1981)
(Non-patent reference 24) *Biochemistry*, 32, 3131 (1993)
(Non-patent reference 25) *Biochem. J.*, 355, 245 (2001)
(Non-patent reference 26) *Trends in Glycoscience and Glycotechnology*, 11, 1 (1991)

SUMMARY OF THE INVENTION

In order to stably supply an antibody which is uniform as a medicament, it is necessary that the consensus sequence of an N-linked sugar chain is modified by amino acid substitution or the like. However, since a complimentary determining region is a region which directly contributes to the binding activity of the antibody to the antigen, it is not easy to conduct the modification with an amino acid together with retaining the binding activity of the antibody to the antigen. Objects of the present invention are to provide a gene recombinant antibody which has no consensus sequence of an N-linked sugar chain in a variable region, specifically recognizes three-dimensional structure of an extracellular region of a polypeptide encoded by the PERP gene and binds to the extracellular region, or the antibody fragment thereof; and an agent for treating cancer using the gene recombinant antibody or the antibody fragment. Also, the present invention relates to a DNA encoding the gene recombinant antibody or the antibody fragment; a vector comprising the DNA; a transformant obtainable by transformation of the vector; and a process for producing the antibody which comprises culturing the transformant.

The present invention relates to a gene recombinant antibody which has no consensus sequence of an N-linked sugar chain in a V region, specifically recognizes three-dimensional structure of an extracellular region of a polypeptide encoded by the PERP gene and binds to the extracellular region, or the antibody fragment thereof, and an agent for treating cancer using the gene recombinant antibody or the antibody fragment. Also, the present invention relates to a DNA encoding the gene recombinant antibody or the antibody fragment; a vector comprising the DNA; a transformant obtainable by transformation of the vector; and a process for producing the antibody which comprises culturing the transformant.

BRIEF DESCRIPTION OF THE DRAWINGS

FIG. 2 shows electrophoretic patterns of SDS-PAGE (using 5 to 20% gradient gel) of a purified anti-PERP CDR-modified antibody. "A" and "B" show the results under reducing conditions and that under non-reducing conditions, respectively. In both A and B, lanes 1 and 9 show molecular markers, lane 2 shows an anti-PERP chimeric antibody KM3481, and lanes 3 to 8 show, from left to right, migration patterns of ver.1 to ver.6 of the anti-PERP CDR-modified antibody, respectively.

FIG. 12 shows reactivity of the produced anti-PERP humanized antibody to the hPERP-expressed cells CHO/hPERP (KC 1359) in flow cytometry. The ordinate and the abscissa in each drawing show cell numbers and fluorescence intensity, respectively.

"A" shows reactivity of a humanized antibody in which CDR is merely inserted into a human framework and reactivity of a humanized antibody to which only H chain or L chain is modified with an amino acid. "B" shows reactivity of a humanized antibody in which number of modified amino acids is decreased.

Figure 13:
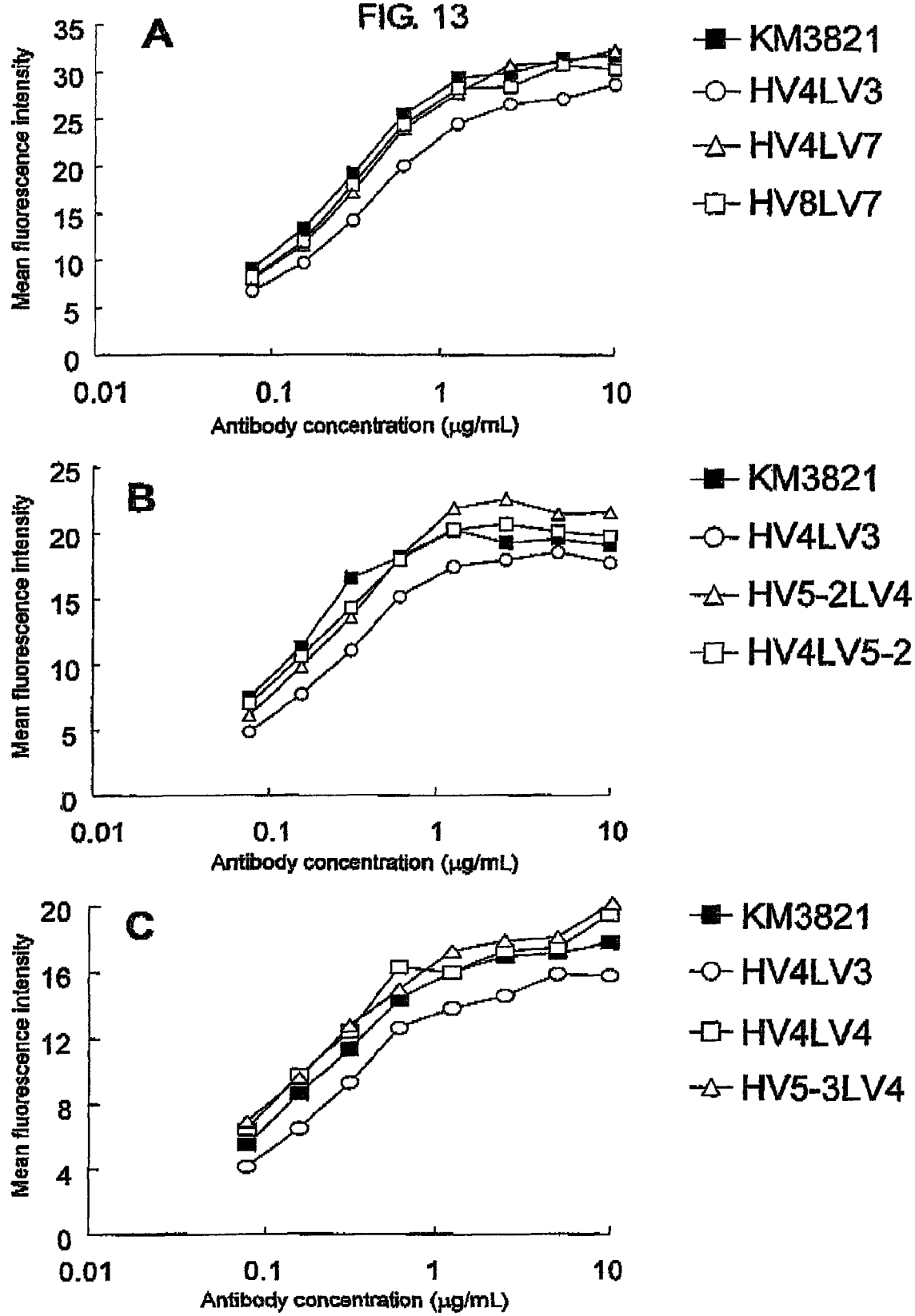

FIG. 13 shows reactivity of the produced anti-PERP humanized antibody to hPERP-expressed cells CHO/hPERP (KC 1359) in a flow cytometry. The ordinate and the abscissa in each drawing show cell numbers and fluorescence intensity, respectively.

"A", "B" and "C" show reactivity of an anti-PERP humanized antibody in which amino acid-modified residues are optimized.

Figure 14:
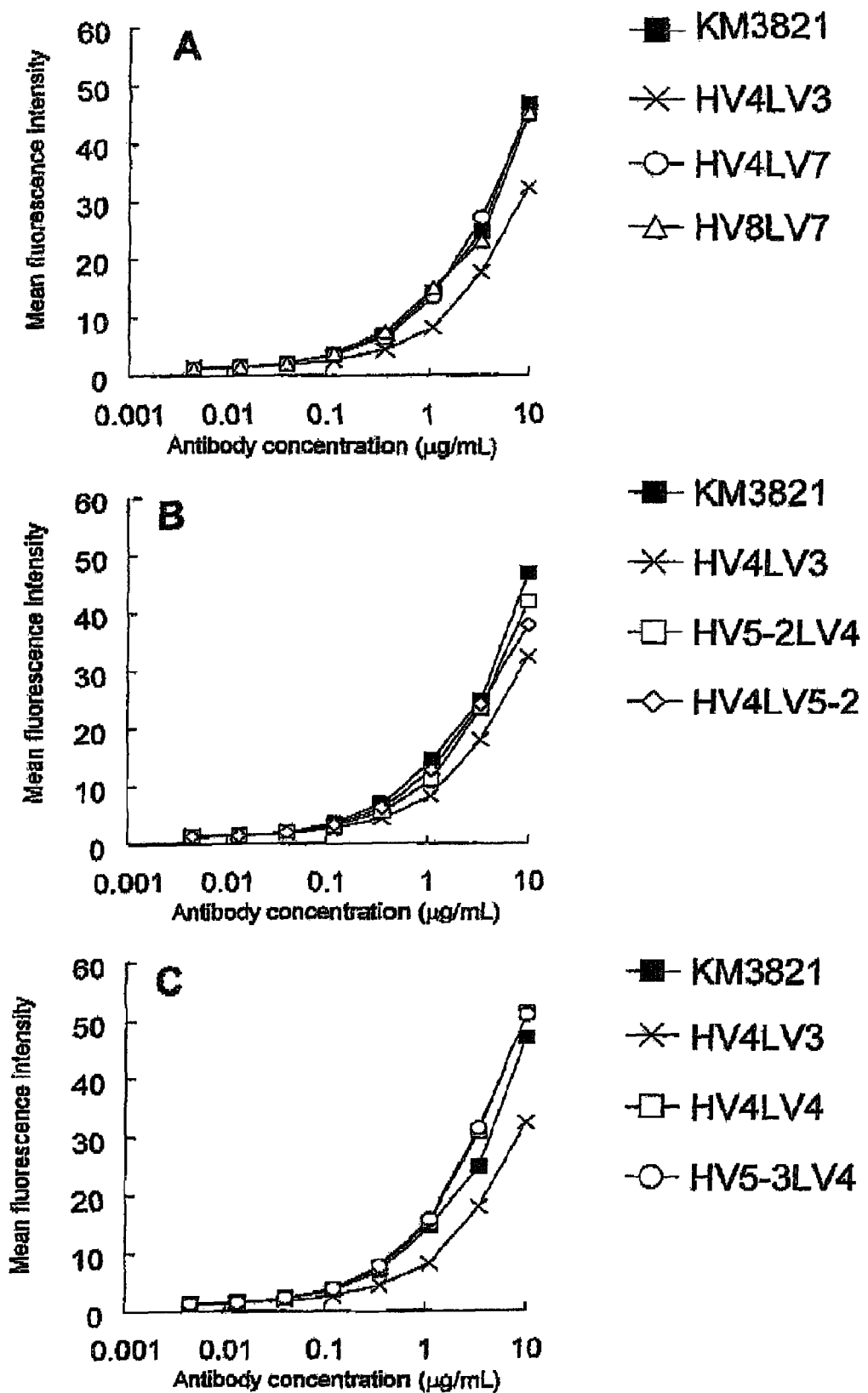

FIG. 14 shows reactivity of the produced anti-PERP humanized antibody to the hPERP-expressed cells human lung cancer cell line PC-9 in a flow cytometry. The ordinate and the abscissa in each drawing show cell numbers and fluorescence intensity, respectively.

"A", "B" and "C" show reactivity of an anti-PERP humanized antibody in which amino acid-modified residues are optimized.

Figure 15:
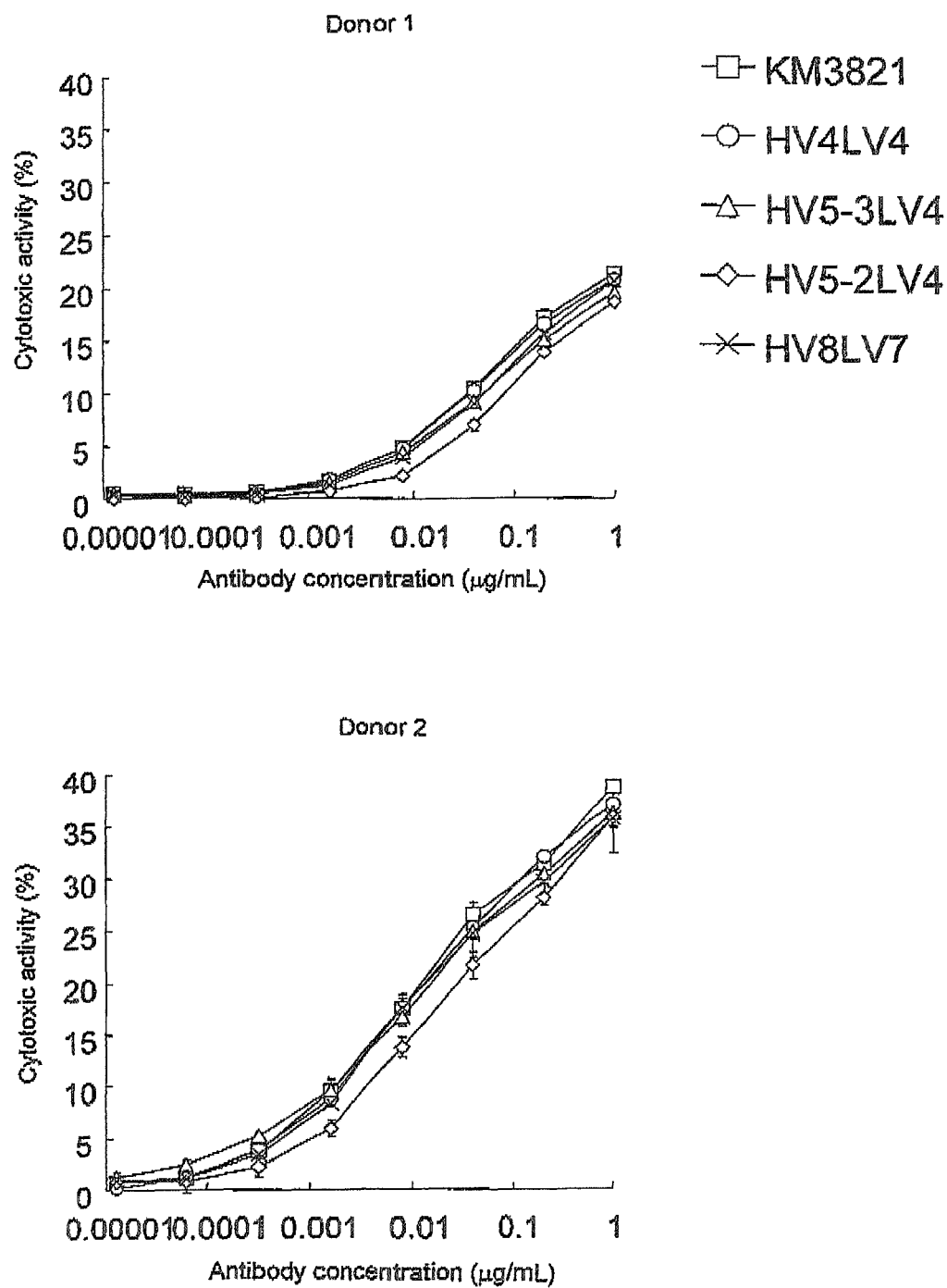

FIG. 15 shows ADCC activity of each of the produced anti-PERP humanized antibody to human lung cancer cell line PC-9. The ordinate and the abscissa in each drawing show cytotoxic activity (%) and antibody concentration, respectively.

Figure 16:
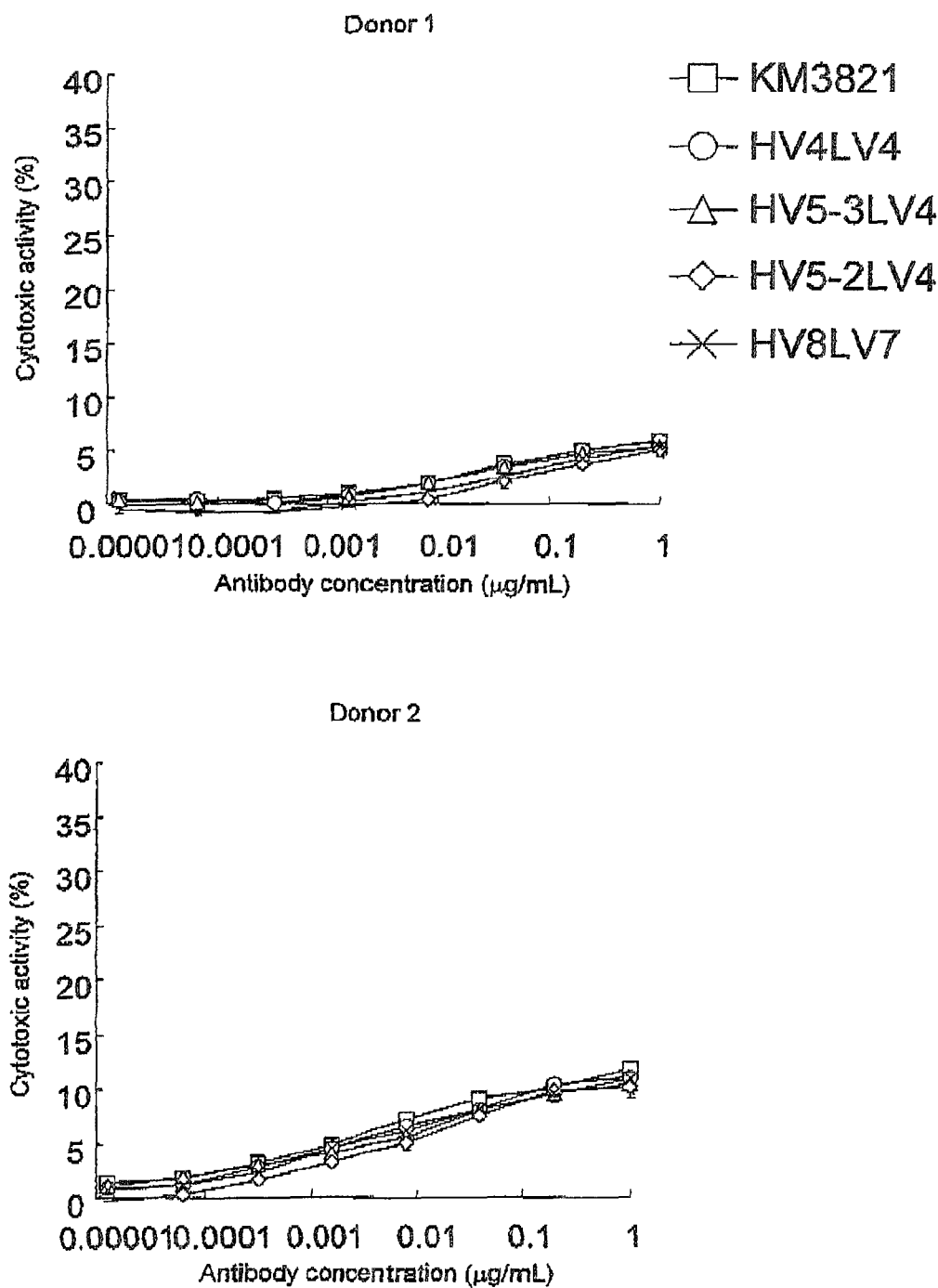

FIG. 16 shows ADCC activity of each of the produced anti-PERP humanized antibody to human pancreatic cancer cell line BxPC-3. The ordinate and the abscissa in each drawing show cytotoxic activity (%) and antibody concentration, respectively.

Figure 17:
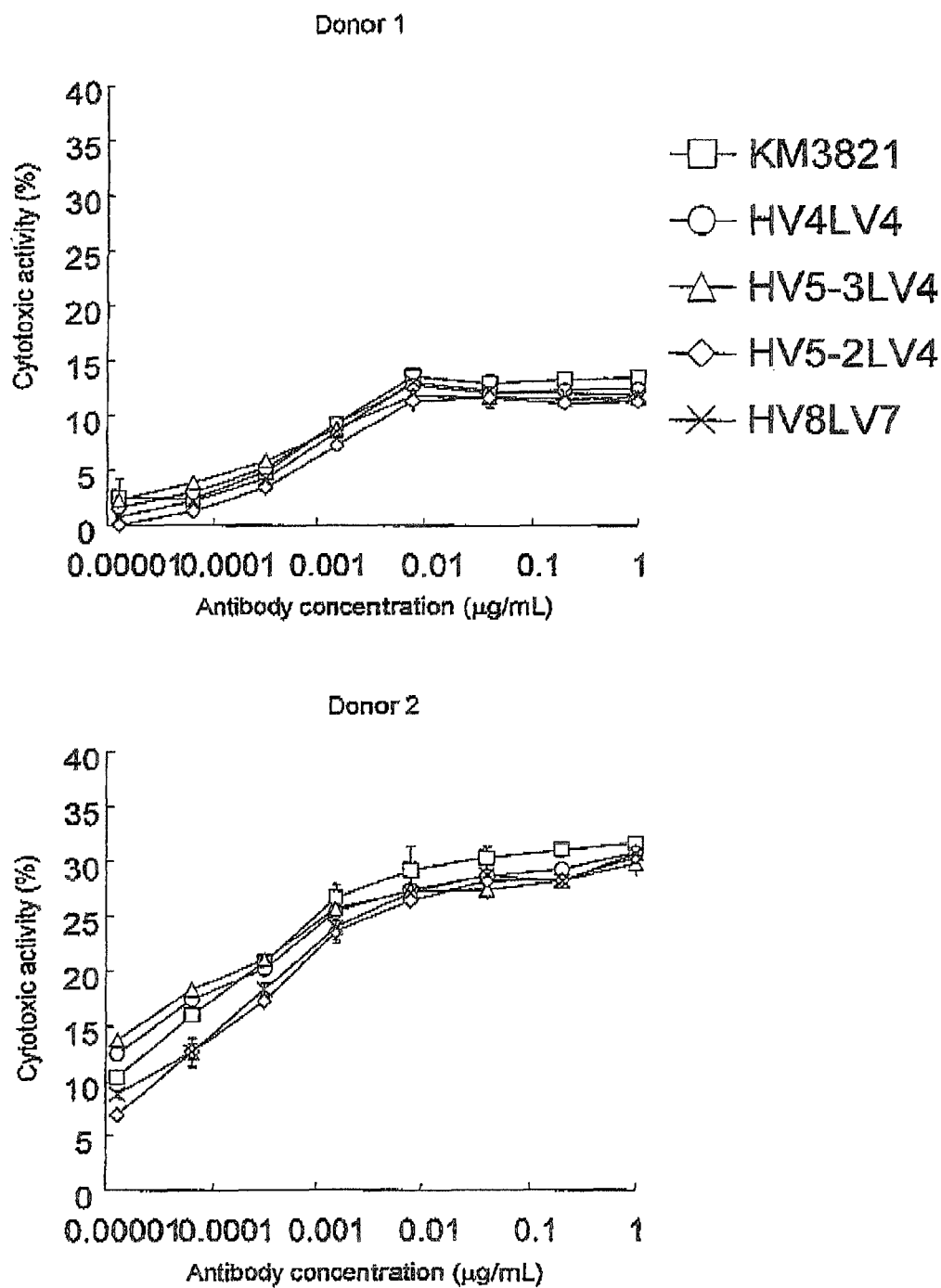

FIG. 17 shows ADCC activity of each of the produced anti-PERP humanized antibody to hPERP-expressed CHO cell CHO/hPERP (KC9033). The ordinate and the abscissa show cytotoxic activity (%) and antibody concentration, respectively.

Figure 18:
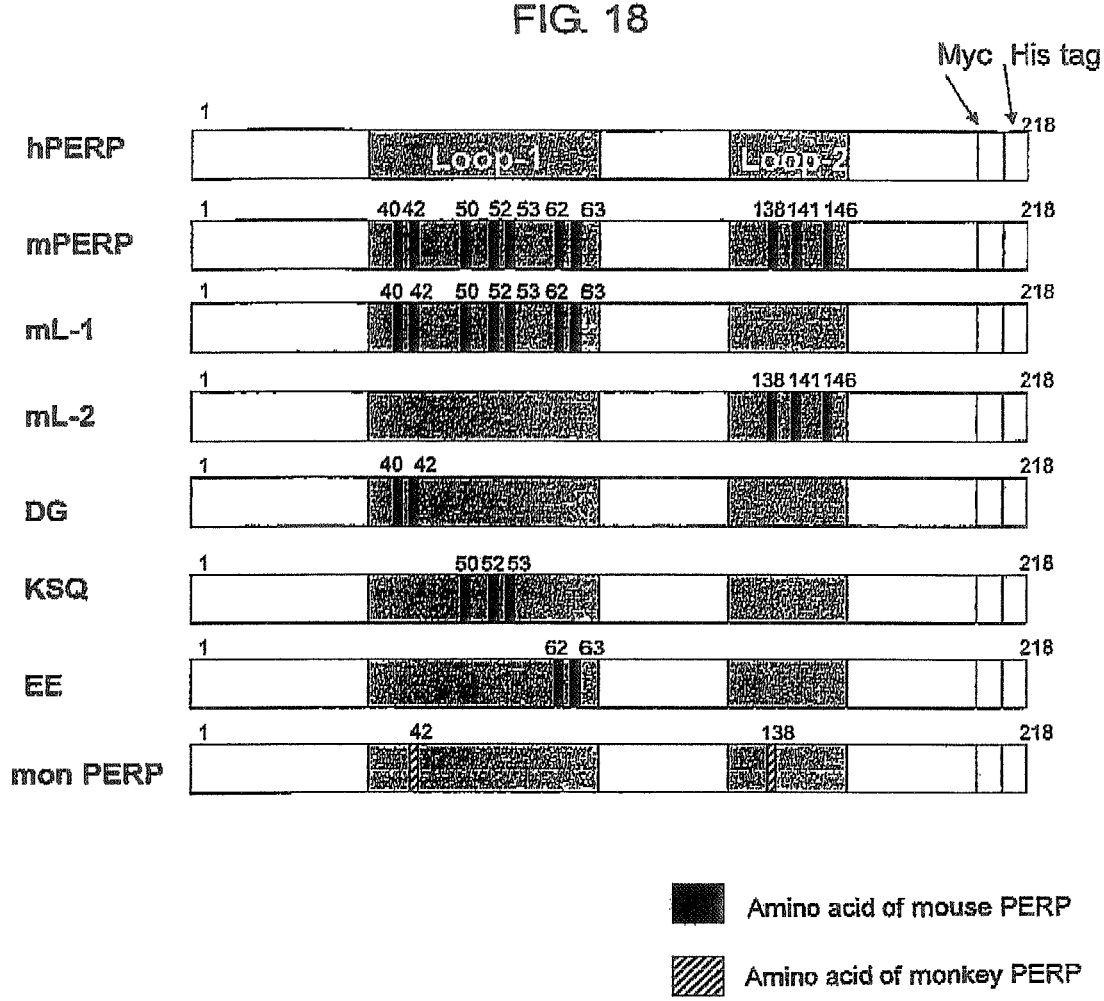

FIG. 18 shows a schematic drawing of a mutant PERP based on the result of an epitope analysis of an anti-PERP humanized chimeric antibody KM3821 having no consensus sequence of an N-linked sugar chain.

Figure 19:
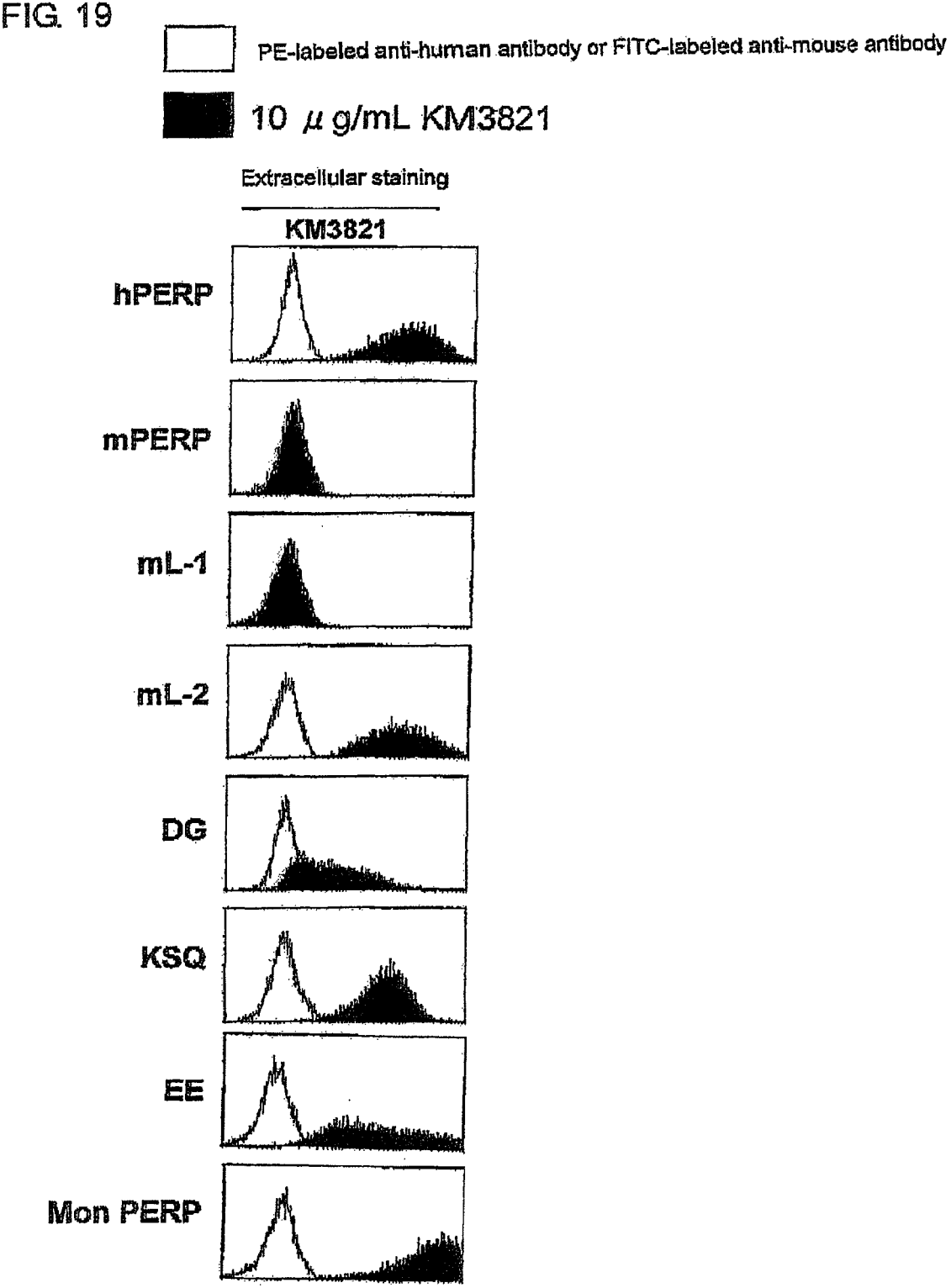

FIG. 19 shows reactivity of an antibody which recognizes an extracellular region of PERP to each mutant PERP in a flow cytometry. Value in the graph shows reactivity of KM3821. Reactivity of KM3821 is given in terms of reactivity (%) to each mutant PERP or monkey PERP when reactivity of KM3821 to hPERP is defined as 100%.

Figure 20:
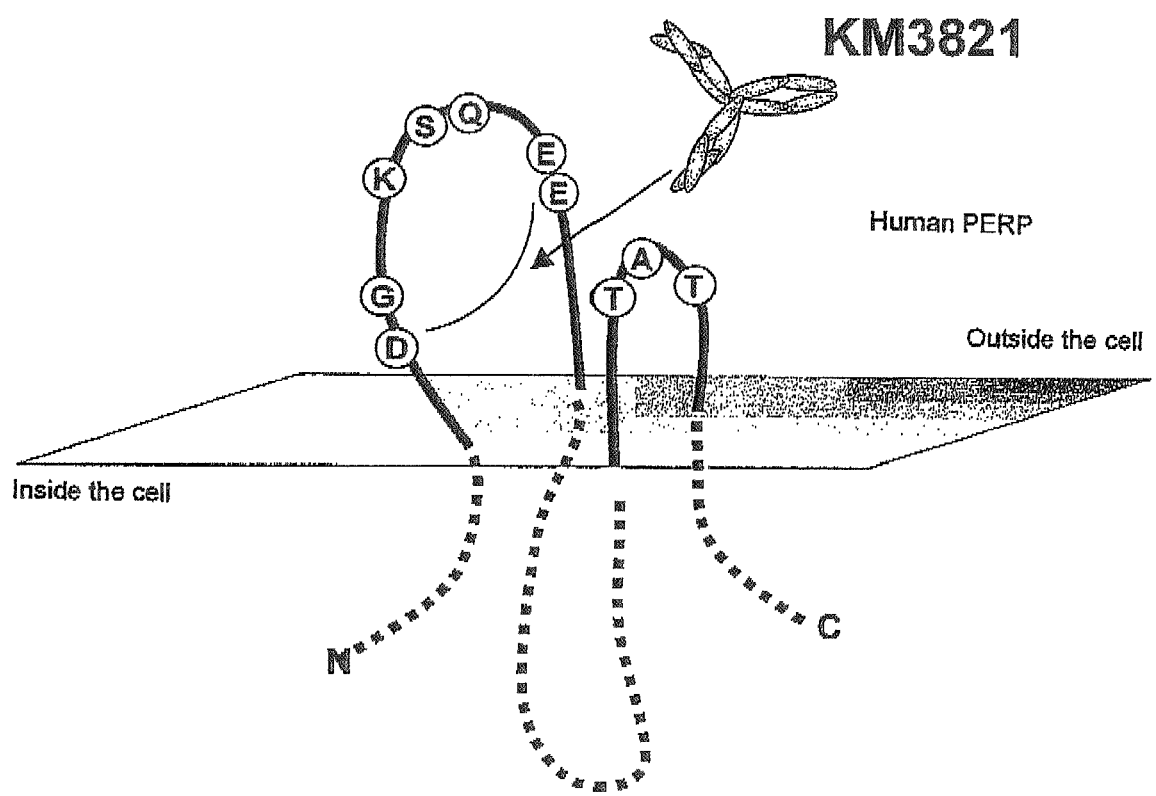

FIG. 20 schematically shows an epitope found from reactivity of KM3821 to each mutant PERP expression cell in a flow cytometry.

DETAILED DESCRIPTION OF THE INVENTION

The present invention relates to the following (1) to (31):

(1) A gene recombinant antibody which has no consensus sequence of an N-linked sugar chain in a variable region (hereinafter referred to as V region) in the antibody, specifically recognizes three-dimensional structure of an extracellular region of a polypeptide encoded by the PERP gene and binds to the extracellular region or the antibody fragment thereof.

(2) The gene recombinant antibody or the antibody fragment according to (1), which has no consensus sequence in all comprimentarity determining region (hereinafter referred to as CDRs) in a heavy chain variable region (hereinafter referred to as VH) and a light chain variable region (hereinafter referred to as VL) in the antibody.

(3) The gene recombinant antibody or the antibody fragment according to (1) or (2), wherein CDR1 and CDR3 of VH of the antibody comprise the amino acid sequences represented by SEQ ID NOs:3 and 5, respectively.

(4) The gene recombinant antibody or the antibody fragment according to (1) or (2), wherein CDR1, CDR2 and CDR3 of VL of the antibody comprise the amino acid sequences represented by SEQ ID NOs:11, 12 and 13, respectively.

(5) The gene recombinant antibody or the antibody fragment according to (1) or (2), wherein CDR1 and CDR3 of VH of the antibody comprise the amino acid sequences represented by SEQ ID NOs:3 and 5, respectively, and CDR1, CDR2 and CDR3 of VL of the antibody comprise the amino acid sequences represented by SEQ ID NOs:11, 12 and 13, respectively.

(6) The gene recombinant antibody or the antibody fragment according to any one of (1) to (5), wherein CDR2 of VH of the antibody comprises an amino acid sequence into which at least one modification is introduced, said modification being selected from a modification in which Asn at position 9 in the amino acid sequence represented by SEQ ID NO:45 is substituted with other amino acid residues and a modification in which Ser at position 11 in the amino acid sequence represented by SEQ ID NO:45 is substituted with other amino acid residues.

(7) The gene recombinant antibody or the antibody fragment according to (6), wherein the modification in which Asn at position 9 in the amino acid sequence represented by SEQ ID NO:45 is substituted with other amino acid residues is a modification in which Asn at position 9 is substituted with amino acid residue having a polar side chain.

(8) The gene recombinant antibody or the antibody fragment according to (7), wherein the amino acid residue having a polar side chain is Tyr or Ser.

(9) The gene recombinant antibody or the antibody fragment according to (6), wherein the modification in which Asn at position 9 in the amino acid sequence represented by SEQ ID NO:45 is substituted with other amino acid residues is a modification in which Asn at position 9 is substituted with Gly.

(10) The gene recombinant antibody or the antibody fragment according to any one of (4) to (9), wherein the modification in which Ser at position 11 in the amino acid sequence represented by SEQ ID NO:45 is substituted with other amino acid residues is a modification in which Ser at position 11 is substituted with other amino acid residues having a nonpolar side chain.

(11) The gene recombinant antibody or the antibody fragment according to (10), wherein the amino acid residue having a nonpolar side chain is Ala.

(12) The gene recombinant antibody or the antibody fragment according to any one of (1) to (11), wherein CDR2 of VH of the antibody comprises the amino acid sequence represented by any one of SEQ ID NOs:4 and 6 to 10.

(13) The gene recombinant antibody or the antibody fragment according to any one of (1) to (12), wherein the gene recombinant antibody is selected from a human chimeric antibody, a humanized antibody and a human antibody.

(14) The human chimeric antibody or the antibody fragment according to (13), wherein VH of the human chimeric antibody comprises the amino acid sequence represented by any one of SEQ ID NOs: 14 to 19.

(15) The human chimeric antibody or the antibody fragment according to (13), wherein VL of the human chimeric antibody comprises the amino acid sequence represented by SEQ ID NO:20.

(16) The human chimeric antibody or the antibody fragment according to (13), wherein VH of the human chimeric antibody comprises the amino acid sequence represented by any one of SEQ ID NOs:14 to 19, and VL of the human chimeric antibody comprises the amino acid sequence represented by SEQ ID NO:20.

(17) The humanized antibody or the antibody fragment according to (13), wherein VH of the humanized antibody comprises the amino acid sequence represented by any one of SEQ ID NOs:30 to 35 or an amino acid sequence in which at least one modification is introduced into the amino acid sequence represented by any one of SEQ ID NOs:30 to 35, said modification being selected from substitutions of Gly at position 27 with Phe, Ser at position 30 with Thr, Pro at position 41 with Phe, Lys at position 44 with Asn, Gly at position 45 with Arg, Ile at position 49 with Met, Val at position 72 with Arg and Ala at position 97 with Thr.

(18) The humanized antibody or the antibody fragment according to (13), wherein VL of the humanized antibody comprises the amino acid sequence represented by SEQ ID NO:36 or an amino acid sequence in which at least one modification is introduced into the amino acid sequence represented by SEQ ID NO:36, said modification being selected from substitutions of Gln at position 3 with Val, Thr at position 5 with Ile, Tyr at position 35 with Phe, Ala at position 42 with Ser, Leu at position 46 with Trp, Ile at position 49 with Met, Phe at position 70 with Tyr, Thr at position 71 with Ser and Leu at position 77 with Met.

(19) The humanized antibody or the antibody fragment according to (13),
wherein VH of the humanized antibody comprises the amino acid sequence represented by any one of SEQ ID NOs:30 to 35 or an amino acid sequence in which at least one modification is introduced into the amino acid sequence represented by one of SEQ ID NOs:30 to 35, said modification being selected from substitutions of Gly at position 27 with Phe, Ser at position 30 with Thr, Pro at position 41 with Phe, Lys at position 44 with Asn, Gly at position 45 with Arg, Ile at position 49 with Met, Val at position 72 with Arg and Ala at position 97 with Thr, and
wherein VL of the humanized antibody comprises the amino acid sequence represented by SEQ ID NO:36 or an amino acid sequence in which at least one modification is introduced into the amino acid sequence represented by SEQ ID NO:36, said modification being selected from substitutions of Gln at position 3 with Val, Thr at position 5 with Ile, Tyr at position 35 with Phe, Ala at position 42 with Ser, Leu at position 46 with Trp, Asp at position 69 with Ser, Phe at position 70 with Tyr, Thr at position 71 with Ser and Leu at position 77 with Met.

(20) The humanized antibody or the antibody fragment according to (13), wherein VH of the humanized antibody comprises the amino acid sequence represented by any one of SEQ ID NOs:51 to 56.

(21) The humanized antibody or the antibody fragment according to (13), wherein VL of the humanized antibody comprises the amino acid sequence represented by any one of SEQ ID NOs:58 to 63.

(22) The humanized antibody or the antibody fragment according to (13), wherein VH of the humanized antibody comprises the amino acid sequence represented by any one of SEQ ID NOs:51 to 56, and VL of the humanized antibody comprises the amino acid sequence represented by one of SEQ ID NOs:58 to 63.

(23) The gene recombinant antibody or the antibody fragment according to any one of (1) to (22), which binds to an epitope recognized by a monoclonal antibody produced by a hybridoma KM3411 (FERM BP-8643).

(24) The antibody fragment according to any one of (1) to (23), wherein the antibody fragment is an antibody fragment selected from Fab, Fab', F(ab')$_2$, a single chain antibody (scFv), a dimerized V region (diabody), a disulfide stabilized V region (dsFv) and a peptide comprising CDR.

(25) The gene recombinant antibody or the antibody fragment according to any one of (1) to (24), wherein the three-dimensional structure is a three-dimensional structure comprising Asp at position 40, Glu at position 62 and Glu at position 63 in the amino acid sequence represented by SEQ ID NO:2.

(26) A DNA encoding the gene recombinant antibody or the antibody fragment described in any one of (1) to (25).

(27) A recombinant vector comprising the DNA described in (26).

(28) A transformant obtainable by introducing the recombinant vector described in (27) into a host cell.

(29) A process for producing the gene recombinant antibody or the antibody fragment described in any one of (1) to (25), which comprises culturing the transformant described in (28) in a medium to form and accumulate the gene recombinant antibody or the antibody fragment according to any one of (1) to (25) in the culture, and recovering the gene recombinant antibody or the antibody fragment from the culture.

(30) A therapeutic agent for treating a disease related to the PERP gene, which comprises the gene recombinant antibody or the antibody fragment described in any one of (1) to (25) as an active ingredient.

(31) The therapeutic agent according to (30), wherein the disease related to the PERP gene is cancer.

The present invention is explained below in detail.

The present invention relates to a gene recombinant antibody which has no consensus sequence of an N-linked sugar chain in a V region, specifically recognizes three-dimensional structure of an extracellular region of a polypeptide encoded by the PERP gene and binds to the extracellular region, or the antibody fragment thereof.

The PERP gene includes the nucleotide sequence represented by SEQ ID NO:1. The PERP gene of the present invention also includes a gene comprising a nucleotide sequence in which one or more nucleotide(s) is/are deleted, substituted, inserted or added in the above nucleotide sequence; a gene comprising a nucleotide sequence having at least 60% or more homology, preferably a nucleotide sequence having 80% or more homology, more preferably a nucleotide sequence having 90% or more homology, and most preferably a nucleotide sequence having 95% or more homology, of the nucleotide sequence represented by SEQ ID NO:1; a gene comprising a DNA which hybridizes with the DNA comprising the nucleotide sequence represented by SEQ ID NO:1 under stringent conditions; and the like.

A DNA which hybridizes under stringent conditions is a DNA obtained, e.g., by a method such as colony hybridization, plaque hybridization, Southern blot hybridization and DNA microarray method using a DNA having the nucleotide sequence represented by SEQ ID NO:1 as a probe, and specifically includes a DNA which can be identified by carrying out hybridization at 65° C. in the presence of 0.7 to 1.0 mol/L sodium chloride using a filter or a slide glass with colony- or plaque-derived DNA, a PCR product having the sequence or an oligonucleotide DNA immobilized thereon, and then washing the filter or the slide glass at 65° C. using 0.1 to 2-fold concentration SSC solution (composition of the 1-fold concentration SSC solution comprising 150 mmol/L sodium chloride and 15 mmol/L sodium citrate). The hybridization can be carried out in accordance with the methods described, e.g., *Molecular Cloning, A Laboratory Manual*, Second Edition, Cold Spring Harbor Laboratory Press (1989), *Current Protocols in Molecular Biology*, John Wiley & Sons (1987-1997), *DNA Cloning*, 1: *Core Techniques, A Practical Approach*, Second Edition (Oxford University (1995); and the like. The DNA capable of hybridizing includes a DNA having, at least 60% or more, preferably 80% or more, more preferably 90% or more, still more preferably 95% or more, and most preferably 99% or more, homology with the nucleotide sequence represented by SEQ ID NO:1.

In the nucleotide sequence of the gene encoding a protein of a eukaryote, genetic polymorphism is often recognized. The PERP gene of the present invention also includes a gene in which small modification is generated in the nucleotide sequence by such polymorphism as the gene used in the present invention.

The polypeptide encoded by the PERP gene includes a polypeptide comprising the amino acid sequence represented by SEQ ID NO:2; a polypeptide comprising an amino acid sequence in which one or more amino acid(s) is/are deleted, substituted, inserted or added in the amino acid sequence represented by SEQ ID NO:2; a polypeptide comprising an amino acid sequence having 60% or more homology, preferably a polypeptide comprising the amino acid sequence having 80% or more homology, more preferably a polypeptide comprising the amino acid sequence having 90% or more homology, still more preferably a polypeptide comprising the amino acid sequence having 95% or more homology, and most preferably a polypeptide comprising the amino acid sequence having 99% or more homology, with the amino acid sequence represented by SEQ ID NO:2; and the like.

The polypeptide which comprises an amino acid sequence in which one or more amino acid(s) is/are deleted, substituted, inserted or added in the amino acid sequence represented by SEQ ID NO:2 can be obtained, e.g., by introducing a site-directed mutation into a DNA encoding a polypeptide comprising the amino acid sequence represented by SEQ ID NO:2, using the site-directed mutagenesis described, e.g., in *Molecular Cloning, A Laboratory Manual*, Second Edition, Cold Spring Harbor Laboratory Press (1989); *Current Protocols in Molecular Biology*, John Wiley & Sons (1987-1997); *Nucleic Acids Research*, 10, 6487 (1982); *Proc. Natl. Acad. Sci. USA*, 79, 6409 (1982); *Gene*, 34, 315 (1985); *Nucleic Acids Research*, 13, 4431 (1985); *Proc. Natl. Acad. Sci. USA*, 82, 488 (1985); and the like. The number of amino acids to be deleted, substituted, inserted or added is not particularly limited, and the number of amino acids is preferably 1 to several tens, e.g., 1 to 20, and more preferably 1 to several, e.g., 1 to 5.

The number of the homology described in the present invention may be a known number calculated by using a known homology search program, unless otherwise indicated. Regarding the nucleotide sequence, the number may be calculated by using a default parameter in BLAST [*J. Mol. Biol.*, 215, 403 (1990)] or the like, and regarding the amino acid sequence, the number may be calculated by using a default parameter in BLAST2 [*Nucleic Acids Res.*, 25, 3389 (1997); *Genome Res.*, 7, 649 (1997); www.ncbi.nlm.nih.gov/Education/BLASTinfo/information3.html] or the like.

As the default parameter, G (cost to open gap) is 5 for the nucleotide sequence and 11 for the amino acid sequence; −E (cost to extend gap) is 2 for the nucleotide sequence and 1 for the amino acid sequence; −q (penalty for nucleotide mismatch) is −3; −r (reward for nucleotide match) is 1; −e (expect value) is 10; −W (wordsize) is 11 residues for the nucleotide sequence and 3 residues for the amino acid sequence; −y (dropoff (X) for blast extensions in bits) is 20 for blastn and 7 for a program other than blastn; −X (X dropoff value for gapped alignment in bits) is 15; and −Z (final X dropoff value for gapped alignment in bits) is 50 for blastn and 25 for a program other than blastn (www.ncbi.nlm.nih.gov/blast/html/blastcgihelp.html).

The polypeptide comprising a partial sequence of the amino acid sequence represented by SEQ ID NO:2 can be prepared according to a method known by the skilled person. For example, it can be prepared by deleting a part of DNA encoding the amino acid sequence represented by SEQ ID NO:2 and culturing a transformant into which an expression vector containing the DNA is introduced. Also, based on the thus prepared polypeptide or DNA, a polypeptide comprising an amino acid sequence in which one or more amino acid(s) is/are deleted, substituted, inserted or added in a partial sequence of the amino acid sequence represented by SEQ ID NO:2 can be prepared in the same manner as described above.

The extracellular region of a polypeptide encoded by the PERP gene is, for example, a region predicted by a known transmembrane region prediction program SOSUI (sosui.proteome.bio.tuat.acjp/sosuiframe0.html), prediction program TMHMM ver.2 (www.cbs.dtu.dk/services/TMHMM-2.0/), or the like, based on the amino acid sequence of the polypeptide represented by SEQ ID NO:2.

Specifically, when SOSUI is used, the extracellular region is predicted as a region corresponding to positions 35 to 75 and 130 to 154 in the amino acid sequence represented by SEQ ID NO:2. When TMHMM ver.2 is used, it is predicted as a region corresponding to positions 36 to 76 and 129 to 147 in the amino acid sequence represented by SEQ ID NO:2. At this time, as the parameters used for the prediction, default values in these prediction programs are used.

Also, the extracellular region of a polypeptide encoded by the PERP gene in the present invention may be a region corresponding to positions 33 to 75 and 129 to 150 in the extracellular domain predicted by literature [*Genes & Development*, 14, 704 (2000)].

The gene recombinant antibody or the antibody fragment thereof in the present invention can recognizes natural three-dimensional structure of a polypeptide encoded by the PERP gene and binds stably to the extracellular region of the polypeptide. The extracellular region includes loop 1 and loop 2 in the extracellular region of the polypeptide encoded by the PERP gene. The extracellular region includes a region comprising at least Asp at position 40 in loop 1 of the extracellular region, such as a three-dimensional structure comprising Asp at position 40, Glu at position 62 and Glu at position 63 in the amino acid sequence represented by SEQ ID NO:2.

The natural three-dimensional structure of a polypeptide encoded by the PERP gene may be any three-dimensional structure, so long as it is equivalent to the structure of a naturally existing polypeptide encoded by the PERP gene comprising the nucleotide sequence represented by SEQ ID NO:1.

The method for confirming the binding of the gene recombinant antibody of the present invention includes, for example, known immunological detection methods for cells in which a polypeptide encoded by the PERP gene is expressed, and a method for confirming the binding of a cell in which a specific antigen is expressed and an antibody against the specific antigen such as a fluorescent cell staining method is suitably used. Examples include an immunofluorescent staining method described in (2)-4 of Reference Example 1. Also, it can be confirmed by combining known immunological detection methods [*Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

The cell in which the polypeptide encoded by the PERP gene is expressed includes a cell naturally existing in human body, a cell line established from a cell naturally existing in human body, a cell obtained by gene recombinant technique, and the like.

The cell naturally existing in human body include a cell which expresses the polypeptide in the living body of a cancer patient, such as a cell expressing the polypeptide among tumor cells obtained by biopsy or the like.

The cell line established from a cell naturally existing in human body includes a cell line expressing the polypeptide among cell lines obtained by establishing the above cell expressing the polypeptide obtained by the cancer patient.

Examples include cell lines established from human such as pancreatic cancer cell line Capan-2 (ATCC HTB-80) or BxPC-3 (ATCC CRL-1687), colorectal cancer cell line Colo205 (ATCC CCL-222), HT29 (ATCC HTB-38) or WiDr (ATCC CCL-218), lung cancer cell line NCI-H128 (ATCC HTB-120) or NCI-H69 (ATCC HTB-119), breast cancer cell line MCF7 (ATCC HTB-22) and uterus cancer cell line MCAS (JCRB 0240).

The cell obtained by gene recombinant technique includes, for example, a cell expressing the polypeptide obtained by introducing an expression vector containing cDNA encoding the polypeptide into an insect cell or an animal cell, and the like, such as a cell expressing the polypeptide into which PERP gene expression plasmid pcPERPmH is introduced as described in Reference Example 1.

The gene recombinant antibody having no consensus sequence of an N-linked sugar chain in V region of the present invention includes a gene recombinant antibody having no consensus sequence of an N-linked sugar chain in all CDRs of V region, such as a gene recombinant antibody in which CDR1 and CDR3 of VH of the antibody comprise the amino acid sequences represented by SEQ ID NOs:3 and 5, respectively, and/or CDR1, CDR2 and CDR3 of VL of the antibody comprise the amino acid sequences represented by SEQ ID NOs:11, 12 and 13, respectively.

In the above gene recombinant antibody in which CDR1 and CDR3 of VH of the antibody comprise the amino acid sequence represented by SEQ ID NOs:3 and 5, respectively, CDR2 of VH of the antibody is not limited, so long as it is CDR2 of VH of the antibody having no consensus sequence of an N-linked sugar chain and the gene recombinant antibody comprising the CDR2 specifically recognizes three-dimensional structure of an extracellular region of a polypeptide encoded by the PERP gene and binds to the extracellular region. Examples include CDR2 comprising an amino acid sequence into which at least one modification is introduced, said modification being selected from a modification in which Asn at position 9 in the amino acid sequence represented by SEQ ID NO:45 is substituted with other amino acid residues and a modification in which Ser at position 11 in the amino acid sequence represented by SEQ ID NO:45 is substituted with other amino acid residues. The modification in which Asn at position 9 in the amino acid sequence represented by SEQ ID NO:45 is substituted with other amino acid residues includes a modification in which Asn at position 9 is substituted with an amino acid residue having a polar side chain. The amino acid residue having a polar side chain includes Glu, His, Lys, Tyr, Arg, Cys, Thr, Ser and the like. Other modification in which Asn at position 9 in the amino acid sequence represented by SEQ ID NO:45 is substituted with other amino acid residues includes a modification for substitution with Gly. The modification in which Ser at position 11 in the amino acid sequence represented by SEQ ID NO:45 is substituted with other amino acid residues includes a modification in which Ser at position 11 is substituted with an amino acid residue having a non polar side chain. The amino acid residue having a non polar side chain includes Trp, Ile, Phe, Leu, Met, Val, Pro, Ala, Gly and the like. The above CDR2 of VH of the antibody includes CDR2 comprising the amino acid sequence represented by any one of SEQ ID NOs:4 and 6 to 10, and the like.

Examples of the gene recombinant antibody of the present invention includes a gene recombinant antibody in which CDR1, CDR2 and CDR3 of VH of the antibody comprise the amino acid sequences represented by SEQ ID NO:3, any one of SEQ ID NOs:4 and 6 to 10 and SEQ ID NO:5, respectively, and/or CDR1, CDR2 and CDR3 of VL of the antibody comprise the amino acid sequences represented by SEQ ID NOs: 11, 12 and 13, respectively. Specific examples include:

a gene recombinant antibody in which CDR1, CDR2 and CDR3 of VH of the antibody comprise the amino acid sequences represented by SEQ ID NOs:3, 4 and 5, respectively, and/or CDR1, CDR2 and CDR3 of VL of the antibody comprise the amino acid sequences represented by SEQ ID NOs:11, 12 and 13, respectively, a gene recombinant antibody in which CDR1, CDR2 and CDR3 of VH of the antibody comprise the amino acid sequences represented by SEQ ID NOs:3, 6 and 5, respectively, and/or CDR1, CDR2 and CDR3 of VL of the antibody comprise the amino acid sequences represented by SEQ ID NOs:11, 12 and 13, respectively, a gene recombinant antibody in which CDR1, CDR2 and CDR3 of VH of the antibody comprise the amino acid sequences represented by SEQ ID NOs:3, 7 and 5, respectively, and/or CDR1, CDR2 and CDR3 of VL of the antibody comprise the amino acid sequences represented by SEQ ID NOs:11, 12 and 13, respectively, a gene recombinant antibody in which CDR1, CDR2 and CDR3 of VH of the antibody comprise the amino acid sequences represented by SEQ ID NOs:3, 8 and 5, respectively, and/or CDR1, CDR2 and CDR3 of VL of the antibody comprise the amino acid sequences represented by SEQ ID NOs:11, 12 and 13, respectively, a gene recombinant antibody in which CDR1, CDR2 and CDR3 of VH of the antibody comprise the amino acid sequences represented by SEQ ID NOs:3, 9 and 5, respectively, and/or CDR1, CDR2 and CDR3 of VL of the antibody comprise the amino acid sequences represented by SEQ ID NOs:11, 12 and 13, respectively, a gene recombinant antibody in which CDR1, CDR2 and CDR3 of VH of the antibody comprise the amino acid sequences represented by SEQ ID NOs:3, 10 and 5, respectively, and/or CDR1, CDR2 and CDR3 of VL of the antibody comprise the amino acid sequences represented by SEQ ID NOs:11, 12 and 13, respectively, and the like.

A gene recombinant antibody in which CDR1, CDR2 and CDR3 of VH of the antibody comprise the amino acid sequences represented by SEQ ID NOs:3, 8 and 5, respectively, and/or CDR1, CDR2 and CDR3 of VL of the antibody comprise the amino acid sequences represented by SEQ ID NOs:11, 12 and 13, respectively, is preferred.

The gene recombinant antibody of the present invention includes antibodies prepared by gene recombination, such as a human chimeric antibody, a humanized antibody, a human antibody or an antibody fragment. The gene recombinant antibody which has characteristics of a monoclonal antibody such as low antigenicity and prolonged half life in blood is preferred as a therapeutic agent.

A human chimeric antibody is an antibody comprising VH and VL from a non-human animal, and CH and a light chain constant region (hereinafter referred to as "CL") from a human antibody.

The human chimeric antibody of the present invention can be produced as described below. Firstly, cDNAs encoding VH and VL are obtained from a hybridoma which produces a monoclonal antibody which specifically recognizes three-dimensional structure of an extracellular region of a polypeptide encoded by the PERP gene and binds to the extracellular region, and PCR is carried out with a mutation primer using the sequences as templates to thereby produce cDNAs encoding VH and VL having no consensus sequence of an N-linked sugar chain. The human chimeric antibody can be produced by inserting the produced cDNAs into an expression vector for animal cell having genes encoding CH and CL of a human antibody to construct a human chimeric antibody expression vector, and introducing the vector into an animal cell to express the antibody.

As the CH of the human chimeric antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of human chimeric antibody, any CL can be used, so long as it belongs to the hIg class, and those belonging to the κ class or λ class can be used.

The human chimeric antibody of the present invention specifically includes a human chimeric antibody wherein VH of the antibody comprises the amino acid sequence represented by any one of SEQ ID NOs:14 to 19, and/or VL of the antibody comprises the amino acid sequence represented by SEQ ID NO:20.

A humanized antibody is an antibody in which amino acid sequences of CDRs in VH and VL of an antibody from a non-human animal are grafted into appropriate positions of VH and VL of a human antibody, and is also called a CDR-grafted antibody, a reshaped-antibody or the like.

The humanized antibody of the present invention can be produced as described below. Firstly, amino acid sequences of VH and VL having no consensus sequence of an N-linked sugar chain are designed from amino acid sequences of CDRs in VH and VL of an antibody from a non-human animal which is produced by a hybridoma which produces a monoclonal antibody of a non-human animal which specifically recognizes three-dimensional structure of an extracellular region of a polypeptide encoded by the PERP gene and binds to the extracellular region, and cDNAs encoding variable regions in which the designed CDRs of VH and VL are grafted into FR of VH and VL of an optional human antibody are produced. The humanized antibody can be produced by inserting the produced cDNAs into an expression vector for animal cell having genes encoding CH and CL of a human antibody to construct a humanized antibody expression vector, and then introducing the expression vector into an animal cell to express the antibody.

The amino acid sequences of FRs of VH and VL of a human antibody may be any amino acid sequences, so long as they are amino acid sequences of FRs of VH and VL from a human antibody. For example, they includes amino acid sequences of FRs of VH and VL of human antibodies registered in database such as Protein Data Bank, common amino acid sequences of each subgroups of FRs of VH and VL of human antibodies described in *Sequences of Proteins of Immunological Interest*, US Dept. Health and Human Services (1991), and the like.

As the CH of a humanized antibody, any CH can be used, so long as it belongs to the hIg, and those of the hIgG class are preferred and any one of the subclasses belonging to the hIgG class, such as hIgG1, hIgG2, hIgG3 and hIgG4, can be used. As the CL of a humanized antibody, any CL can be used, so long as it belongs to the hIg class, and those belonging to the κ class or λ class can be used.

The humanized antibody of the present invention specifically include a humanized antibody wherein VH of the antibody comprises the amino acid sequence represented by any one of SEQ ID NOs:30 to 35 or an amino acid sequence in which at least one amino acid residue selected from Gly at position 27, Ser at position 30, Pro at position 41, Lys at position 44, Gly at position 45, Ile at position 49, Val at position 72 and Ala at position 97 is substituted with other amino acid residues in the amino acid sequence represented by any one of SEQ ID NOs:30 to 35, and/or VL of the antibody comprises the amino acid sequence represented by SEQ ID NO:36 or an amino acid sequence in which at least one amino acid residue selected from Gln at position 3, Thr at position 5, Tyr at position 35, Ala at position 42, Leu at position 46, Asp at position 69, Phe at position 70, Thr at position 71 and Leu at position 77 is substituted with other amino acid residues in the amino acid sequence represented by SEQ ID NO:36.

In the amino acid sequence in which at least one amino acid residue selected from Gly at position 27, Ser at position 30, Pro at position 41, Lys at position 44, Gly at position 45, Ile at position 49, Val at position 72 and Ala at position 97 is substituted with other amino acid residues in the amino acid sequence represented by one of SEQ ID NOs:30 to 35 in VH of the antibody, the number of the modification(s) to be introduced is not particularly limited. Preferred examples include a humanized antibody wherein VH of the antibody comprises an amino acid sequence in which Gly at position 27, Pro at position 41, Ile at position 49, Val at position 72 and Ala at position 97, more preferably Gly at position 27, Val at position 72 and Ala at position 97, are substituted with other amino acid residues in the amino acid sequence represented by any one of SEQ ID NOs:30 to 35.

In VH of the antibody, the amino acid sequence in which at least one amino acid residue selected from Gly at position 27, Ser at position 30, Pro at position 41, Lys at position 44, Gly at position 45, Ile at position 49, Val at position 72 and Ala at position 97 is substituted with other amino acid residues in the amino acid sequence represented by one of SEQ ID NOs:30 to 35 includes an amino acid sequence into which at least one modification is introduced into the amino acid sequence represented by any one of SEQ ID NOs:30 to 35, said modification being selected from substitutions of Gly at position 27 with Phe, Ser at position 30 with Thr, Pro at position 41 with Phe, Lys at position 44 with Asn, Gly at position 45 with Arg, Ile at position 49 with Met, Val at position 72 with Arg and Ala at position 97 with Thr.

The amino acid sequence which has eight amino acid residues modified, specifically includes an amino acid sequence having substitutions of Gly at position 27 with Phe, Ser at position 30 with Thr, Pro at position 41 with Phe, Lys at position 44 with Asn, Gly at position 45 with Arg, Ile at position 49 with Met, Val at position 72 with Arg and Ala at position 97 with Thr in the amino acid sequence represented by any one of SEQ ID NOs:30 to 35.

The amino acid sequence which has seven amino acid residues modified, specifically includes:

an amino acid sequence having substitutions of Ser at position 30 with Thr, Pro at position 41 with Phe, Lys at position 44 with Asn, Gly at position 45 with Arg, Ile at position 49 with Met, Val at position 72 with Arg and Ala at position 97 with Thr, an amino acid sequence having substitutions of Gly at position 27 with Phe, Pro at position 41 with Phe, Lys at position 44 with Asn, Gly at position 45 with Arg, Ile at position 49 with Met, Val at position 72 with Arg and Ala at position 97 with Thr, an amino acid sequence having substitutions of Gly at position 27 with Phe, Ser at position 30 with Thr, Pro at position 41 with Phe, Lys at position 44 with Asn, Gly at position 45 with Arg, Val at position 72 with Arg and Ala at position 97 with Thr, an amino acid sequence having substitutions of Gly at position 27 with Phe, Ser at position 30 with Thr, Pro at position 41 with Phe, Gly at position 45 with Arg, Ile at position 49 with Met, Val at position 72 with Arg and Ala at position 97 with Thr, an amino acid sequence having substitutions of Gly at position 27 with Phe, Ser at position 30 with Thr, Lys at position 44 with Asn, Gly at position 45 with Arg, Ile at position 49 with Met, Val at position 72 with Arg and Ala at position 97 with Thr, and an amino acid sequence having substitutions of Gly at position 27 with Phe, Ser at position 30 with Thr, Pro at position 41 with Phe, Lys at position 44 with Asn, Ile at position 49 with Met, Val at position 72 with Arg and Ala at position 97 with Thr, in the amino acid sequence represented by any one of SEQ ID NOs:30 to 35,
and the like.

The amino acid sequence which has six amino acid residues modified, specifically includes:

an amino acid sequence having substitutions of Gly at position 27 with Phe, Pro at position 41 with Phe, Lys at position 44 with Asn, Gly at position 45 with Arg, Val at position 72 with Arg and Ala at position 97 with Thr, an amino acid sequence having substitutions of Gly at position 27 with Phe, Pro at position 41 with Phe, Gly at position 45 with Arg, Ile at position 49 with Met, Val at position 72 with Arg and Ala at position 97 with Thr, an amino acid sequence having substitutions of Gly at position 27 with Phe, Lys at position 44 with Asn, Gly at position 45 with Arg, Ile at position 49 with Met, Val at position 72 with Arg and Ala at position 97 with Thr, an amino acid sequence having substitutions of Gly at position 27 with Phe, Pro at position 41 with Phe, Lys at position 44 with Asn, Ile at position 49 with Met, Val at position 72 with Arg and Ala at position 97 with Thr, an amino acid sequence having substitutions of Ser at position 30 with Thr, Pro at position 41 with Phe, Lys at position 44 with Asn, Gly at position 45 with Arg, Val at position 72 with Arg and Ala at position 97 with Thr, an amino acid sequence having substitutions of Ser at position 30 with Thr, Pro at position 41 with Phe, Gly at position 45 with Arg, Ile at position 49 with Met, Val at position 72 with Arg and Ala at position 97 with Thr, an amino acid sequence having substitutions of Ser at position 30 with Thr, Lys at position 44 with Asn, Gly at position 45 with Arg, Ile at position 49 with Met, Val at position 72 with Arg and Ala at position 97 with Thr, an amino acid sequence having substitutions of Ser at position 30 with Thr, Pro at position 41 with Phe, Lys at position 44 with Asn, Ile at position 49 with Met, Val at position 72 with Arg and Ala at position 97 with Thr, an amino acid sequence having substitutions of Gly at position 27 with Phe, Ser at position 30 with Thr, Pro at position 41 with Phe, Lys at position 44 with Asn, Val at position 72 with Arg and Ala at position 97 with Thr, an amino acid sequence having substitutions of Gly at position 27 with Phe, Ser at position 30 with Thr, Pro at position 41 with Phe, Gly at position 45 with Arg, Val at position 72 with Arg and Ala at position 97 with Thr, an amino acid sequence having substitutions of Gly at position 27 with Phe, Ser at position 30 with Thr, Pro at position 41 with Phe, Ile at position 49 with Met, Val at position 72 with Arg and Ala at position 97 with Thr, an amino acid sequence having substitutions of Gly at position 27 with Phe, Ser at position 30 with Thr, Lys at position 44 with Asn, Gly at position 45 with Arg, Val at position 72 with Arg and Ala at position 97 with Thr, an amino acid sequence having substitutions of Gly at position 27 with Phe, Ser at position 30 with Thr, Lys at position 44 with Asn, Ile at position 49 with Met, Val at position 72 with Arg and Ala at position 97 with Thr, and an amino acid sequence having substitutions of Gly at position 27 with Phe, Ser at position 30 with Thr, Gly at position 45 with Arg, Ile at position 49 with Met, Val at position 72 with Arg and Ala at position 97 with Thr, in the amino acid sequence represented by any one of SEQ ID NOs:30 to 35,
and the like.

The amino acid sequence which has five amino acid residues modified, specifically includes:

an amino acid sequence having substitutions of Gly at position 27 with Phe, Pro at position 41 with Phe, Lys at position 44 with Asn, Val at position 72 with Arg and Ala at position 97 with Thr, an amino acid sequence having substitutions of Gly at position 27 with Phe, Pro at position 41 with Phe, Gly at position 45 with Arg, Val at position 72 with Arg and Ala at position 97 with Thr, an amino acid sequence having substitutions of Gly at position 27 with Phe, Pro at position 41 with Phe, Ile at position 49 with Met, Val at position 72 with Arg and Ala at position 97 with Thr, an amino acid sequence having substitutions of Gly at position 27 with Phe, Lys at position 44 with Asn, Gly at position 45 with Arg, Val at position 72 with Arg and Ala at position 97 with Thr, an amino acid sequence having substitutions of Gly at position 27 with Phe, Lys at position 44 with Asn, Ile at position 49 with Met, Val at position 72 with Arg and Ala at position 97 with Thr, an amino acid sequence having substitutions of Gly at position 27 with Phe, Gly at position 45 with Arg, Ile at position 49 with Met, Val at position 72 with Arg and Ala at position 97 with Thr, an amino acid sequence having substitutions of Ser at position 30 with Thr, Pro at position 41 with Phe, Lys at position 44 with Asn, Val at position 72 with Arg and Ala at position 97 with Thr, an amino acid sequence having substitutions of Ser at position 30 with Thr, Pro at position 41 with Phe, Gly at position 45 with Arg, Val at position 72 with Arg and Ala at position 97 with Thr, an amino acid sequence having substitutions of Ser at position 30 with Thr, Pro at position 41 with Phe, Ile at position 49 with Met, Val at position 72 with Arg and Ala at position 97 with Thr, an amino acid sequence having substitutions of Ser at position 30 with Thr, Lys at position 44 with Asn, Gly at position 45 with Arg, Val at position 72 with Arg and Ala at position 97 with Thr, an amino acid sequence having substitutions of Ser at position 30 with Thr, Lys at position 44 with Asn, Ile at position 49 with Met, Val at position 72 with Arg and Ala at position 97 with Thr, an amino acid sequence having substitutions of Ser at position 30 with Thr, Gly at position 45 with Arg, Ile at position 49 with Met, Val at position 72 with Arg and Ala at position 97 with Thr, an amino acid sequence having substitutions of Gly at position 27 with Phe, Ser at position 30 with Thr, Pro at position 41 with Phe, Val at position 72 with Arg and Ala at position 97 with Thr, an amino acid sequence having substitutions of Gly at position 27 with Phe, Ser at position 30 with Thr, Lys at position 44 with Asn, Val at position 72 with Arg and Ala at position 97 with Thr, an amino acid sequence having substitutions of Gly at position 27 with Phe, Ser at position 30 with Thr, Gly at position 45 with Arg, Val at position 72 with Arg and Ala at position 97 with Thr, and an amino acid sequence having substitutions of Gly at position 27 with Phe, Ser at position 30 with Thr, Ile at position 49 with Met, Val at position 72 with Arg and Ala at position 97 with Thr, in the amino acid sequence represented by any one of SEQ ID NOs:30 to 35, and the like.

The amino acid sequence which has four amino acid residues modified, specifically includes:

an amino acid sequence having substitutions of Gly at position 27 with Phe, Pro at position 41 with Phe, Val at position 72 with Arg and Ala at position 97 with Thr, an amino acid sequence having substitutions of Gly at position 27 with Phe, Lys at position 44 with Asn, Val at position 72 with Arg and Ala at position 97 with Thr, an amino acid sequence having substitutions of Gly at position 27 with Phe, Gly at position 45 with Arg, Val at position 72 with Arg and Ala at position 97 with Thr, an amino acid sequence having substitutions of Gly at position 27 with Phe, Ile at position 49 with Met, Val at position 72 with Arg and Ala at position 97 with Thr, an amino acid sequence having substitutions of Ser at position 30 with Thr, Pro at position 41 with Phe, Val at position 72 with Arg and Ala at position 97 with Thr, an amino acid sequence having substitutions of Ser at position 30 with Thr, Lys at position 44 with Asn, Val at position 72 with Arg and Ala at position 97 with Thr, an amino acid sequence having substitutions of Ser at position 30 with Thr, Gly at position 45 with Arg, Val at position 72 with Arg and Ala at position 97 with Thr, an amino acid sequence having substitutions of Ser at position 30 with Thr, Ile at position 49 with Met, Val at position 72 with Arg and Ala at position 97 with Thr, an amino acid sequence having substitutions of Gly at position 27 with Phe, Ser at position 30 with Thr, Val at position 72 with Arg and Ala at position 97 with Thr, an amino acid sequence having substitutions of Gly at position 27 with Phe, Ser at position 30 with Thr, Pro at position 41 with Phe and Ala at position 97 with Thr, and an amino acid sequence having substitutions of Pro at position 41 with Phe, Lys at position 44 with Asn, Gly at position 45 with Arg and Ile at position 49 with Met, and in the amino acid sequence represented by any one of SEQ ID NOs:30 to 35, and the like.

The amino acid sequence which has three amino acid residues modified, specifically includes:

an amino acid sequence having substitutions of Gly at position 27 with Phe, Val at position 72 with Arg and Ala at position 97 with Thr, an amino acid sequence having substitutions of Ser at position 30 with Thr, Val at position 72 with Arg and Ala at position 97 with Thr, and an amino acid sequence having substitutions of Gly at position 27 with Phe, Pro at position 41 with Phe and Ala at position 97 with Thr, in the amino acid sequence represented by any one of SEQ ID NOs:30 to 35, and the like.

The amino acid sequence which has two amino acid modified, specifically includes:

an amino acid sequence having substitutions of Val at position 72 with Arg and Ala at position 97 with Thr, and an amino acid sequence having substitutions of Gly at position 27 with Phe and Ser at position 30 with Thr, in the amino acid sequence represented by any one of SEQ ID NOs:30 to 35, and the like.

The amino acid sequence which has one amino acid residue modified, specifically includes:

an amino acid sequence having substitutions of Gly at position 27 with Phe, an amino acid sequence having substitutions of Ser at position 30 with Thr, an amino acid sequence having substitutions of Pro at position 41 with Phe, an amino acid sequence having substitutions of Lys at position 44 with Asn, an amino acid sequence having substitutions of Gly at position 45 with Arg, an amino acid sequence having substitutions of Ile at position 49 with Met, an amino acid sequence having substitutions of Val at position 72 with Arg, and an amino acid sequence having substitutions of Ala at position 97 with Thr, in the amino acid sequence represented by any one of SEQ ID NOs:30 to 35.

In the amino acid sequence in which at least one amino acid residue selected from Gln at position 3, Thr at position 5, Tyr at position 35, Ala at position 42, Leu at position 46, Phe at position 70, Thr at position 71 and Leu at position 77 is substituted with other amino acid residues in the amino acid sequence represented by SEQ ID NO:36 in VL of the antibody, the number of the modification(s) to be introduced is not particularly limited. Preferred examples include an amino acid sequence in which Gln at position 3, Thr at position 5, Tyr at position 35, Ala at position 42, Leu at position 46, Phe at position 70, and Leu at position 77, more preferably Leu at position 46, Phe at position 70, and Leu at position 77, and most preferably Leu at position 46 and Phe at position 70, are substituted with other amino acid residues.

In VL of the antibody, the amino acid sequence in which at least one amino acid residue selected from Gln at position 3, Thr at position 5, Tyr at position 35, Ala at position 42, Leu at position 46, Asp at position 69, Phe at position 70, Thr at position 71, and Leu at position 77 is substituted with other amino acid residues in the amino acid sequence represented by SEQ ID NO:36 includes an amino acid sequence into which at least one modification is introduced into the amino acid sequence represented by SEQ ID NO:36, said modification being selected from substitutions of Gln at position 3 with Val, Thr at position 5 with Ile, Tyr at position 35 with Phe, Ala at position 42 with Ser, Leu at position 46 with Trp, Asp at position 69 with Ser, Phe at position 70 with Tyr, Thr at position 71 with Ser and Leu at position 77 with Met.

The amino acid sequence which has nine amino acid residues modified, specifically includes an amino acid sequence having substitutions of Gln at position 3 with Val, Thr at position 5 with Ile, Tyr at position 35 with Phe, Ala at position 42 with Ser, Leu at position 46 with Trp, Asp at position 69 with Ser, Phe at position 70 with Tyr, Thr at position 71 with Ser and Leu at position 77 with Met in the amino acid sequence represented by SEQ ID NO:36, and the like.

The amino acid sequence which has eight amino acid residues modified, specifically includes:

an amino acid sequence having substitutions of Thr at position 5 with Ile, Tyr at position 35 with Phe, Ala at position 42 with Ser, Leu at position 46 with Trp, Asp at position 69 with Ser, Phe at position 70 with Tyr, Thr at position 71 with Ser and Leu at position 77 with Met, an amino acid sequence having substitutions of Gln at position 3 with Val, Tyr at position 35 with Phe, Ala at position 42 with Ser, Leu at position 46 with Trp, Asp at position 69 with Ser, Phe at position 70 with Tyr, Thr at position 71 with Ser and Leu at position 77 with Met, an amino acid sequence having substitutions of Gln at position 3 with Val, Thr at position 5 with Ile, Ala at position 42 with Ser, Leu at position 46 with Trp, Asp at position 69 with Ser, Phe at position 70 with Tyr, Thr at position 71 with Ser and Leu at position 77 with Met, an amino acid sequence having substitutions of Gln at position 3 with Val, Thr at position 5 with Ile, Tyr at position 35 with Phe, Leu at position 46 with Trp, Asp at position 69 with Ser, Phe at position 70 with Tyr, Thr at position 71 with Ser and Leu at position 77 with Met, an amino acid sequence having substitutions of Gln at position 3 with Val, Thr at position 5 with Ile, Tyr at position 35 with Phe, Ala at position 42 with Ser, Asp at position 69 with Ser, Phe at position 70 with Tyr, Thr at position 71 with Ser and Leu at position 77 with Met, an amino acid sequence having substitutions of Gln at position 3 with Val, Thr at position 5 with Ile, Tyr at position 35 with Phe, Ala at position 42 with Ser, Leu at position 46 with Trp, Phe at position 70 with Tyr, Thr at position 71 with Ser and Leu at position 77 with Met, an amino acid sequence having substitutions of Gln at position 3 with Val, Thr at position 5 with Ile, Tyr at position 35 with Phe, Ala at position 42 with Ser, Leu at position 46 with Trp, Asp at position 69 with Ser, Thr at position 71 with Ser and Leu at position 77 with Met, an amino acid sequence having substitutions of Gln at position 3 with Val, Thr at position 5 with Ile, Tyr at position 35 with Phe, Ala at position 42 with Ser, Leu at position 46 with Trp, Asp at position 69 with Ser, Phe at position 70 with Tyr and Leu at position 77 with Met, and an amino acid sequence having substitutions of Gln at position 3 with Val, Thr at position 5 with Ile, Tyr at position 35 with Phe, Ala at position 42 with Ser, Leu at position 46 with Trp, Asp at position 69 with Ser, Phe at position 70 with Tyr and Thr at position 71 with Ser, in the amino acid sequence represented by SEQ ID NO:36, and the like.

The amino acid sequence which has seven amino acid residues modified, specifically includes an amino acid sequence having substitutions of Gln at position 3 with Val, Thr at position 5 with Ile, Tyr at position 35 with Phe, Ala at position 42 with Ser, Leu at position 46 with Trp, Phe at position 70 with Tyr and Leu at position 77 with Met in the amino acid sequence represented by SEQ ID NO:36, and the like.

The amino acid sequence which has six amino acid residues modified, specifically includes:

an amino acid sequence having substitutions of Gln at position 3 with Val, Thr at position 5 with Ile, Tyr at position 35 with Phe, Ala at position 42 with Ser, Leu at position 46 with Trp and Phe at position 70 with Tyr, an amino acid sequence having substitutions of Gln at position 3 with Val, Tyr at position 35 with Phe, Ala at position 42 with Ser, Leu at position 46 with Trp, Phe at position 70 with Tyr and Leu at position 77 with Met, an amino acid sequence having substitutions of Thr at position 5 with Ile, Tyr at position 35 with Phe, Ala at position 42 with Ser, Leu at position 46 with Trp, Phe at position 70 with Tyr and Leu at position 77 with Met, an amino acid sequence having substitutions of Gln at position 3 with Val, Thr at position 5 with Ile, Tyr at position 35 with Phe, Leu at position 46 with Trp, Phe at position 70 with Tyr and Leu at position 77 with Met, and an amino acid sequence having substitutions of Gln at position 3 with Val, Thr at position 5 with Ile, Ala at position 42 with Ser, Leu at position 46 with Trp, Phe at position 70 with Tyr and Leu at position 77 with Met, in the amino acid sequence represented by SEQ ID NO:36, and the like.

The amino acid sequence which has five amino acid residues modified, specifically includes:

an amino acid sequence having substitutions of Gln at position 3 with Val, Tyr at position 35 with Phe, Ala at position 42 with Ser, Leu at position 46 with Trp and Phe at position 70 with Tyr, an amino acid sequence having substitutions of Thr at position 5 with Ile, Tyr at position 35 with Phe, Ala at position 42 with Ser, Leu at position 46 with Trp and Phe at position 70 with Tyr, an amino acid sequence having substitutions of Tyr at position 35 with Phe, Ala at position 42 with Ser, Leu at position 46 with Trp, Phe at position 70 with Tyr and Leu at position 77 with Met, an amino acid sequence having substitutions of Gln at position 3 with Val, Thr at position 5 with Ile, Tyr at position 35 with Phe, Leu at position 46 with Trp and Phe at position 70 with Tyr, an amino acid sequence having substitutions of Gln at position 3 with Val, Thr at position 5 with Ile, Ala at position 42 with Ser, Leu at position 46 with Trp and Phe at position 70 with Tyr, an amino acid sequence having substitutions of Gln at position 3 with Val, Tyr at position 35 with Phe, Leu at position 46 with Trp, Phe at position 70 with Tyr and Leu at position 77 with Met, an amino acid sequence having substitutions of Gln at position 3 with Val, Ala at position 42 with Ser, Leu at position 46 with Trp, Phe at position 70 with Tyr and Leu at position 77 with Met, an amino acid sequence having substitutions of Thr at position 5 with Ile, Tyr at position 35 with Phe, Leu at position 46 with Trp, Phe at position 70 with Tyr and Leu at position 77 with Met, an amino acid sequence having substitutions of Thr at position 5 with Ile, Ala at position 42 with Ser, Leu at position 46 with Trp, Phe at position 70 with Tyr and Leu at position 77 with Met, an amino acid sequence having substitutions of Gln at position 3 with Val, Thr at position 5 with Ile, Leu at position 46 with Trp, Phe at position 70 with Tyr and Leu at position 77 with Met, and an amino acid sequence having substitutions of Ala at position 42 with Ser, Leu at position 46 with Trp, Asp at position 69 with Ser, Phe at position 70 with Tyr and Thr at position 71 with Ser, in the amino acid sequence represented by SEQ ID NO:36, and the like.

The amino acid sequence which has four amino acids residues modified, specifically includes:

an amino acid sequence having substitutions of Gln at position 3 with Val, Tyr at position 35 with Phe, Leu at position 46 with Trp and Phe at position 70 with Tyr, an amino acid sequence having substitutions of Gln at position 3 with Val, Ala at position 42 with Ser, Leu at position 46 with Trp and Phe at position 70 with Tyr, an amino acid sequence having substitutions of Thr at position 5 with Ile, Tyr at position 35 with Phe, Leu at position 46 with Trp and Phe at position 70 with Tyr, an amino acid sequence having substitutions of Thr at position 5 with Ile, Ala at position 42 with Ser, Leu at position 46 with Trp and Phe at position 70 with Tyr, an amino acid sequence having substitutions of Tyr at position 35 with Phe, Leu at position 46 with Trp, Phe at position 70 with Tyr and Leu at position 77 with Met, an amino acid sequence having substitutions of Ala at position 42 with Ser, Leu at position 46 with Trp, Phe at position 70 with Tyr and Leu at position 77 with Met, an amino acid sequence having substitutions of Gln at position 3 with Val, Thr at position 5 with Ile, Leu at position 46 with Trp and Phe at position 70 with Tyr, an amino acid sequence having substitutions of Gln at position 3 with Val, Leu at position 46 with Trp, Phe at position 70 with Tyr and Leu at position 77 with Met, and an amino acid sequence having substitutions of Thr at position 5 with Ile, Leu at position 46 with Trp, Phe at position 70 with Tyr and Leu at position 77 with Met, in the amino acid sequence represented by SEQ ID NO:36, and the like.

The amino acid sequence which has three amino acid residues modified, specifically includes:

an amino acid sequence having substitutions of Gln at position 3 with Val, Leu at position 46 with Trp and Phe at position 70 with Tyr, an amino acid sequence having substitutions of Thr at position 5 with Ile, Leu at position 46 with Trp and Phe at position 70 with Tyr, an amino acid sequence having substitutions of Leu at position 46 with Trp, Phe at position 70 with Tyr and Leu at position 77 with Met, an amino acid sequence having substitutions of Tyr at position 35 with Phe, Ala at position 42 with Ser and Leu at position 46 with Trp, and an amino acid sequence having substitutions of Ala at position 42 with Ser, Leu at position 46 with Trp and Phe at position 70 with Tyr in the amino acid sequence represented by SEQ ID NO:36, and the like.

The amino acid sequence which has two amino acid residues, modified, specifically includes:

an amino acid sequence having substitutions of Leu at position 46 with Trp and Phe at position 70 with Tyr, an amino acid sequence having substitutions of Gln at position 3 with Val and Thr at position 5 with Ile, and an amino acid sequence having substitutions of Phe at position 70 with Tyr, and Leu at position 77 with Met, in the amino acid sequence represented by SEQ ID NO:36, and the like.

The amino acid sequence which has one amino acid residue modified, specifically includes:

an amino acid sequence having substitution of Gln at position 3 with Val, an amino acid sequence having substitution of Thr at position 5 with Ile, an amino acid sequence having substitution of Tyr at position 35 with Phe, an amino acid sequence having substitution of Ala at position 42 with Ser, an amino acid sequence having substitution of Leu at position 46 with Trp, an amino acid sequence having substitution of Asp at position 69 with Ser, an amino acid sequence having substitution of Phe at position 70 with Tyr, an amino acid sequence having substitution of Thr at position 71 with Ser, and an amino acid sequence having substitution of Leu at position 77 with Met, and the like.

VH of the humanized antibody of the present invention specifically includes the amino acid sequence represented by any of SEQ ID NOs:51 to 56, preferably the amino acid sequence represented by SEQ ID NOs:51, 53, 55 and 56, and more preferably the amino acid sequence represented by SEQ ID NO:53.

VL of the humanized antibody of the present invention specifically includes the amino acid sequence represented by any of SEQ ID NOs:58 to 63, preferably the amino acid sequence represented by SEQ ID NOs:58, 59, 60, 62 and 63, and more preferably the amino acid sequence represented by SEQ ID NO:62.

The humanized antibody of the present invention includes a humanized antibody comprising VH and VL of the above amino acid sequences, such as a humanized antibody wherein VH and VL comprise the amino acid sequence represented by SEQ ID NOs:53 and 59, respectively, a humanized antibody wherein VH and VL comprise the amino acid sequence represented by SEQ ID NOs:53 and 60, respectively, a humanized antibody wherein VH and VL comprise the amino acid sequence represented by SEQ ID NOs:55 and 62, respectively, a humanized antibody wherein VH and VL comprise the amino acid sequence represented by SEQ ID NOs:51 and 58, respectively, a humanized antibody wherein VH and VL comprise the amino acid sequence represented by SEQ ID NOs:53 and 58, respectively, a humanized antibody wherein VH and VL comprise the amino acid sequence represented by SEQ ID NOs:53 and 63, respectively, a humanized antibody wherein VH and VL comprise the amino acid sequence represented by SEQ ID NOs:56 and 62, respectively, a humanized antibody wherein VH and VL comprise the amino acid sequence represented by SEQ ID NOs:53 and 62, respectively. More preferred examples include:

a humanized antibody wherein VH and VL comprise the amino acid sequence represented by SEQ ID NOs:55 and 62, respectively, a humanized antibody wherein VH and VL comprise the amino acid sequence represented by SEQ ID NOs:51 and 58, respectively, a humanized antibody wherein VH and VL comprise the amino acid sequence represented by SEQ ID NOs:53 and 58, respectively, a humanized antibody wherein VH and VL comprise the amino acid sequence represented by SEQ ID NOs:53 and 63, respectively, a humanized antibody wherein VH and VL comprise the amino acid sequence represented by SEQ ID NOs:56 and 62, respectively, and a humanized antibody wherein VH and VL comprise the amino acid sequence represented by SEQ ID NOs:53 and 62, respectively.

Also, the gene recombinant antibody of the present invention includes a gene recombinant antibody which binds to an epitope recognized by a monoclonal antibody produced by a hybridoma KM3411 (FERM BP-8643).

The antibody fragment of the present invention includes Fab, F(ab')$_2$, Fab', scFv, diabody, dsFv, a peptide comprising CDR, and the like.

An Fab is an antibody fragment having a molecular weight of about 50,000 and having antigen binding activity, in which about a half of the N-terminal side of H chain and the entire L chain, among fragments obtained by treating IgG with a protease, papain (cleaving an amino acid residue at the 224th position of the H chain), are bound together through a disulfide bond.

The Fab of the present invention can be produced by obtaining cDNAs encoding VH and VL of the gene recombinant antibody of the present invention which has no consensus sequence of an N-linked sugar chain in a variable region, specifically recognizes three-dimensional structure of an extracellular region of a polypeptide encoded by the PERP gene and binds to the extracellular region, inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and having antigen binding activity and comprising two Fab regions which are bound in the hinge position obtained by digesting the lower part of two disulfide bonds in the hinge region of IgG, with enzyme, pepsin.

The F(ab')$_2$ of the present invention can be prepared by binding Fab' described below via a thioether bond or a disulfide bond.

An Fab' is an antibody fragment having a molecular weight of about 50,000 and having antigen binding activity, which is obtained by cleaving a disulfide bond at the hinge region of the above F(ab')$_2$.

The Fab' of the present invention can be produced by obtaining cDNAs encoding VH and VL of the gene recombinant antibody of the present invention which has no consensus sequence of an N-linked sugar chain in a variable region, specifically recognizes three-dimensional structure of an extracellular region of a polypeptide encoded by the PERP gene and binds to the extracellular region, inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P") and is an antibody fragment having antigen binding activity.

The scFv of the present invention can be produced by obtaining cDNAs encoding VH and VL of the gene recombinant antibody of the present invention which has no consensus sequence of an N-linked sugar chain in a variable region, specifically recognizes three-dimensional structure of an extracellular region of a polypeptide encoded by the PERP gene and binds to the extracellular region, constructing DNA encoding scFv, inserting DNA encoding scFv of the antibody into an expression vector for prokaryote or an expression vector for eukaryote, and then introducing the expression vector into a prokaryote or eukaryote to express the scFv.

A diabody is an antibody fragment where scFv is dimerized, and has divalent antigen binding activity. In the divalent antigen binding activity, two antigens may be the same or different.

The diabody of the present invention can be produced by constructing DNA encoding scFv so that the length of the amino acid sequence of P is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. (*Protein Engineering*, 7, 697 (1994)).

The dsFv of the present invention can be produced by obtaining cDNAs encoding VH and VL of the gene recombinant antibody of the present invention which has no consensus sequence of an N-linked sugar chain in a variable region, specifically recognizes three-dimensional structure of an extracellular region of a polypeptide encoded by the PERP gene and binds to the extracellular region, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one region or more of CDRs of VH or VL. Peptide comprising plural CDRs can be bound directly or via an appropriate peptide linker.

The peptide comprising CDR of the present invention can be produced by constructing DNA encoding CDRs of VH and VL of the gene recombinant antibody of the present invention which has no consensus sequence of an N-linked sugar chain in a variable region, specifically recognizes three-dimensional structure of an extracellular region of a polypeptide encoded by the PERP gene and binds to the extracellular region, inserting the DNA into an expression vector for prokaryote or an expression vector for eukaryote, and then introducing the expression vector into a prokaryote or eukaryote to express the peptide.

The peptide comprising CDR can also be produced by a chemical synthesis method such as an Fmoc method (fluorenylmethoxycarbonyl method) or a tBoc method (t-butyloxycarbonyl method), or the like.

The gene recombinant antibody of the present invention includes a fusion antibody in which a radioisotope, an agent having low molecular weight, an agent having high molecular weight, a protein or the like is chemically or genetically conjugated to the gene recombinant antibody of the present invention which has no consensus sequence of an N-linked sugar chain in a variable region, specifically recognizes three-dimensional structure of an extracellular region of a polypeptide encoded by the PERP gene and binds to the extracellular region, or the antibody fragment.

The fusion antibody of the present invention can be produced by chemically conjugating a radioisotope, an agent having low molecular weight, an agent having high molecular weight, a protein or the like to the N-terminal side or C-terminal side of an H chain or an L chain of the gene recombinant antibody of the present invention which has no consensus sequence of an N-linked sugar chain in a variable region, specifically recognizes three-dimensional structure of an extracellular region of a polypeptide encoded by the PERP gene and binds to the extracellular region or the antibody fragment, an appropriate substituent or side chain of the antibody or the antibody fragment, a sugar chain in the antibody or the antibody fragment or the like [*Antibody Engineering Handbook*, edited by Osamu Kanemitsu, published by Chijin Shokan (1994)].

Also, the fusion antibody can be produced by linking a DNA encoding the gene recombinant antibody which has no consensus sequence of an N-linked sugar chain in a variable region, specifically recognizes three-dimensional structure of an extracellular region of a polypeptide encoded by the PERP gene and binds to the extracellular region or the antibody fragment to other DNAs encoding a protein to be bound, inserting the DNA into a vector for expression, introducing the expression vector into an appropriate host cell, and expressing the fusion antibody.

Examples of the radioisotope include $^{131}I$, $^{125}I$ and the like, and they can be conjugated to antibodies by, e.g., a chloramine T method.

The agent having a low molecular weight includes anticancer agents such as alkylating agents (e.g., nitrogen mustard, cyclophosphamide, etc.), metabolic antagonists (e.g., 5-fluorouracil, methotrexate, etc.), antibiotics (e.g., daunomycin, bleomycin, mitomycin C, daunorubicin, doxorubicin, etc.), plant alkaloids (e.g., vincristine, vinblastine, vindesine, etc.), hormone agents (e.g., tamoxifen, dexamethasone, etc.), and the like [*Clinical Oncology*, edited by Japanese Society of Clinical Oncology, published by Cancer and Chemotherapy (1996))]; anti-inflammatory agents such as steroid agents (e.g., hydrocortisone, prednisone, etc.), non-steroidal agents (e.g., aspirin, indometacin, etc.), immunomodulators (e.g., aurothiomalate, penicillamine, etc.), immunosuppressing agents (e.g., cyclophosphamide, azathioprine, etc.), antihistaminic agents (e.g., chlorpheniramine maleate, clemastine, etc.), and the like [*Inflammation and Anti-inflammatory Therapy*, Ishiyaku Shuppan (1982)]; and the like. Examples of the method for conjugating daunomycin to an antibody include a method in which daunomycin and an amino group of an antibody are conjugated via glutaraldehyde, a method in which an amino group of daunomycin and a carboxyl group of an antibody are conjugated via a water-soluble carbodiimide, and the like.

The agent having high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropylmethacrylamide, and the like. By binding these compounds having high molecular weight to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [*Bioconjugate Drug*, Hirokawa Shoten (1993)]. For example, the method for binding PEG to an antibody includes a method in which an antibody is allowed to react with a PEG-modifying reagent [*Bioconjugate Drug*, Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The protein includes cytokine which activates immunocompetent cells, such as human interleukin 2, human granulocyte macrophage colony-stimulating factor, human macrophage colony-stimulating factor, human interleukin 12, and the like. Also, in order to damage cancer cells directly, a toxin such as ricin, diphtheria toxin and the like, can be used. For example, a fusion antibody with a protein can be produced by linking a cDNA encoding an antibody or antibody fragment to other cDNAs encoding the protein, constructing DNA encoding the fusion antibody, inserting the DNA into an expression vector for prokaryote or an expression vector for eukaryote, and then introducing it into a prokaryote or eukaryote to express the fusion antibody.

When the fusion protein is used in a detection method, a quantitative determination method, a detecting agent, a quantitatively determining agent or a diagnosing agent, a label used in usual immunological detection or immunoassay can be used as an agent. The label includes enzymes such as alkaline phosphatase, peroxydase and luciferase, luminescent materials such as acridinium ester and rofin, fluorescent materials such as fluorescein isothiocyanate (FITC) and RITC, and the like.

The production process of the gene recombinant antibody of the present invention is explained below in detail.

1. Production of Anti-PERP Monoclonal Antibody which Specifically Recognizes Three-Dimensional Structure of an Extracellular Region of a Polypeptide Encoded by the PERP Gene and Binds to the Extracellular Region, Produced by Hybridoma (1) Preparation of Antigen The polypeptide used in the present invention can be produced, for example, by expressing a DNA encoding the polypeptide in a host cell using a method described in *Molecular Cloning, A Laboratory Manual*, Second Edition, Cold Spring Harbor Laboratory Press (1989), *Current Protocols in Molecular Biology*, John Wiley & Sons (1987-1997) or the like as follows.

Firstly, a recombinant vector is produced by inserting a full length cDNA containing cDNA encoding the polypeptide into downstream of a promoter of an appropriate expression vector. At this time, if necessary, a DNA fragment having an appropriate length containing a region encoding the polypeptide based on the full length cDNA may be prepared, and the DNA fragment may be used instead of the above full length cDNA. Next, a transformant producing the polypeptide can be obtained by introducing the recombinant vector into a host cell suitable for the expression vector.

The host cell can be any cell so long as it can express the gene of interest, and includes *Escherichia coli*, an animal cell and the like.

The expression vector includes vectors which can replicate autonomously in the host cell to be used or vectors which can be integrated into a chromosome comprising an appropriate promoter at such a position that the DNA encoding the polypeptide can be transcribed.

When a procaryote such as *Escherichia coli* is used as the host cell, it is preferred that the recombinant vector is autonomously replicable in the procaryote and contains a promoter, a ribosome binding sequence, the DNA used in the present invention and a transcription termination sequence. The recombinant vector may further comprise a gene regulating the promoter.

The expression vector includes, for example, pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 *[Agricultural Biological Chemistry*, 48, 669 (1984)], pLSA1 *[Agric. Biol. Chem.*, 53, 277 (1989)], pGEL1 *[Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. No. 4,686,191, U.S. Pat. No. 4,939,094, U.S. Pat. No. 5,160,735), pSupex, pUB110, pTP5, pC194, pEG400 *[J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a promoter in which two Ptrp are linked in tandem, tac promoter, lacT7 promoter and letI promoter, can be used.

Also, the above recombinant vector is preferably a plasmid in which the space between Shine-Dalgarno sequence, which is the ribosome binding sequence, and the initiation codon is adjusted to an appropriate distance (for example, 6 to 18 nucleotides). In the nucleotide sequence of DNA encoding the polypeptide used in the present invention, nucleotides can be arranged so as to obtain a suitable codon for expression in the host so that the producing ratio of the polypeptide of interest can be improved. Furthermore, the transcription termination sequence is not essential to express a gene in the above recombinant vector. However, it is preferred to arrange a transcription terminating sequence immediately downstream of the structural gene.

The procaryotes used for the host cells include procaryotes belonging to the genera *Escherichia*, and examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49 and the like.

Any introduction method of the recombinant vector can be used, so long as it is a method for introducing DNA into the above-described host cell, and examples include a method using a calcium ion described in *Proc. Natl. Acad. Sci. USA*, 69, 2110 (1972), *Gene*, 17, 107 (1982), *Molecular & General Genetics*, 168, 111 (1979) and the like.

When the polypeptide used in the present invention is produced in *Escherichia coli*, the polypeptide can be expressed, depending on the kind of the vector, as a soluble-type in the cytoplasm, as insoluble granules in the cytoplasm or as a soluble-type in periplasmic space.

When an animal cell is used as the host cell, an expression vector includes, for example, pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 *[Nature*, 329, 840, (1987)], pcDNAI/Amp (manufactured by Invitrogen), pREP4 (manufactured by Invitrogen), pAGE103 *[J. Biochemistry*, 101, 1307 (1987)], pAGE210, pME18SFL3 and the like.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter and the like. Also, the enhancer of the IE gene of human CMV can be used together with the promoter.

The host cell includes human Namalwa cell, monkey COS cell, Chinese hamster ovary (CHO) cell, HST5637 (Japanese Published Unexamined Patent Application No. 299/88) and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the like.

As the expression method of the gene, in addition to direct expression, secretory production, fusion protein expression and the like in accordance with the method described in *Molecular Cloning, A Laboratory Manual*, Second Edition, Cold Spring Harbor Laboratory Press (1989) can be carried out. When expression is carried out in a cell derived from eukaryote, a polypeptide to which a sugar or a sugar chain is added can be obtained.

The polypeptide used in the present invention can be produced by culturing the thus obtained transformant in a medium to form and accumulate the polypeptide in the culture, and recovering it from the culture. The method for culturing the transformant in the medium is carried out according to the usual method used in culturing of hosts.

When a microorganism transformed with a recombinant vector containing an inducible promoter as a promoter is cultured, an inducer can be added to the medium, if necessary. For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)] and 199 medium [*Proceeding of the Society for Experimental Biology and Medicine*, 73, 1 (1950)], the media to which fetal calf serum, etc. is added, and the like. The culturing is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Thus, the polypeptide used in the present invention can be produced by culturing a transformant derived from a microorganism, an animal cell or the like which comprises a recombinant vector into which a DNA encoding the polypeptide used in the present invention is inserted, in accordance with a general culturing method, to thereby form and accumulate the polypeptide, and then recovering the polypeptide from the culture.

The process for producing the polypeptide includes a method of intracellular expression in a host cell, a method of extracellular secretion from a host cell, a method of producing on a host cell membrane outer envelope, and the like. The appropriate method can be selected by changing the host cell used. Also, it can be produced by expressing it as a fusion polypeptide by fusing any protein according to protein engineering techniques.

When the polypeptide is produced in a host cell or on a host cell membrane outer envelope, the gene product can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and WO94/23021, and the like. Also, the production amount can be increased in accordance with the method described in Japanese Published Unexamined Patent Application No. 227075/90 utilizing a gene amplification system using a dihydrofolate reductase gene.

The polypeptide can be isolated and purified from the above culture, for example, as follows.

When the polypeptide is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general enzyme isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When the polypeptide is expressed intracellularly by forming an inclusion body, the cells are recovered, disrupted and centrifuged in the same manner, and the inclusion body of the polypeptide are recovered as a precipitation fraction. The recovered inclusion body of the protein is solubilized with a protein denaturing agent. The protein is made into a normal three-dimensional structure by diluting or dialyzing the solubilized solution, and then a purified product of the polypeptide is obtained by the same isolation purification method as above.

When the polypeptide or the derivative such as a glycosylated polypeptide is secreted extracellularly, the polypeptide or the derivative such as a glycosylated polypeptide can be recovered from the culture supernatant. That is, the culture is treated by a method such as centrifugation in the same manner as above to obtain a culture supernatant from which solids are removed, a purified product of the polypeptide can be obtained from the culture supernatant by the same isolation purification method as above.

Also, the polypeptide used in the present invention or a partial peptide of the polypeptide can be produced by a chemical synthesis method, such as Fmoc (fluorenylmethyloxycarbonyl) method or tBoc (t-butyloxycarbonyl) method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

The polypeptide or the peptide having a partial sequence of the polypeptide obtained by the above method can be used as an antigen.

(2) Immunization of Animal and Preparation of Antibody-Producing Cell

A mouse, rat or hamster 3 to 20 weeks old is immunized with the antigen prepared above, and antibody-producing cells are collected from the spleen, lymph node or peripheral blood of the animal.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies—A Laboratory Manual* (Cold Spring Harbor Laboratory (1988)] or the like. A mouse, rat or hamster showing a sufficient antibody titer in their sera against the antigen used for the immunization is used as the supply source of antibody-producing cells.

A polyclonal antibody can be prepared by separating and purifying the serum. Whether the polyclonal antibody specifically recognizes three-dimensional structure of an extracellular region of a polypeptide encoded by the PERP gene and binds to the extracellular region can be examined by the method described in (6) below.

In fusion of the antibody-producing cells and myeloma cells, on the 3rd to 7th days after final administration of the antigen, tissue containing the antibody-producing cells such as the spleen from the immunized mouse, rat or hamster is excised to collect the antibody-producing cell. When the spleen cells are used, the spleen is cut out in an MEM medium (NIHON Pharmaceutical) and loosened by tweezers and centrifuged (at 1200 rpm, for 5 minutes). Then, the supernatant is discarded and a Tris-ammonium chloride buffer (pH. 7.65) is applied for 1 to 2 minutes to remove erythrocytes. After washing 3 times with the MEM medium, antibody-producing cells for fusion is provided.

(3) Preparation of Myeloma Cell

An established cell line obtained from mouse is used as myeloma cells. Examples include 8-azaguanine-resistant mouse (derived from BALB/c mouse) myeloma cell line P3-X63Ag8-U1(P3-U1) [*Current Topics in Microbiology and Immunology*, 18, 1 (1978)], P3-NS1/1-Ag41(NS-1) [*European J. Immunology*, 6, 511 (1976)], SP2/0-Ag14(SP-2) [*Nature*, 276, 269 (1978)], P3-X63-Ag8653(653) [*J. Immunology*, 123, 1548 (1979)], P3-X63-Ag8(X63) [*Nature*, 256, 495 (1975)] and the like. These cell lines are subcultured in an 8-azaguanine medium [a medium in which glutamine (1.5 mmol/L), 2-mercaptoethanol ($5\times10^{-5}$ mol/L), gentamicin (10 μg/ml) and fetal calf serum (FCS) are added to RPMI-1640 medium (hereinafter referred to as "normal medium") and 8-azaguanine (15 μg/ml) is further added] and they are subcultured in the normal medium 3 or 4 days before cell fusion to ensure the cell number of $2\times10^{7}$ or more on the day for fusion.

(4) Cell Fusion

The above-described antibody-producing cells and myeloma cells were sufficiently washed with an MEM medium or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells:the myeloma cells=5 to 10:1, followed by centrifugation (1200 rpm, 5 minutes). Then, the supernatant is discarded, and precipitated cell group is sufficiently loosen. To $1\times10^{8}$ of the antibody-producing cells, 0.2 to 1 mL of a mixture solution of 2 g of polyethylene glycol-1000 (PEG-1000), 2 mL of MEM and 0.7 mL of dimethylsulfoxide is added under stirring at 37° C., and 1 to 2 mL of MEM medium is added several times every one or two minutes, and MEM medium is added to give a total amount of 50 mL. After centrifugation (900 rpm, 5 minutes), the supernatant is discarded, the cells are gently loosen, and the cells are gently suspended in 100 mL of HAT medium [a medium in which hypoxanthine ($10^{-4}$ mol/L), thymidine ($1.5\times10^{-5}$ mol/L) and aminopterin ($4\times10^{-7}$ mol/L) is added to the normal medium] by suction and sucking out using a measuring pipette. The suspension is dispensed at 100 μL/well onto a 96-well culturing plate and cultured in a 5% $CO_2$ incubator at 37° C. for 7 to 14 days.

After the culturing, a portion of the culture supernatant is sampled and a well containing a hybridoma which produces an antibody which specifically recognizes three-dimensional structure of an extracellular region of a polypeptide encoded by the PERP gene and binds to the extracellular region is selected according to the method for selecting a hybridoma described below. Then, cloning is carried out twice by a limiting dilution method [Firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Monoclonal Antibody

The hybridoma cells producing an anti-PERP monoclonal antibody obtained in (4) are administered by intraperitoneal injection into 8- to 10-week-old mice or nude mice treated with pristane (0.5 ml of 2,6,10,14-tetramethylpentadecane (pristane) is intraperitoneally administered, followed by feeding for 2 weeks) at a dose of $2\times10^{6}$ to $5\times10^{7}$ cells/animal. The hybridoma develops ascites tumor in 10 to 21 days. The ascitic fluid is collected from the mice, centrifuged (at 3,000 rpm, for 5 minutes) to remove solids, subjected to salting out with 40 to 50% saturated ammonium sulfate and then precipitated by caprylic acid, passed through a DEAE-Sepharose column, a protein A column or a gel filtration column to collect an IgG or IgM fraction as a purified monoclonal antibody.

The subclass of the antibody can be determined using a subclass typing kit by an enzyme immunoassay. The amount of the protein can be determined by the Lowry method or from the absorbance at 280 nm.

(6) Method for Selecting Hybridoma

As the method for selecting a hybridoma producing antibody which specifically recognizes three-dimensional structure of an extracellular region of a polypeptide encoded by the PERP gene and binds to the extracellular region in the present invention, the following method is exemplified.

In order to select an antibody capable of binding to the extracellular region of the polypeptide encoded by the PERP gene maintaining the natural three-dimensional structure, any method can be used, so long as it is a method which can examine binding activity of the polypeptide encoded by the PERP gene to a cell naturally existing in human body, a cell line established from human body or a cell obtained by gene recombinant techniques. Examples include an immunofluorescent staining method using FMAT8100HTS system (manufactured by Applied Biosystem) or a fluorescent cell staining method using a flow cytometry. Specific methods include methods described in (3) of Example 4 and (2) of Example 5.

Also, the method for confirming the reactivity include those combining known immunological detection methods [*Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

The cell naturally existing in human body, the cell line established from human body and the cell obtained by gene recombinant techniques for obtaining the polypeptide encoded by the PERP gene include the cells described above, and the cell expressing the polypeptide encoded by the PERP gene obtained by gene recombination techniques is preferred because whether or not the polypeptide is expressed is apparent. With regard to the cell obtained by gene recombinant techniques, it is easy to prepare a cell which does not express the polypeptide as a negative control.

Examples of the hybridoma producing a monoclonal antibody which specifically recognizes three-dimensional structure of an extracellular region of a polypeptide encoded by the PERP gene in the present invention selected by the above method includes a hybridoma cell line KM3411 which produces a monoclonal antibody KM3411, and the like. The hybridoma KM3411 has been deposited to International Patent Organism Depositary, National Institute of Advanced Industrial Science and Technology (Central 6, 1-1, Higashi 1-chome, Tsukuba-shi, Ibaraki, Japan) as FERM BP-8643 on Feb. 24, 2004.

2. Preparation of Gene Recombinant Antibody Having No Consensus Sequence of an N-Linked Sugar Chain in V Region An antibody which has no consensus sequence of an N-linked sugar chain in V region can be produced by introducing a modification into the consensus sequence of an antibody having the consensus sequence of an N-linked sugar chain in V region. Production examples are shown below.

(1) Analysis of Nucleotide Sequence or Amino Acid Sequence Encoding V Region of the Antibody Having the Consensus Sequence of an N-Linked Sugar Chain in V Region Whether or not the consensus sequence of an N-linked sugar chain, Asn-Xaa-Ser/Thr (Xaa represents an optional amino acid residue, and Ser/Thr represents either Ser residue or Thr residue) is contained in V region is examined by analyzing the nucleotide sequence or amino acid sequence of V region.

The nucleotide sequence of V region can be determined, for example, by cloning cDNAs encoding VH and VL of the antibody as described below. The amino acid sequence of the antibody is deduced from the above nucleotide sequence of cDNA or can be determined by directly analyzing the antibody with a peptide sequencer [*Molecular Cloning, A Laboratory Manual*, Second Edition, Cold Spring Harbor Laboratory Press (1989)].

A method for cloning cDNA encoding an antibody variable region from a hybridoma producing a mouse monoclonal antibody or the like is described below.

mRNA is extracted from hybridoma cells producing a mouse antibody or the like to synthesize cDNA. The synthesized cDNA is cloned into a vector such as a phage or a plasmid, to prepare a cDNA library. Each of a recombinant phage or recombinant plasmid containing cDNA encoding VH or VL is isolated from the library using DNA encoding a part of the C region or V region of a mouse antibody as the probe. The full length of the nucleotide sequences of VH and VL of the mouse antibody of interest on the recombinant phage or recombinant plasmid are determined, and the full length of the amino acid sequences of VH and VL are deduced from the nucleotide sequences.

The non-human animal may be any animal such as mouse, rat, hamster or rabbit, so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)] and the like. Examples of the method for preparing mRNA from total RNA include an oligo (dT) immobilized cellulose column method [*Molecular Cloning, A Laboratory Manual*, Second Edition, Cold Spring Harbor Laboratory Press (1989)] and the like. Also, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods [*Molecular Cloning, A Laboratory Manual*, Second Edition, Cold Spring Harbor Lab. Press (1989); *Current Protocols in Molecular Biology*, Supplement 1-34]; a method using a commercially available kit such as Super Script™ Plasmid System for cDNA Synthesis and Plasmid Cloning (manufactured by GIBCO BRL), ZAP-cDNA Synthesis Kit (manufactured by Stratagene), etc.; and the like.

The vector into which the synthesized cDNA using mRNA extracted from a hybridoma cell as the template is inserted for preparing a cDNA library may be any vector, so long as the cDNA can be inserted. Examples include ZAP Express [*Strategies*, 5, 58 (1992)], pBluescript II SK(+) [*Nucleic Acids Research*, 17, 9494 (1989)], λZAPII (manufactured by Stratagene), λgt10 and λgt11 [*DNA Cloning: A Practical Approach*, I, 49 (1985)], Lambda BlueMid (manufactured by Clontech), λExCell and pT7T3 18U (manufactured by Pharmacia), pcD2 (*Mol. Cell. Biol.*, 3, 280 (1983)), pUC18 [*Gene*, 33, 103 (1985)], and the like.

Any *Escherichia coli* for introducing the cDNA library constructed by a phage or plasmid vector may be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222: 778 (1983)), NM522 (*J. Mol. Biol.*, 166, 1 (1983)], K802 [*J. Mol. Biol.*, 16, 118 (1966)), JM105 (*Gene*, 38, 275 (1985)], and the like.

A colony hybridization or plaque hybridization method using an isotope- or fluorescence-labeled probe may be used for selecting cDNA clones encoding VH and VL of a non-human animal antibody from the cDNA library [*Molecular Cloning, A Laboratory Manual*, Second Edition, Cold Spring Harbor Laboratory Press (1989)]. Also, the cDNAs encoding VH and VL can be prepared through polymerase chain reaction [hereinafter referred to as "PCR"; *Molecular Cloning, A Laboratory Manual*, Second Edition, Cold Spring Harbor Laboratory Press (1989); *Current Protocols in Molecular Biology*, Supplement 1-34] by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBluescript SK(−) (manufactured by Stratagene), carrying out the reaction by a usually used nucleotide analyzing method such as the dideoxy method of Sanger, F. et al. [*Proc. Natl. Acad. Sci. USA*, 74, 5463 (1977)], and then analyzing the sequence using an automatic nucleotide sequence analyzer such as A.L.F. DNA sequencer (manufactured by Pharmacia).

Whether the obtained cDNAs encode the full amino acid sequences of VL and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full length of the amino acid sequences of VH and VL of the antibody comprising a secretory signal sequence with full length of the amino acid sequences of VH and VL of known antibodies [*Sequences of Proteins of Immunological Interest*, US Dept. Health and Human Services (1991)], and the subgroup to which they belong can also be known. Furthermore, the amino acid sequence of each of CDRs of VH and VL can be found by comparing the obtained amino acid sequences with amino acid sequences of VH and VL of known antibodies [*Sequences of Proteins of Immunological Interest*, US Dept. Health and Human Services (1991)].

Moreover, the novelty of the sequence can be examined by carrying out a homology search with sequences in any database, for example, SWISS-PROT, PIR-Protein or the like using the full length of the amino acid sequences of VH and VL, for example, according to the BLAST method [*J. Mol. Biol.*, 215, 403 (1990)] or the like.

(2) Production of Gene Recombinant Antibody Having No Consensus Sequence of an N-Linked Sugar Chain in V Region V region of an antibody having no consensus sequence (Asn-Xaa-Ser/Thr) of an N-linked sugar chain in V region can be produced by substituting Asn residue and/or Ser residue/Thr residue in a consensus sequence of an N-linked sugar chain with other amino acid residues.

V region of the antibody, particularly CDR, is an important region which defines the binding activity of the antibody to the antigen. Accordingly, the binding activity of the antibody to the antigen may be changed by substitution of any amino acid residues in V region of the antibody, particularly in CDR. Therefore, when the above V region having no consensus sequence is produced, modification should be carried out to obtain an amino acid sequence which does not change the binding activity of the antibody to the antigen. Specific methods thereof are described below.

In order to modify Asn residue and Ser residue or Thr residue in the consensus sequence of an N-linked sugar chain in V region with an amino acid sequence which does not change the binding activity of the antibody to the antigen, it is preferred to avoid modification which directly affects the binding of the antibody to the antigen and modification which changes the three-dimensional structure of the antibody to thereby indirectly affect the binding of the antibody to the antigen.

In order to avoid the modification which directly affects the binding of the antibody to the antigen and the modification which changes the three-dimensional structure of the antibody to thereby indirectly affect the binding activity of the antibody to the antigen, it is most important how to efficiently anticipate site specific mutation of an amino acid residue having little possibility of affecting the binding activity of the antibody to the antigen. Therefore, the three-dimensional structure of an antibody is constructed and analyzed by X-ray crystallography [*J. Mol. Biol.*, 112, 535 (1977)], computer-modeling [*Protein Engineering*, 7, 1501 (1994)] or the like. However, even if the modifications is carried out based on the information of the three-dimensional structure of the antibody, introduction of mutation into V region of the antibody, particularly CDR, may change the binding activity of the antibody to the antigen. Therefore, when the mutations are introduced, various attempts must be necessary, for example, several modified antibodies are produced and the correlation between the amino acid modification and the antibody binding activity is examined.

Thus, the site specific mutation of the amino acid residue having little possibility of affecting the binding activity of the antibody to the antigen is estimated, and then DNA sequences encoding the amino acid sequence of V region of the antibody into which the mutation is introduced are designed. Based on the designed DNA sequences, several synthetic DNAs having a length of about 100 nucleotides are synthesized, and PCR is carried out using them. In this case, it is preferred in each of the H chain and the L chain that 6 synthetic DNAs are designed in view of the reaction efficiency of PCR and the lengths of DNAs which can be synthesized.

Furthermore, the DNA encoding the amino acid sequence of the antibody V region into which the mutation is introduced can be easily cloned into the vector for expression of antibody into which DNAs encoding CH and CL of a human antibody have been inserted, constructed in (3)-1 of this item, by introducing the recognition sequence of an appropriate restriction enzyme to the 5' terminal of the synthetic DNAs existing on the both ends.

After the PCR, each of amplified products is cloned into a plasmid such as pBluescript SK (−) (manufactured by Stratagene), and the nucleotide sequence is determined according to the method described in (1) of this item to confirm obtaining of a plasmid comprising cDNA having a DNA sequence encoding the amino acid sequence of V region of the gene recombinant antibody having no consensus sequence of an N-linked sugar chain in V region of the antibody.

Also, a plasmid comprising cDNA having the desired DNA sequence can be prepared by using a known site specific mutation method [*Molecular Cloning, A Laboratory Manual*, Second Edition, Cold Spring Harbor Laboratory Press (1989)] such as Kunkel method for cDNA encoding V region of the antibody which is used as a basis for mutation, or introducing mutation into a DNA encoding the amino acid sequence of a region containing a consensus sequence of an N-linked sugar chain using PCR or the like by utilizing a restriction enzyme recognition site in cDNA encoding V region of the antibody which is used as basis for mutation, and substituting it with cDNA encoding V region of the antibody which is used as basis for mutation.

Completion of the desired modification in the amino acid residue of V region is confirmed by determining the nucleotide sequence of the plasmid comprising cDNA having a DNA sequence encoding the amino acid sequence of VH or VL of the gene recombinant antibody obtained as described above, according to the method described in (1) of this item.

(3) Production of Gene Recombinant Antibody

As production examples of gene recombinant antibodies, processes for producing a human chimeric antibody and a humanized antibody are shown below.

(3)-1 Construction of Vector for Expression of Antibody into which DNAs Encoding CH and CL of a Human Antibody have been Inserted A vector for expression of antibody into which DNAs encoding CH and CL of a human antibody have been inserted is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to κ class, and the like. As the DNAs encoding CH and CL of a human antibody, a chromosomal DNA comprising an exon and an intron or cDNA can be used and cDNA is preferably used. As the expression vector for animal cell, any expression vector can be used, so long as a gene encoding the C region of a human antibody can be inserted thereinto and expressed therein. Examples include pAGE107 [*Cytotechnol.,* 3, 133 (1990)], pAGE103 [*J. Biochem.,* 101, 1307 (1987)], pHSG274 [*Gene,* 27, 223 (1984)], pKCR [*Proc. Natl. Acad. Sci. USA,* 78, 1527 (1981)], pSG1bd2-4 [*Cytotechnol.,* 4, 173 (1990)], pSE1UK1Sed1-3 [*Cytotechnol.,* 13, 79 (1993)] and the like. Examples of a promoter and enhancer used for an expression vector for animal cell include an SV40 early promoter [*J. Biochem.,* 101, 1307 (1987)], a Moloney mouse leukemia virus LTR [*Biochem. Biophys. Res. Commun.,* 149, 960 (1987)], an immunoglobulin H chain promoter [*Cell*, 41, 479 (1985)] and enhancer [*Cell*, 33, 717 (1983)], and the like.

The vector for expression of antibody into which DNAs encoding CH and CL of a human antibody have been inserted may be either of a type in which a gene encoding an antibody H chain and a gene encoding an antibody L chain exist on separate vectors or of a type in which both genes exist on the same vector (tandem type). In respect of easiness of construction of a vector for expression of antibody into which DNAs encoding CH and CL of a human antibody have been inserted, easiness of introduction into animal cells, and balance between the expression amounts of antibody H and L chains in animal cells, a tandem type of the vector for expression of antibody into which DNAs encoding CH and CL of a human antibody have been inserted is more preferred [*J. Immunol. Methods*, 167, 271 (1994)]. Examples of the tandem type of the vector for expression of antibody into which DNAs encoding CH and CL of a human antibody have been inserted include pKANTEX93 (WO 97/10354), pEE18 [*Hybridoma*, 17, 559 (1998)], and the like.

The constructed vector for expression of antibody into which DNAs encoding CH and CL of a human antibody have been inserted can be used for expression of a human chimeric antibody and a humanized antibody in animal cells.

(3)-2 Construction of Human Chimeric Antibody Expression Vector cDNAs encoding VH and VL of antibody of non-human animal are cloned into the upstream of genes encoding CH or CL of human antibody of vector for expression of antibody into which DNAs encoding CH and CL of a human antibody have been inserted mentioned in (3)-1 of this item to thereby construct human chimeric antibody expression vector. For example, each cDNA encoding VH and VL of antibody of non-human animal is ligated to synthetic DNA comprising a nucleotide sequence of 3'-terminal of VH or VL of antibody of non-human animal and a nucleotide sequence of 5'-terminal of CH or CL of human antibody and having recognition sequence of an appropriate restriction enzyme at both ends, and cloned so that each of them is expressed in an appropriate form in the upstream of gene encoding CH or CL of human antibody of the vector for expression of antibody into which DNAs encoding CH and CL of a human antibody have been inserted mentioned in (3)-1 of this item to construct human chimeric antibody expression vector. In addition, cDNA encoding VH or VL of the antibody in which modification is introduced into a consensus sequence of an N-linked sugar chain in V region is amplified by PCR using a synthetic DNA having a recognition sequence of an appropriate restriction enzyme at both terminals and each of them is cloned into the vector for expression of antibody into which DNAs encoding CH and CL of a human antibody have been inserted mentioned in (3)-1 of this item.

(3)-3 Construction of cDNA Encoding V Region of Humanized Antibody cDNAs encoding VH or VL of a humanized antibody can be obtained as follows.

First, amino acid sequences of framework region (hereinafter referred to as "FR") in VH or VL of a human antibody to which amino acid sequences of CDRs in VH or VL of an antibody into which the modification is introduced into a consensus sequence of an N-linked sugar chain in V region are grafted are selected. Any amino acid sequences of FR in VH or VL of a human antibody can be used, so long as they are from human antibody. Examples include amino acid sequences of FRs in VH or VL of human antibodies registered in database such as Protein Data Bank, and amino acid sequences common to subgroups of FRs in VH or VL of human antibodies [*Sequences of Proteins of Immunological Interest*, US Dept. Health and Human Services (1991)], and the like. In order to produce a humanized antibody having potent activity, amino acid sequences having high homology (at least 60% or more) with an amino acid sequence of FR in VH or VL of a target antibody from a non-human animal is preferably selected. Then, amino acid sequences of CDRs of VH or VL of the antibody from a target non-human animal are grafted to the selected amino acid sequence of FR in VH or VL of a human antibody, respectively, to design each amino acid sequence of VH or VL of a humanized antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed. Based on the designed DNA sequences, several synthetic DNAs having a length of about 100 nucleotides are synthesized, and PCR is carried out using them.

Furthermore, the cDNA encoding VH or VL of a humanized antibody can be easily cloned into the vector for expression of antibody into which DNAs encoding CH and CL of a human antibody have been inserted constructed in (3)-1 of this item by introducing the recognition sequence of an appropriate restriction enzyme to the 5' terminal of the synthetic DNAs existing on the both ends. After the PCR, each of amplified products is cloned into a plasmid such as pBluescript SK (−) (manufactured by Stratagene), and the nucleotide sequence is determined according to the method described in (1) of this item to obtain a plasmid having a DNA sequence encoding the amino acid sequence of VH or VL of a desired humanized antibody.

(3)-4 Modification of Amino Acid Sequence of V Region of Humanized Antibody

It is known that when a humanized antibody is produced by simply grafting only CDRs in VH and VL of an antibody in which a modification is introduced into a consensus sequence of an N-linked sugar chain in V region into FRs of VH and VL of a human antibody, its antigen-binding activity is lower than that of the original antibody from a non-human animal [*BIO/TECHNOLOGY*, 2, 266 (1991)]. As the reason, it is considered that several amino acid residues in not only CDRs but also FRs directly or indirectly relate to antigen-binding activity in VH and VL of the original antibody derived from a non-human animal, and as a result of grafting of CDRs, such amino acid residues are changed to different amino acid residues of FRs in VH and VL of a human antibody. In order to solve the problem, in humanized antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human animal antibody to thereby increase the antigen binding activity which has been decreased [*BIO/TECHNOLOGY*, 9, 266 (1991)]. In the production of a humanized antibody, how to efficiently identify the amino acid residues relating to the antigen binding activity in FR is most important, so that the three-dimensional structure of an antibody is constructed and analyzed by X-ray crystallography [*J. Mol. Biol.*, 112, 535 (1977)], computer-modeling [*Protein Engineering*, 7, 1501 (1994)] or the like. Although the information of the three-dimensional structure of antibodies has been useful in the production of a humanized antibody, no method for producing a humanized antibody which can be applied to any antibodies has been established yet. Therefore, various attempts must be currently necessary, for example, several modified antibodies of each antibody are produced and the correlation between each of the modified antibodies and its antibody binding activity is examined.

The modification of the amino acid sequence of FR in VH and VL of a human antibody can be accomplished using various synthetic DNA for modification according to PCR as described in (3)-3 of this item. With regard to the amplified product obtained by the PCR, the nucleotide sequence is determined according to the method as described in (1) of this item so that whether the objective modification has been carried out is confirmed.

(3)-5 Construction of Humanized Antibody Expression Vector

A humanized antibody expression vector can be constructed by cloning each cDNA encoding VH or VL of a constructed humanized antibody into upstream of each gene encoding CH or CL of the human antibody in the vector for expression of antibody in which DNAs encoding CH and CL of a human antibody have been inserted as described in (3)-1 of this item.

For example, when recognizing sequences of an appropriate restriction enzymes are introduced to the 5'-terminal of synthetic DNAs positioned at both ends among synthetic DNAs used in the construction of VH or VL of the humanized antibody in (3)-3 and (3)-4 of this item, cloning can be carried out so that they are expressed in an appropriate form in the upstream of each gene encoding CH or CL of the human antibody in the vector for expression of antibody in which DNAs encoding CH and CL of a human antibody have been inserted as described in (3)-1 of this item.

(3)-6 Transient Expression of Human Chimeric Antibody or Humanized Antibody

In order to efficiently evaluate the antigen binding activity of human chimeric antibodies or humanized antibodies produced, the human chimeric antibodies or the humanized antibodies can be expressed transiently using the human chimeric antibody or humanized antibody expression vector as described in (3)-3 and (3)-5 of this item. Any cell can be used as a host cell, so long as the host cell can express a human chimeric antibody or a humanized antibody. Generally, COS-7 cell (ATCC CRL1651) is used in view of its high expression amount [*Methods in Nucleic Acids Res.*, CRC Press, p. 283 (1991)]. Examples of the method for introducing the expression vector into COS-7 cell include a DEAE-dextran method [*Methods in Nucleic Acids Res.*, CRC Press, p. 283 (1991)], a lipofection method [*Proc. Natl. Acad. Sci. USA*, 84: 7413 (1987)], and the like.

After introduction of the vector, the expression amount and antigen binding activity of the human chimeric antibody or the humanized antibody in the culture supernatant can be determined by the enzyme immunoassay [hereinafter referred to as "ELISA"; *Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

(3)-7 Stable Expression of Human Chimeric Antibody or Humanized Antibody

A transformant which stably expresses a human chimeric antibody or a humanized antibody can be obtained by introducing into an appropriate host cell the human chimeric antibody expression vector or the humanized antibody expression vector described in (3)-2 and (3)-5 of this item.

Examples of the method for introducing the expression vector into a host cell include electroporation [Japanese Published Unexamined Patent Application No. 257891/90, *Cytotechnology*, 3, 133 (1990)] and the like.

As the host cell into which a human chimeric antibody expression vector or a humanized antibody expression vector is introduced, any cell can be used, so long as it is a host cell which can express the human chimeric antibody or the humanized antibody. Examples include mouse SP2/0-Ag14 cell (ATCC CRL1581), mouse P3x63-Ag8.653 cell (ATCC CRL1580), CHO cell in which a dihydrofolate reductase gene (hereinafter referred to as "DHFR") is defective [*Proc. Natl. Acad. Sci. U.S.A.*, 77, 4216 (1980)], lectin resistance-acquired Lec13 [*Somatic Cell and Molecular genetics*, 12, 55 (1986)], CHO cell in which α1,6-fucosyltransaferse gene is defected (WO05/35586), rat YB2/3HL.P2.G11.16Ag.20 cell (ATCC CRL1662), and the like.

In addition to the above host cells, host cells in which activity of a protein such as an enzyme relating to synthesis of an intracellular sugar nucleotide, GDP-fucose, a protein such as an enzyme relating to the modification of a sugar chain in which 1-position of fucose is bound to 6-position of N-acetylglucosamine in the reducing end through α-bond in a complex type N-glycoside-linked sugar chain, or a protein relating to transport of an intracellular sugar nucleotide, GDP-fucose, to the Golgi body are decreased or deleted, preferably CHO cell in which α1,6-fucosyltransferase gene is defected as described in WO05/35586, can also be used.

After introduction of the expression vector, transformants which express a human chimeric antibody or a humanized antibody stably are selected in accordance with the method disclosed in Japanese Published Unexamined Patent Application No. 257891/90, by culturing in a medium for animal cell culture containing an agent such as G418 sulfate (hereinafter referred to as "G418", manufactured by Sigma) or the like. Examples of the medium for animal cell culture include RPMI1640 medium (manufactured by Invitrogen), GIT medium (manufactured by NIHON Pharmaceutical), EX-CELL301 medium (manufactured by JRH), IMDM medium (manufactured by Invitrogen), Hybridoma-SFM medium (manufactured by Invitrogen), media obtained by adding various additives such as fetal bovine serum (hereinafter referred to as "FBS") to these media, and the like. The human chimeric antibody or the humanized antibody can be expressed and accumulated in a culture supernatant by culturing the selected transformants in a medium. The expression amount and antigen binding activity of the human chimeric antibody or the humanized antibody in the culture supernatant can be measured by ELISA or the like. Also, in the transformant, the expression amount of the humanized antibody can be increased by using dhfr amplification system or the like according to the method disclosed in Japanese Published Unexamined Patent Application No. 257891/90.

The human chimeric antibody or the humanized antibody can be purified from the culture supernatant of the transformant by using a protein A column [*Monoclonal Antibodies—Principles and practice*, Third edition, Academic Press (1996), *Antibodies—A Laboratory Manual*, Cold Spring Harbor Laboratory (1988)]. Any other conventional methods for protein purification can be used. For example, the human chimeric antibody or the humanized antibody can be purified by a combination of gel filtration, ion-exchange chromatography, ultrafiltration and the like. The molecular weight of the H chain or the L chain of the purified human chimeric antibody or humanized antibody or the antibody molecule as a whole is determined by polyacrylamide gel electrophoresis (hereinafter referred to as "SDS-PAGE") [*Nature*, 227, 680

(1970)], Western blotting [*Monoclonal Antibodies—Principles and practice*, Third edition, Academic Press (1996), *Antibodies—A Laboratory Manual*, Cold Spring Harbor Laboratory (1988)], and the like.

3. Evaluation of Activity of Gene Recombinant Antibody or Antibody Fragment of the Present Invention The binding activity to an antigen and the binding activity to a PERP-expressing cell line of the purified gene recombinant antibody or antibody fragment of the present invention can be determined by ELISA, an immunofluorescent method [*Cancer Immuno Immunother.*, 36, 373 (1993)], surface plasmon resonance using, for example, BIAcore™, or the like. The cytotoxic activity against an antigen positive culture cell line can be evaluated by measuring the CDC activity, the ADCC activity or the like [*Cancer Immunol. Immunother.*, 36: 373 (1993)]. Also, influence of the modification introduced into V region on the binding activity of the antibody to the antigen can be found by comparing these results with measuring results in the monoclonal antibody which has no modification introduced into V region, specifically recognizes three-dimensional structure of an extracellular region of a polypeptide encoded by the PERP gene and binds to the extracellular region, which was used as a basis of the production of the gene recombinant antibody of the present invention, as described in the above item 1.

4. Method for Treating Disease Using the Gene Recombinant Antibody or Antibody Fragment of the Present Invention The gene recombinant antibody of the present invention which has no consensus sequence of an N-linked sugar chain in a variable region, specifically recognizes three-dimensional structure of an extracellular region of a polypeptide encoded by the PERP gene and binds to the extracellular region, or the antibody fragment can be used for the treatment of diseases relating to the polypeptide encoded by the PERP gene.

The disease relating to the PERP gene is not limited, so long as it is a disease relating to a cell expressing the gene, such as cancer. The cancer includes cancer derived from epidermis, such as breast cancer, uterine cancer, colorectal cancer, stomach cancer, ovarian cancer, lung cancer, renal cancer, rectal cancer, thyroid cancer, uterine cervix cancer, small intestinal cancer, prostate cancer and pancreatic cancer.

A therapeutic agent comprising the gene recombinant antibody or antibody fragment of the present invention as an active ingredient includes a therapeutic agent which comprises regulating activity of a polypeptide encoded by the PERP gene and a therapeutic agent by ADCC activity and CDC activity or by an apoptosis-inducing activity.

ADCC activity and CDC activity of the gene recombinant antibody can be measured by a method described, for example, in Japanese Published Unexamined Patent Application No. 205694/94. The antibody having such activity can injure the cell in which a specific antigen is expressed in vivo and, therefore, it can be used as a therapeutic agent for the disease. A human chimeric antibody, a humanized antibody and having an antibody constant region of human IgG class can be effectively used as therapeutic agents [*Cancer Res.*, 56, 1118 (1996)].

The gene recombinant antibody or antibody fragment of the present invention can recognize the natural-type polypeptide encoded by the PERP gene which is not denatured and, therefore, it can recognize a cell in which polypeptide encoded by PERP gene existing in living body. Accordingly, the gene recombinant antibody or antibody fragment of the present invention can injure the cell in which the PERP gene is expressed in vivo or in vitro. Particularly, since expression of the PERP gene is promoted in cancer, the gene recombinant antibody or antibody fragment of the present invention can be used as a therapeutic agent for cancer. In addition, the gene recombinant antibody or antibody fragment of the present invention which has high ADCC activity is used particularly effectively as a therapeutic agent for the treatment to decrease the cells in which the PERP gene is expressed.

The therapeutic agent comprising the gene recombinant antibody or antibody fragment of the present invention or a fusion antibody thereof may contain only the antibody or antibody fragment of the present invention or a derivative thereof as an active ingredient, but generally, it is preferred to provide it as a pharmaceutical preparation produced by an appropriate method well known in the technical field of pharmaceutics, by mixing it with one or more pharmaceutically acceptable carriers.

It is preferred to select a route of administration which is most effective in treatment. Examples include oral administration and parenteral administration, such as buccal, tracheal, rectal, subcutaneous, intramuscular or intravenous administration. In the case of an antibody or peptide formulation, intravenous administration is preferred. The dosage form includes sprays, capsules, tablets, granules, syrups, emulsions, suppositories, injections, ointments, tapes and the like.

The pharmaceutical preparation suitable for oral administration includes emulsions, syrups, capsules, tablets, powders, granules and the like. Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like. Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like. Injections can be prepared using a carrier such as a salt solution, a glucose solution or a mixture of both thereof. Suppositories can be prepared using a carrier such as cacao butter, hydrogenated fat or carboxylic acid. Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. Depending on the properties of the antibody and the carrier, it is possible to produce pharmaceutical preparations such as aerosols and dry powders. In addition, the components exemplified as additives for oral preparations can also be added to the parenteral preparations.

Although the dose or the frequency of administration varies depending on the objective therapeutic effect, administration method, treating period, age, body weight and the like, it is usually 10 µg/kg to 8 mg/kg per day and per adult.

The present invention is explained below in detail based on Examples; however, the present invention is not limited to the following Examples.

EXAMPLE 1

Preparation of Gene Recombinant Antibody which has No Consensus Sequence of an N-Linked Sugar Chain in a Variable Region, Specifically Recognizes Three-Dimensional Structure of an Extracellular Region of a Polypeptide Encoded by the PERP Gene and Binds to the Extracellular Region The recombinant antibody of the present invention was produced based on an anti-PERP mouse antibody KM3411 produced from an anti-PERP antibody-producing hybridoma KM3411 (FERM BP-8643) produced by a method described in (2) of Reference Example 1. As described in (1)-3 of Reference Example 2, the antibody has a consensus sequence of an N-linked sugar chain in VH represented by SEQ ID NO:21. Thereafter, an amino acid sequence of VH of a recombinant antibody gene recombinant antibody having no consensus sequence of an N-linked sugar chain in V region was designed.

(1) Design of Amino Acid Sequence of VH of Gene Recombinant Antibody Having No Consensus Sequence of an N-Linked Sugar Chain in V Region An amino acid sequence of VH of a modified antibody having no consensus sequence of an N-linked sugar chain in V region was designed as follows.

Consensus sequence of an N-linked sugar chain is a sequence comprising Asn at position 59, Tyr at position 60 and Ser at position 61 in the amino acid sequence represented by SEQ ID NO:21. In the amino acid sequence represented by SEQ ID NO:21, CDR2 comprises the amino acid sequence represented by SEQ ID NO:45. In the amino acid sequence represented by SEQ ID NO:45, a consensus sequence of an N-linked sugar chain is a sequence comprising Asn at position 9, Try at position 10 and Ser at position 11.

In the amino acid sequence represented by SEQ ID NO:45, amino acid at position 10 is optional and, therefore, Asn at position 9 and Ser at position 11 were used as candidate residues for modification. Comparison with the known antibody sequences [*Sequences of Proteins of Immunological Interest*, U.S. Department of Health and Human Services (1991)], consideration in properties of amino acids and the like are considered, three-dimensional structure of an anti-PERP CDR-modified antibody was analyzed by a computer modeling and design of an amino acid sequence was carried out. With regard to the preparation of coordinates of three-dimensional structure, a software AbM (manufactured by Oxford Molecular Co.) was used while, with regard to the display of the three-dimensional structure, a software Pro-Explore (manufactured by Oxford Molecular Co.) or a software ViewerLite (manufactured by Accelrys) was used and they were carried out according to the instructions attached to each of them. The obtained results were compared with the three-dimensional structure of the anti-PERP mouse antibody and, with regard to amino acid(s) which substitute(s) for an amino acid being thought not to affect the binding activity of the antibody without changing the three-dimensional structure of the antigen-binding site, Ser, Gly or Tyr was selected for Asn at position 9 and/or Ala for Ser at position 11.

With regard to the designed amino acid-modified VH, the following 6 kinds of VH of recombinant VH having no consensus sequence of an N-linked sugar chain in V region in which at least one amino acid residue was substituted were designed. Hereinafter, VH in which Asn at position 59 was substituted with Ser, VH in which Asn at position 59 was substituted with Gly, VH in which Asn at position 59 was substituted with Tyr, VH in which Ser at position 61 was substituted with Ala, VH in which Asn at position 59 was substituted with Ser and Ser at position 61 was substituted with Ala and VH in which Asn at position 59 was substituted with Gly and Ser at position 61 was substituted with Ala were abbreviated as ver.1, ver.2, ver.3, ver.4, ver.5 and ver.6, respectively.

(2)-1 Preparation of Expression Vector of Gene Recombinant Antibody Having No Consensus Sequence Wherein No N-Linked Sugar Chain in V Region By using the plasmid pKM3411H#9 produced in (1)-2 of Reference Example 2 as a template, PCR was carried out using a primer having the nucleotide sequence represented by the following SEQ ID NOs:22 to 27 and a primer having the DNA sequence represented by SEQ ID NO:28 for introduction of an amino acid modification to thereby amplify the desired cDNA fragments. In production of ver.1, ver.2, ver.3, ver.4, ver.5 or ver.6, synthetic DNA (manufactured by Fasmac) represented by SEQ ID NO:24, 25, 23, 22, 26 or 27 was used as a primer, respectively. In the 3'-terminal of these 6 kinds of synthetic DNA, recognition sequence of restriction enzyme for recombining with pKANTEX3411 described in (2)-1 of Reference Example 2 is contained. PCR was carried out by heating at 94° C. for 3 minutes, 25 cycles, one cycle consisting of reaction at 94° C. for 30 seconds, reaction at 58° C. for 30 seconds and reaction at 74° C. for 1 minute, and then reaction at 72° C. for 10 minutes. The PCR was carried out using a GeneAmp PCR System 9700 (manufactured by Applied Biosystems). Any of the products by PCR had a size of about 300 bp.

The pKANTEX3411 which is a vector for expression of the anti-PERP chimeric antibody described in (2)-1 of Reference Example 2 and each of the above-produced PCR products containing DNA encoding ver.1 to ver.6 were used to construct a gene recombinant antibody having no consensus sequence of an N-linked sugar chain in VH region (hereinafter referred to as modified antibody) expression vector. The names of the expression vector, containing ver.1 to ver.6 in VH, are abbreviated as pKANTEX3411 CDR v1 to v6.

The obtained 6 kinds of PCR products were digested with restriction enzymes NotI (manufactured by Takara Shuzo) and XhoI (manufactured by Takara Shuzo), the reaction solution was subjected to agarose gel electrophoresis, and then NotI-XhoI fragment of about 0.3 kb was recovered using QIAquick Gel Extraction Kit (manufactured by Qiagen). The pKANTEX3411 was digested with restriction enzymes NotI (manufactured by Takara Shuzo) and HindIII (manufactured by New England BioLabs), the reaction solution was subjected to agarose gel electrophoresis, and then NotI-HindIII fragments of about 10 kb were recovered using a QIAquick Gel Extraction Kit (manufactured by Qiagen). Further, the pKANTEX3411 was also digested with restriction enzymes HindIII (manufactured by New England BioLabs) and XhoI (manufactured by Takara Shuzo) and HindIII-XhoI fragments of about 3 kb were recovered in the same manner.

Figure 1:
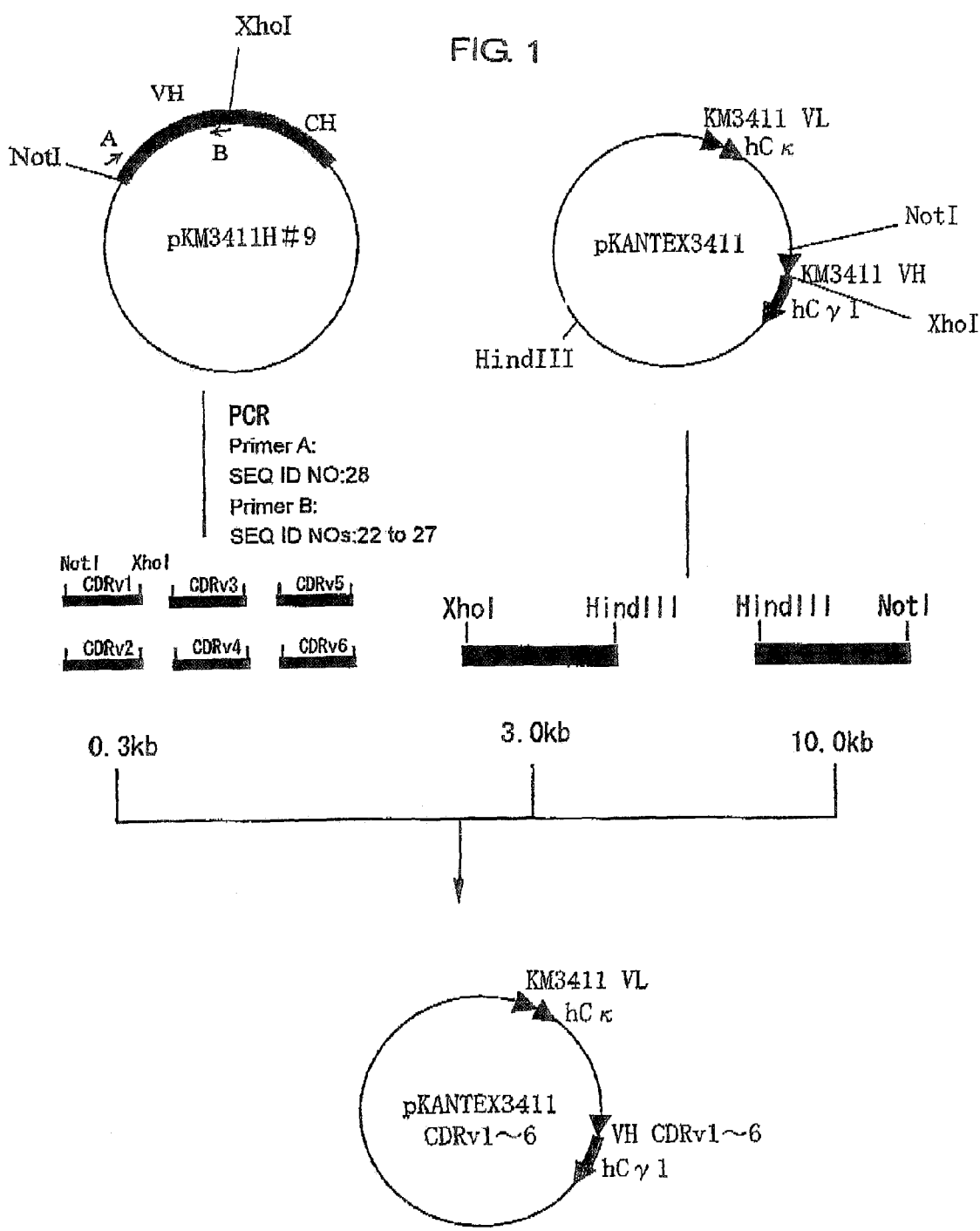
FIG. 1 shows construction steps of plasmids pKAN-TEX3411 CDR v1 to v6.

The obtained 3 kinds of fragments were ligated using a Ligation high (manufactured by TOYOBO) according to the instructions attached thereto and, using the obtained reaction solution, *Escherichia coli* DH5α (manufactured by TOYOBO) was transformed. From the clones of the obtained transformant, each plasmid DNA was produced and treated with a restriction enzyme to thereby confirm that the desired modified antibody expression vectors pKANTEX3411 CDR v1 to v6 into which NotI-XhoI fragments of about 0.3 kb were inserted as shown in FIG. 1 were obtained. The obtained vectors were allowed to react using a BigDye Terminator Cycle Sequencing FS Ready Reaction Kit (manufactured by PE Biosystems) according to the instructions attached thereto and the nucleotide sequences were analyzed by ABI Prism 3700 which is a DNA sequencer of the same manufacturer to thereby confirm that modified antibody expression vectors wherein a desire modification was carried out were produced.

(2)-2 Expression of the Modified Antibody in Animal Cells

The modified antibody expression vectors pKAN-TEX3411 CDR v1 to v6 produced in (2)-1 of this Example were used and expression of the antibody in animal cells was carried out by a conventional method [*Antibody Engineering, A Practical Guide*, W.H. Freeman and Company (1992)] to prepare 6 kinds of transformants into which pKANTEX3411 CDR v1 to v6 were introduced.

(3) Preparation of Purified Antibody

The transformants produced in (2)-2 of this Example were cultured by a conventional culturing method, the cell suspension was recovered therefrom and centrifuged for 5 minutes at 3,000 rpm and 5° C. and the recovered supernatant of the culture was sterilized by filtering through a Millex GV filter (manufactured by Millipore) having a pore size of 0.22 μm. From the obtained supernatant of the culture, each of the modified antibodies ver.1 to ver.6 was purified using a Mab Selected (manufactured by Amersham Bioscience) according to the instructions attached thereto.

The purification degree and expressed molecule size of the purified products of the modified antibodies ver.1 to 6 having no consensus sequence of an N-linked sugar chain in VH region of the obtained antibody were confirmed by electrophoresis using gradient gel (manufactured by ATTO, catalog No.: E-T520L), followed by SDS-PAGE according to the instructions attached thereto. As a control, the anti-PERP chimeric antibody KM3481 described in Reference Example 2 was used.

The result is shown in FIG. 2. In the pure modified antibodies, one band for molecular weight of about 150 kilodaltons (hereinafter referred to as Kd) was found under non-reducing conditions while, under reducing conditions, two bands for molecular weight of about 50 Kd and about 25 Kd were found. With regard to these molecular weight, they coincide with the report that, under non-reducing conditions, molecular weight of antibodies of an IgG class is about 150 Kd while, under reducing conditions, an S—S bond in a molecule is cleaved to decompose into an H chain having a molecular weight of about 50 Kd and an L chain having a molecular weight of about 25 Kd [*Antibodies—A Laboratory Manual*, Cold Spring Harbor Laboratory, Chapter 14 (1988); *Molecular Antibodies—Principles and Practice*, Academic Press Limited (1996)] to thereby confirm that the modified antibodies were expressed as antibody molecules maintaining a correct structures.

EXAMPLE 2

Evaluation of Activity of Modified Antibodies (1) Binding Activity to PERP on Membrane Surface (Fluorescent Antibody Method)

Binding activity of the anti-PERP CDR modified antibody purified in Example 1 to a PERP expression cell line was confirmed by the following method.

As the cell line, non-small cell lung cancer cell line PC9 [*British Journal of Cancer*, 39, 15 (1976)] which had been confirmed to express a polypeptide encoded by the PERP gene was used.

PC9 cells ($2 \times 10^5$ cells per well) were dispensed in a 96-well U-shaped plate, and the modified antibody which was diluted in 6 stages in a 5-fold dilution starting from 50 μg/mL using a buffer for FCM (1% BSA-PBS, 0.02% EDTA and 0.05% $NaN_3$) was dispensed in an amount of 50 μL/well, followed by reaction for 30 minutes on ice. After the reaction solution was washed with a buffer for FCM twice, a solution wherein a PE-labeled anti-human IgG (H+L) antibody (manufactured by Beckmann-Coulter) was diluted 50-fold with a buffer for FCM was added in an amount of 50 μL/well. After the mixture was allowed to react for 30 minutes on ice protecting from the light, it was washed with a buffer for FCM three times and fluorescence intensity was measured by a flow cytometer. The fluorescence intensity was measured by using the anti-PERP chimeric antibody KM3481 described in Reference Example 2 as a control and using an anti-CCR4 antibody KM2760 (WO01/64754) as a negative control.

Figure 3:
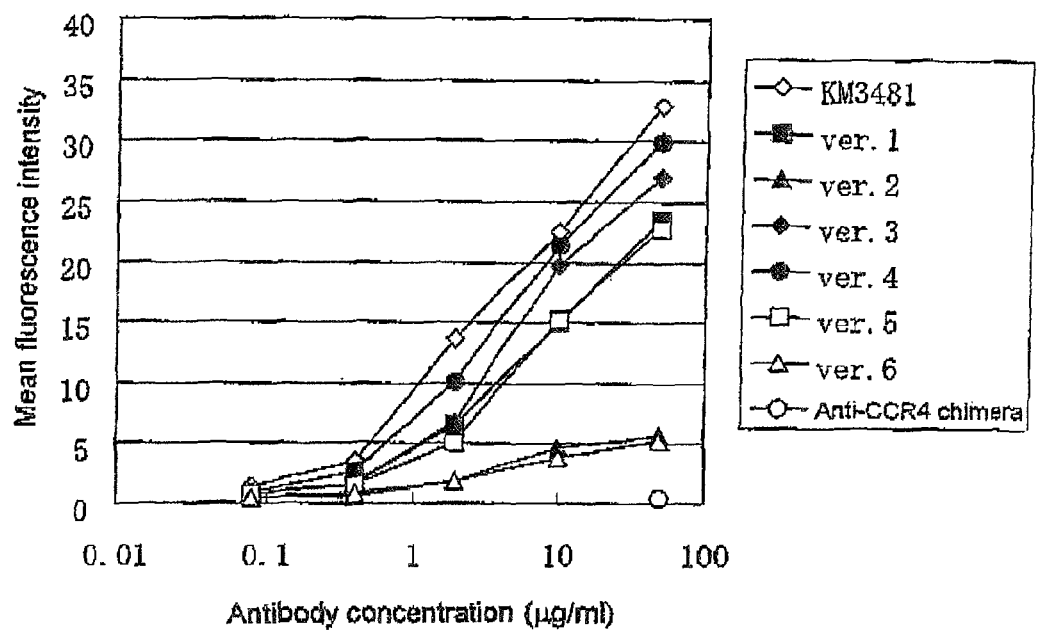
FIG. 3 shows reactivity of each antibody in a flow cytometry. The ordinate and the abscissa in the drawing show mean fluorescence intensity and antibody concentration, respectively. In the drawing, ◇ represents an anti-PERP chimeric antibody KM3481, ■ represents an anti-PERP CDR-modified antibody ver.1, ▲ represents an anti-PERP CDR-modified antibody ver.2, ◆ represents an anti-PERP CDR-modified antibody ver.3, ● represents an anti-PERP CDR-modified antibody ver.4, □ represents an anti-PERP CDR-modified antibody ver.5, Δ represents an anti-PERP CDR-modified antibody ver.6 and ○ is an anti-CCR4 chimeric antibody which is a negative control.

The result is shown in FIG. 3. An ordinate shows mean fluorescence intensity (MFI) and an abscissa shows an antibody concentration. All of the 6 kinds of modified antibodies were found to bind to PC9 cells and the strength of the binding was dependent on the concentration of the antibody.

(2) ADCC Activity of Modified Antibody

ADCC activity of the modified antibody produced in Example 1 was measured as follows. PC9 was used as a target cell, and lymphoprep (manufactured by Nycomed) was used for preparing an effector cell solution.

(2)-1 Preparation of the Target Cell Solution

Each cell line cultured using an RPMI 1640-FBS(10) medium [an RPMI 1640 medium containing 10% FCS (manufactured by Invitrogen)] was washed with RPMI 1640-FBS(5) [an RPMI 1640 medium containing 5% FBS (manufactured by Invitrogen)] by centrifugation and suspension and then the cell concentration was made $2 \times 10^5$ cells/mL using a medium for the measurement of ADCC activity to prepare a target cell solution.

(2)-2 Preparation of the Effector Cell Solution

Venous blood (50 mL) of a healthy person was collected, 0.5 mL of heparin sodium (manufactured by Shimizu Seiyaku) was added thereto, followed by stirring gently. A mononuclear cell (PBMC) fraction was separated therefrom using lymphoprep (manufactured by Nycomed) according to the instructions attached thereto. The separated PBMC fraction was centrifuged with a medium for the measurement of ADCC activity, washed three times and suspended appropriately to give an effector cell solution.

(2)-3 Measurement of ADCC Activity

50 μL of the target cell solution ($1 \times 10^4$ cells/well) was added to a 96-well U-shaped bottom plate (manufactured by Falcon). Thereafter, 50 μL of the effector cell solution prepared in (2)-2 (being diluted so as to give the ratio of the effector cells to the target cells 20:1) was added thereto. Then, the modified antibody was diluted with a medium for the measurement of ADCC activity and added thereto so that each final concentration was made 0.001 to 1 μg/mL and the total volume was made 150 μL, followed by reaction at 37° C. for 4 hours. After the reaction, the plate was centrifuged and a lactic acid dehydrogenase (LDH) activity of the supernatant was measured by obtaining the absorbance data using LDH-Cytotoxic Test (manufactured by Wako Pure Chemicals) according to the instructions attached thereto. The absorbance data for spontaneous release of target cells and for spontaneous release of effector cells were obtained by conducting the same operation described as above using a medium for the measurement of ADCC activity, instead of the effector cell solution/the antibody solution and instead of the target cell solution/the antibody solution, respectively. Absorbance data of the total release of target cells were obtained by such a manner that a medium for the measurement of ADCC activity was used, instead of the antibody solution and the effector cell solution and, 45 minutes before completion of the reaction, a reaction was carried out by addition of 15 μL of 9% Triton X-100 solution, followed by similar operation to the above. ADCC activity was determined by the following formula. In this connection, as a control, ADCC activity was measured by the following formula using the anti-PERP chimeric antibody KM3481 described in Reference Example 2.

ADCC activity(%)={(absorbance of sample−absorbance of spontaneous release of effector cells−absorbance of spontaneous release of target cells)/(absorbance of total release of target cells−absorbance of spontaneous release of target cells)}×100 (Formula)

Figure 4:
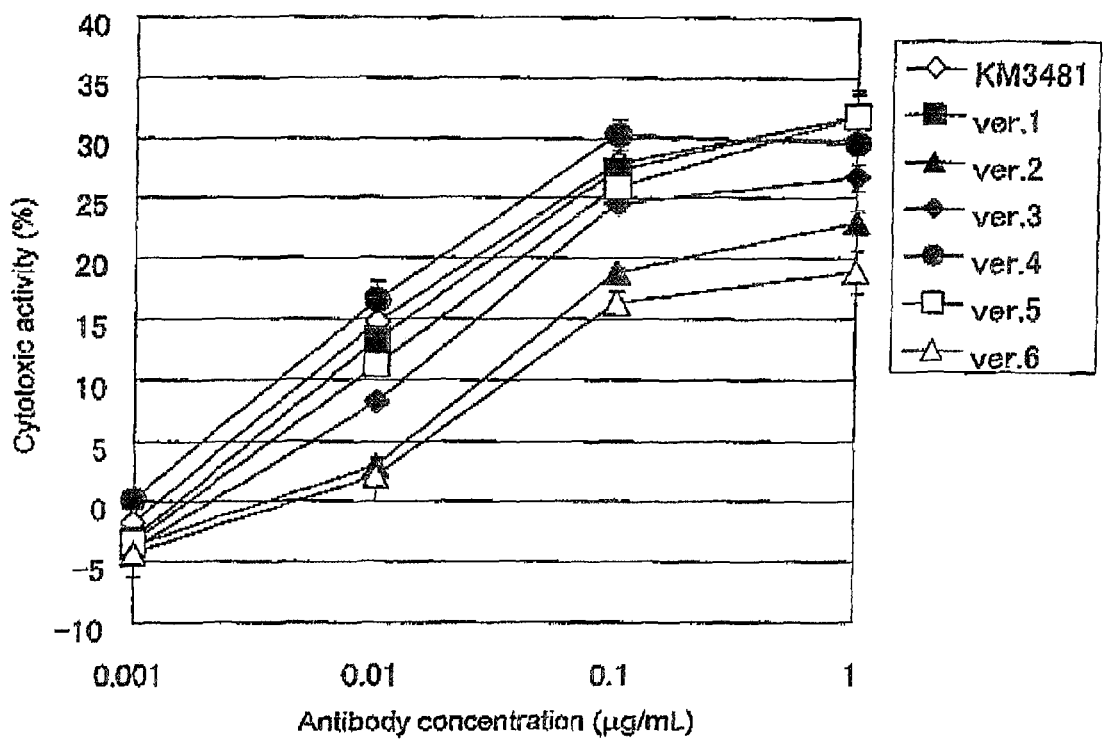
FIG. 4 shows an ADCC activity of each antibody. The ordinate and the abscissa in each drawing show cytotoxic activity (%) and antibody concentration, respectively. In the drawing, ◇ represents anti-PERP chimeric antibody KM3481, ■ represents an anti-PERP CDR-modified antibody ver.1, ▲ represents an anti-PERP CDR-modified antibody ver.2, ◆ represents an anti-PERP CDR-modified antibody ver.3, ● represents an anti-PERP CDR-modified antibody ver.4, □ represents an anti-PERP CDR-modified antibody ver.5 and Δ is an anti-PERP CDR-modified antibody ver.6.

The result is shown in FIG. 4. The modified antibody had ADCC activity against the PC9 cells, and the activity was dependent on the concentration of antibody.

EXAMPLE 3

Production of Anti-PERP Humanized Antibody Having No Consensus Sequence of an N-Linked Sugar Chain (1) Design of Amino Acid Sequences of VH and VL of an Anti-PERP Humanized Antibody Having No Consensus Sequence of an N-Linked Sugar Chain Firstly, an amino acid sequence of VH of the anti-PERP humanized antibody having no consensus sequence of an N-linked sugar chain was designed as follows.

Amino acid sequence of FR of VH of a human antibody was selected for grafting of CDR1 of an antibody VH having the amino acid sequence represented by SEQ ID NO:3, CDR2 of antibody VH having any one of amino acid sequences represented by SEQ ID NOs:4 and 6 to 10 and CDR3 of antibody VH having the amino acid sequence represented by SEQ ID NO:5. Kabat, et al. classified known various human antibody VH into three subgroups (HSG I to III) in view of homology of amino acid sequences thereof and reported a common sequence for each subgroup thereof [*Sequences of Proteins of Immunological Interest*, U.S. Dept. Health and Human Services (1991)]. In the common sequences, there is a possibility that, in humans, immunogenicity much more lowers and, therefore, it was planned to design the amino acid sequence of VH of the anti-PERP humanized antibody based on such common sequences. In order to prepare the anti-PERP humanized antibody having higher binding activity, in the design, among the amino acid sequences of FR of common sequences of the three subgroups of VH of a human antibody, an amino acid sequence of FR specifically recognizing the three-dimensional structure of the extracellular region of polypeptide encoded by the PERP gene and having the highest homology to the amino acid sequence of FR of VH of an anti-PERP mouse antibody KM3411 which is an anti-PERP monoclonal antibody bound to the extracellular region was selected.

The result of investigation of the homology was that homologies of HSG I, HSG II and HSG III were 54.0%, 74.7% and 60.9%, respectively. Accordingly, the amino acid sequence of FR of VH region of KM3411 had the highest homology to the subgroup II.

From the above result, the amino acid sequence of CDRs of VH of the anti-PERP mouse antibody KM3411 were grafted to an appropriate position of the amino acid sequence of FR of the common sequence of the subgroup II of VH of the human antibody. However, although Ile at position 47, Ile at position 86, Gln at position 100, Glu at position 107 and Thr at position 111 in the amino acid sequence of VH of KM3411 represented by SEQ ID NO:37 are not the amino acid residues most frequently used in the corresponding sites of the amino acid sequence of a human antibody FR described by Kabat, et al., they are still the amino acid residues which are used in a relatively high frequency and, therefore, the above-described amino acid residues found in the amino acid sequence of KM3411 were decided to be used. Thus, an amino acid sequence of VH of an anti-PERP humanized antibody comprising the amino acid sequence represented by any of SEQ ID NOs:30 to 35 was designed. In addition, from the results in Example 2, an antibody having the highest binding activity among the modified antibodies ver.1 to ver.6 having no consensus sequence of an N-linked sugar chain in V region was ver.4 and, therefore, the HV having CDR2 of a modified antibody ver.4 (hereinafter referred to as KM3821) having no consensus sequence of an N-linked sugar chain in V region was called HV0 (SEQ ID NO:33).

Next, an amino acid sequence of VL of the anti-PERP humanized antibody was designed as follows.

An amino acid sequence of FR of VL of a human antibody was selected for grafting of amino acid sequences of CDR1 to 3 of the antibody VL represented by SEQ ID NOs:11 to 13, respectively. Kabat, et al. classified various VL of a human antibody which has been known already into four subgroups (HSG I to IV) depending upon the homology of amino acid sequences thereof and also reported of the common sequence for each of such subgroups [*Sequences of Proteins of Immunological Interest*, U.S. Dept. of Health and Human Services (1991)]. Therefore, the same as in the case of VH, among the amino acid sequences of FR of common sequences of the four subgroups of VL of a human antibody, an amino acid sequence of FR specifically recognizing the dimensional structure of the extracellular region of polypeptide encoded by the PERP gene and having the highest homology to the amino acid sequence of FR of VL of the anti-PERP mouse antibody KM3411 which is the anti-PERP monoclonal antibody bound to the extracellular region was selected.

The result of investigation of the homology was that homologies of HSG I, HSG II, HSG III and HSG IV were 67.5%, 62.5%, 66.2% and 65.0%, respectively. Accordingly, the amino acid sequence of FR of VL of KM3411 had the highest homology to the subgroup I.

From the above results, the amino acid sequences of CDRs of VL of the anti-PERP mouse antibody KM3411 was grafted to an appropriate position of the amino acid sequence of FR of the common sequence of the subgroup I of VL of a human antibody and the amino acid sequence LV0 of the anti-PERP humanized antibody represented by SEQ ID NO:36 was designed.

The HV0 and the LV0 which are the amino acid sequences of VH and VL, respectively, of the anti-PERP humanized antibody designed hereinabove are the sequences wherein only amino acid sequences of CDRs of the anti-PERP mouse antibody KM3411 were grafted to the amino acid sequence of FR of the selected human antibody and, usually, it frequently occurs in producing a humanized antibody that, when amino acid sequences of CDRs of a mouse antibody are merely grafted to FR of a human antibody, its binding activity is decreased. In order to avoid the decreasing of the binding activity, it has been carried out that, among the amino acid residues of FR which are different between the human antibody and the mouse antibody, an amino acid residue which is thought to affect the binding activity is modified together with graft of the amino acid sequences of CDRs. Accordingly, in this Example, the amino acid residue which is thought to affect the binding activity was also identified as follows.

Firstly, the three-dimensional structure of an antibody V region (HV0LV0) comprising the amino acid sequence HV0 of VH and the amino acid sequence LV0 of VL of the anti-PERP humanized antibody designed hereinabove was constructed by means of a computer modeling. In producing the three-dimensional structure coordinate, a software AbM (manufactured by Oxford Molecular) and, in displaying the three-dimensional structure, a software Pro-Explore (manufactured by Oxford Molecular) or ViewerLite (manufactured by Accelrys) were used according to the instructions attached thereto. A computer model of the three-dimensional structure of V region of the anti-PERP mouse monoclonal antibody KM3411 was also constructed similarly. Furthermore, similarly a three dimensional structure model comprising an amino acid sequence where, in amino acid sequences of FR of VH and VL of HV0LV0, the amino acid residue being different from the anti-PERP mouse antibody KM3411 is successively modified to the amino acid residue found in the corresponding position of the anti-PERP mouse antibody KM3411 was constructed, and then the three dimensional structures of V region of anti-PERP mouse antibody KM3411, HV0LV0 and the modified antibody were compared.

As a result, with regard to the amino acid residue which is thought to change the three-dimensional structure of the antigen-binding site in the amino acid residues of FR of HV0LV0 and to affect the binding activity of the antibody, Gly at position 27, Ser at position 30, Pro at position 41, Lys at position 44, Gly at position 45, Ile at position 49, Val at position 72 and Ala at position 97 were selected in the case of HV0 while, in the case of LV0, Gln at position 3, Thr at position 5, Tyr at position 35, Ala at position 42, Leu at position 46, Phe at position 70 and Leu at position 77 were selected. Among the amino acid residues selected, at least one amino acid sequence was modified to an amino acid residue existing in the same site of the mouse antibody KM3411 to thereby design VH and VL of the humanized antibody having various modifications. More specifically, with regard to the antibody VH, at least one modification selected from amino acid modifications for substitutions of Gly at position 27 with Phe, Ser at position 30 with Thr, Pro at position 41 with Phe, Lys at position 44 with Asn, Gly at position 45 with Arg, Ile at position 49 with Met, Val at position 72 with Arg and Ala at position 97 with Thr was introduced into the amino acid sequence represented by any one of SEQ ID NOs:30 to 35, and with regard to VL, at least one modification selected from amino acid modifications for substitutions of Gln at position 3 with Val, Thr at position 5 with Ile, Tyr at position 35 with Phe, Ala at position 42 with Ser, Leu at position 46 with Trp, Phe at position 70 with Tyr and Leu at position 77 with Met was introduced into the amino acid sequence represented by SEQ ID NO:36.

(2) Construction of cDNA Encoding VH of the Anti-PERP Humanized Antibody cDNA encoding the amino acid sequence HV0 of VH of the anti-PERP Humanized antibody designed in (1) of this Example was constructed by using PCR as follows.

Firstly, the designed amino acid sequence was ligated to a secretory signal sequence of H chain of the anti-PERP mouse antibody KM3411 represented by positions 1 to 18 in SEQ ID NO:37 to give a full antibody amino acid sequence. Thereafter, the amino acid sequence was converted to genetic codon. When there are plural genetic codons for one amino acid residue, the corresponding genetic codon was determined by taking the frequency in use found in nucleotide sequences of genes of antibody [*Sequences of Proteins of Immunological Interest*, U.S. Dept. Health and Human Services (1991)] into consideration. The determined genetic codons were ligated to design the nucleotide sequence of cDNA encoding the amino acid sequence of the full antibody V region and, further, binding nucleotide sequences of primers for amplification upon the PCR (including restriction enzyme recognizing sequences for cloning to a vector for expression of humanized antibody) to 5'-terminal and 3'-terminal. The designed nucleotide sequences were divided into four nucleotide sequences in total each comprising about 100 nucleotides from the 5'-terminal side (in which, the adjacent nucleotide sequences were made to have duplicated sequences each comprising about 20 nucleotides at both ends thereof) and synthetic oligonucleotides (SEQ ID NOs:64 to 67) were synthesized in which the above were arranged in alternate order of sense chain and antisense chain.

Each of the oligonucleotides (SEQ ID NOs:64 to 67) was added to 50 μL of the reaction solution so as to give the final concentration 0.1 μmol/L and PCR was carried out using 0.5 μmol/L of M13RV primer (manufactured by Takara Shuzo), 0.5 μmol/L of M13M4 primer (manufactured by Takara Shuzo) and 1 unit of KOD polymerase (manufactured by Toyobo) according to the instructions attached to the KOD polymerase. The reaction conditions at that time followed the conditions described in the instructions (30 cycles, one cycle consisting of reaction at 94° C. for 30 seconds, 50° C. for 30 seconds and 74° C. for 60 seconds). The reaction solution was precipitated with ethanol, dissolved in sterile water, subjected to an appropriate treatment with a restriction enzyme and ligated to a plasmid pBluescript II SK(−) (manufactured by Stratagene). *Escherichia coli* DH5α was transformed by using the recombinant plasmid DNA solution produced, a plasmid DNA was produced from the transformant and a nucleotide sequence was analyzed using a BigDye Terminator Cycle Sequencing FS Ready Reaction Kit (manufactured by Applied Biosystems) to thereby produce a plasmid having the desired nucleotide sequence (SEQ ID NO:50).

Thereafter, modification of amino acid residues of FR designed in (1) of this Example was carried out by producing a synthetic oligonucleotide having modification, followed by the above PCR, or by carrying out PCR in which a plasmid DNA containing cDNA encoding HV0 produced hereinabove was used as a template and a synthetic DNA having modification was used as a primer, followed by isolation of the amplified gene fragments. With regard to genetic codon of the amino acid residue after the modification, the modification was carried out to obtain genetic codon found in the anti-PERP mouse antibody KM3411. Thereafter, unless otherwise indicated, the reaction was carried out by PCR of 35 cycles, one cycle consisting of reaction at 94° C. for 30 seconds, reaction at 55° C. for 30 seconds and reaction at 72° C. for 60 seconds. The PCR was carried out using a KOD-plus polymerase (manufactured by Toyobo). The synthetic oligo DNAs used hereinafter were manufactured by Fasmac. Hereinafter, the amino acid residue to be modified is shown by an alphabet and, on a right shoulder thereof, the amino acid residue number to be modified is described.

(a) Production of VH in which $G^{27}S^{30}P^{41}K^{44}G^{45}I^{49}V^{72}A^{97}$ was Modified to $F^{27}T^{30}F^{41}N^{44}R^{45}M^{49}R^{72}T^{97}$ (Hereinafter Referred to as HV8)

PCR was carried out by adding 0.1 μmol/L of synthetic DNAs having amino acid modifications (SEQ ID NOs:64, 69, 68 and 70) and 0.4 μmol/L of M13RV primer (manufactured by Takara Shuzo) and M13M4 primer (manufactured by Takara Shuzo) which were primers positioned at both terminals thereof. The reaction solution of PCR was purified using Gel Extraction Kit (manufactured by Qiagen) and subjected to 0.8 to 1.5% agarose gel electrophoresis and the desired gene fragments near 0.45 kbp were extracted using Gel Extraction Kit (manufactured by Qiagen). A subcloning was carried out for pBluescript II sk(−) (hereinafter referred to as pBS) treated with a specific restriction enzyme SmaI to thereby obtain a vector pBS/HV8 containing the desired gene (SEQ ID NO:51).

(b) VH in which $G^{27}P^{41}A^{97}$ was Modified to $F^{27}F^{41}T^{97}$ (Hereinafter Referred to as HV3)

In the same manner as in the above (a), PCR was carried out using synthetic DNAs (SEQ ID NOs:64, 79, 66 and 70) and M13Rv and M13M4 primers which were positioned at both terminals thereof to thereby obtain a vector pBS/HV3 containing the desired gene (SEQ ID NO:52).

(c) VH in which $G^{27}P^{41}V^{72}A^{97}$ was Modified to $F^{27}F^{41}R^{72}T^{97}$ (Hereinafter Referred to as HV4)

In the same manner as above, PCR was carried out using synthetic DNAs (SEQ ID NOs:64, 79, 80 and 70) and primers which were positioned at both terminals thereof to thereby obtain a vector pBS/HV4 containing the desired gene (SEQ ID NO:53).

(d) VH in which $G^{27}S^{30}P^{41}A^{97}$ was Modified to $F^{27}T^{30}F^{41}T^{97}$ (Hereinafter Referred to as HV4-2)

By using the pBS/HV3 produced in the above (b) as a template, PCR was carried out using the M13RV primer (manufactured by Takara Shuzo) and synthetic oligo DNA (SEQ ID NO:84) to obtain a gene fragment 5'-GS of about 0.3 kbp. Similarly, by using the pBS/HV3 as a template, PCR was carried out using synthetic oligo DNA (SEQ ID NO:85) and M13M20 primer to obtain a gene fragment 3'-PA of about 0.4 kbp. PCR was carried out using these gene fragments produced and M13RV and M13M20 primers, and Gel Extraction Kit (manufactured by Qiagen) was used to extract amplified gene fragments. Thereafter, an enzymatic treatment with specific restriction enzymes NotI and ApaI was carried out, electrophoresis with 0.8 to 1.5% agarose was carried out and desired gene fragments near 0.45 kbp were extracted using Gel Extraction Kit (manufactured by Qiagen). The extracted gene fragments were inserted into appropriate positions of the pBS to obtain a vector pBS/HV4-2 containing the desired gene (SEQ ID NO:54).

(e) VH in which $G^{27}S^{30}I^{49}V^{72}A^{97}$ was Modified to $F^{27}T^{30}M^{49}R^{72}T^{97}$ (Hereinafter Referred to as HV5-2)

By using the pBS/HV4-2 produced in the above (d) as a template, PCR was carried out using T3 primer (manufactured by Takara Shuzo) and synthetic oligo DNA (SEQ ID NO:86) to obtain 5'-GSPI gene fragments. By using the pBS/HV4 produced in the above (c) a template, PCR was carried out using T7 primer (manufactured by Takara Shuzo) and synthetic oligo DNA (SEQ ID NO:87) to obtain 3'-VA gene fragments. PCR was carried out using the produced gene fragments and T3 and T7 primers to obtain GSPIVA gene fragments of about 0.5 kbp. By using these gene fragments as templates, PCR was carried out using T3 primer and a synthetic oligo DNA (SEQ ID NO:92) to obtain 5'-HV5-2 fragments, and PCR was also carried out with T7 primer and a synthetic oligo DNA (SEQ ID NO:91) to obtain 3'-HV5-2 fragments. PCR was carried out using the two gene fragments produced and T3 and T7 primers and then a vector pBS/HV5-2 containing the desired gene (SEQ ID NO:55) was obtained in a manner similar to the above (c).

(f) VH in which $G^{27}P^{41}I^{49}V^{72}A^{97}$ was Modified to $F^{27}F^{41}M^{49}R^{72}T^{97}$ (Hereinafter Referred to as HV5-3)

By using the HV4 produced in the above (c) as a template, PCR was carried out using T3 primer (manufactured by Takara Shuzo) and a synthetic oligo DNA (SEQ ID NO:86) to obtain 5'-GPI gene fragments. Similarly, PCR was carried out using T7 primer (manufactured by Takara Shuzo) and a synthetic oligo DNA (SEQ ID NO:87) to obtain 3'-VA gene fragments. PCR was carried out using the produced gene fragments and T3 and T7 primers and then a vector pBS/ HV5-3 containing the desired gene (SEQ ID NO:56) was obtained in a manner similar to the above (c).

(3) Construction of cDNA Encoding VL of the Anti-PERP Humanized Antibody cDNA encoding the amino acid sequence of VL of the anti-PERP humanized antibody designed in (1) of this Example was constructed by PCR as follows.

Firstly, the designed amino acid sequence was ligated to a secretory signal sequence of L chain of the anti-PERP mouse antibody KM3411 represented by positions 1 to 22 of SEQ ID NO:38 to obtain a full antibody amino acid sequence. Thereafter, the amino acid sequence was converted to a genetic codon. When there are plural genetic codons for one amino acid residue, the corresponding genetic codon was determined by taking the frequency in use noted in nucleotide sequences of genes of antibody [*Sequences of Proteins of Immunological Interest*, U.S. Dept. Health and Human Services (1991)] into consideration. The determined genetic codons were ligated to design the nucleotide sequence of cDNA encoding the amino acid sequence of the full antibody V region and, further, binding nucleotide sequences for primers for amplification upon the PCR (including restriction enzyme recognizing sequences for cloning to the vector for expression of humanized antibody) to 5'-terminal and 3'-terminal. The designed nucleotide sequences were divided into four nucleotide sequences in total each comprising about 100 nucleotides from the 5'-terminal side (in which, the adjacent nucleotide sequences were made to have duplicated sequences each comprising about 20 nucleotides at both terminals thereof) and synthetic oligonucleotides (SEQ ID NOs: 71 to 74) were synthesized in which the above were arranged in alternate order of sense chain and antisense chain.

Each of the oligonucleotides (SEQ ID NOs:71 to 74) was added to 50 μL of the reaction solution so as to give the final concentration 0.1 μmol/L and PCR was carried out in a manner similar to the above (3) using 0.5 μmol/L of M13RV primer (manufactured by Takara Shuzo), 0.5 μmol/L of M13M4 primer (manufactured by Takara Shuzo) and 1 unit of KOD polymerase (manufactured by Toyobo) according to the instructions attached to the KOD polymerase. The reaction solution was precipitated with ethanol, dissolved in sterile water, subjected to an appropriate treatment with a restriction enzyme and ligated to a plasmid pBluescript II SK(–) (manufactured by Stratagene). *Escherichia coli* DH5α was transformed using the recombinant plasmid DNA solution produced as such, a plasmid DNA was produced from the strain of the transformant and a nucleotide sequence was analyzed using a BigDye Terminator Cycle Sequencing FS Ready Reaction Kit (manufactured by Applied Biosystems) to thereby obtain a plasmid pBS/LV0 having the desired nucleotide sequence (SEQ ID NO:57).

Thereafter, modification of amino acid residues of FR designed in (1) of this Example was carried out by producing a synthetic oligonucleotide having modification, followed by the above PCR, or by carrying out PCR in which a plasmid DNA containing cDNA encoding LV0 produced hereinabove was used as a template and a synthetic DNA having modification was used as a primer, followed by isolation of the amplified gene fragments. With regard to genetic codon of the amino acid residue after modification, the modification was carried out obtain genetic codon found in the anti-PERP mouse antibody KM3411.

Thereafter, unless otherwise indicated, the reaction was carried out by PCR of 35 cycles, one cycle consisting of reaction at 94° C. for 30 seconds, reaction at 55° C. for 30 seconds and reaction at 72° C. for 60 seconds. The PCR was carried out using a KOD-plus polymerase (manufactured by Toyobo). The synthetic oligo DNAs used hereinafter were manufactured by Fasmac. Hereinafter, the amino acid residue to be modified is shown by an alphabet and, on a right shoulder thereof, the amino acid residue number to be modified is mentioned.

(a) VL in which $G^3T^5Y^{35}A^{42}L^{46}F^{70}L^{77}$ was Modified to $V^3L^5F^{35}S^{42}W^{46}Y^{70}M^{77}$ (Hereinafter Referred to as LV7)

PCR was carried out by adding 0.1 μmol/L of synthetic DNA having amino acid modifications (SEQ ID NOs:75 to 78) and 0.4 μmol/L of M13RV primer (manufactured by Takara Shuzo) and M13M4 primer (manufactured by Takara Shuzo) which were primers positioned at both terminals thereof. The reaction solution of PCR was subjected to 0.8 to 1.5% agarose gel electrophoresis and the desired gene fragments near 0.4 kbp were extracted using Gel Extraction Kit (manufactured by Qiagen). A subcloning was carried out for pBluescript II sk(−) (hereinafter referred to as pBS) treated with a specific restriction enzyme SmaI to thereby obtain a vector pBS/LV7 containing the desired gene (SEQ ID NO:58).

(b) VL in Which $L^{46}F^{70}$ was Modified to $W^{46}Y^{70}$ (Hereinafter Referred to as LV2)

In a manner similar to the above (a), PCR was carried out using four synthetic oligo DNAs (SEQ ID NOs:71, 72, 81 and 74) and M13RV and M13M4 primers which were positioned at both terminals thereof and then a vector pBS/LV2 containing the desired gene (SEQ ID NO:59) was obtained in a manner similar to the above (a).

(c) VL in which $L^{46}F^{70}L^{77}$ was Modified to $W^{46}Y^{70}M^{77}$ (Hereinafter Referred to as LV3)

In a manner similar to the above (a), PCR was carried out using four synthetic oligo DNAs (SEQ ID NOs:71, 72, 81 and 78) and M13RV primer and M13M4 primer which were primers positioned at both terminals thereof and then a vector pBS/LV3 containing the desired gene (SEQ ID NO:60) was obtained in a manner similar to the above (a).

(d) VL in which $A^{42}L^{46}F^{70}$ was Modified to $S^{42}W^{46}Y^{70}$ (Hereinafter Referred to as LV3-2)

By using the pBS/LV2 produced in the above (b) as a template, PCR was carried out using M13RV primer and synthetic oligo DNA (SEQ ID NO:94) to obtain a gene fragment 5′-AL. Similarly, M13M20 primer (manufactured by Takara Shuzo) and a synthetic oligo DNA (SEQ ID NO:93) were used to obtain a 3′-F gene fragment. PCR was carried out using these gene fragments and M13RV and M13M20 primers and Gel Extraction Kit (manufactured by Qiagen) was used to extract amplified gene fragments. Thereafter, an enzymatic treatment with specific restriction enzymes EcoRI and BsiWI was carried out, electrophoresis with 0.8 to 1.5% agarose was carried out and the desired gene fragments of near 0.4 kbp were extracted using Gel Extraction Kit (manufactured by Qiagen). The extracted gene fragments were inserted into appropriate positions of the pBS wherein a restriction enzyme BsiWI recognition sequence was incorporated to obtain a vector pBS/LV3-2 containing the desired gene (SEQ I No. 61).

(e) VL in which $Y^{35}L^{46}F^{70}L^{77}$ was Modified to $F^{35}W^{46}Y^{70}M^{77}$ (Hereinafter Referred to as LV-4)

By using the pBS/LV3 produced in the above (c) as a template, PCR was carried out using T3 primer and synthetic oligo DNA (SEQ ID NO:90) to obtain a 5′-LV4 gene fragment. Similarly, PCR was carried out using T7 primer and synthetic oligo DNA (SEQ ID NO:89) to obtain a 3′-YLFL gene fragment. PCR was carried out using these gene fragments and T3 and T7 primers, and then a vector pBS/LV4 containing the desired gene (SEQ ID NO:62) was obtained in a manner similar to the above (d).

(f) VL in which $A^{42}L^{46}D^{69}F^{70}T^{71}$ was Modified to $S^{42}W^{46}S^{69}Y^{70}S^{71}$ (Hereinafter LV5-2)

By using the pBS/LV3-2 produced in the above (d) as a template, PCR was carried out using T7 primer and synthetic oligo DNA (SEQ ID NO:83) to obtain a 5′-DFT gene fragment. Similarly, PCR was carried out using T3 primer and synthetic oligo DNA (SEQ ID NO:82) to obtain a 3′-DFT gene fragment. PCR was carried out using these gene fragments and T7 and T3 primers, and then a vector pBS/LV5-2 containing the desired gene (SEQ ID NO:63) was obtained in a manner similar to the above (d).

Figure 11:
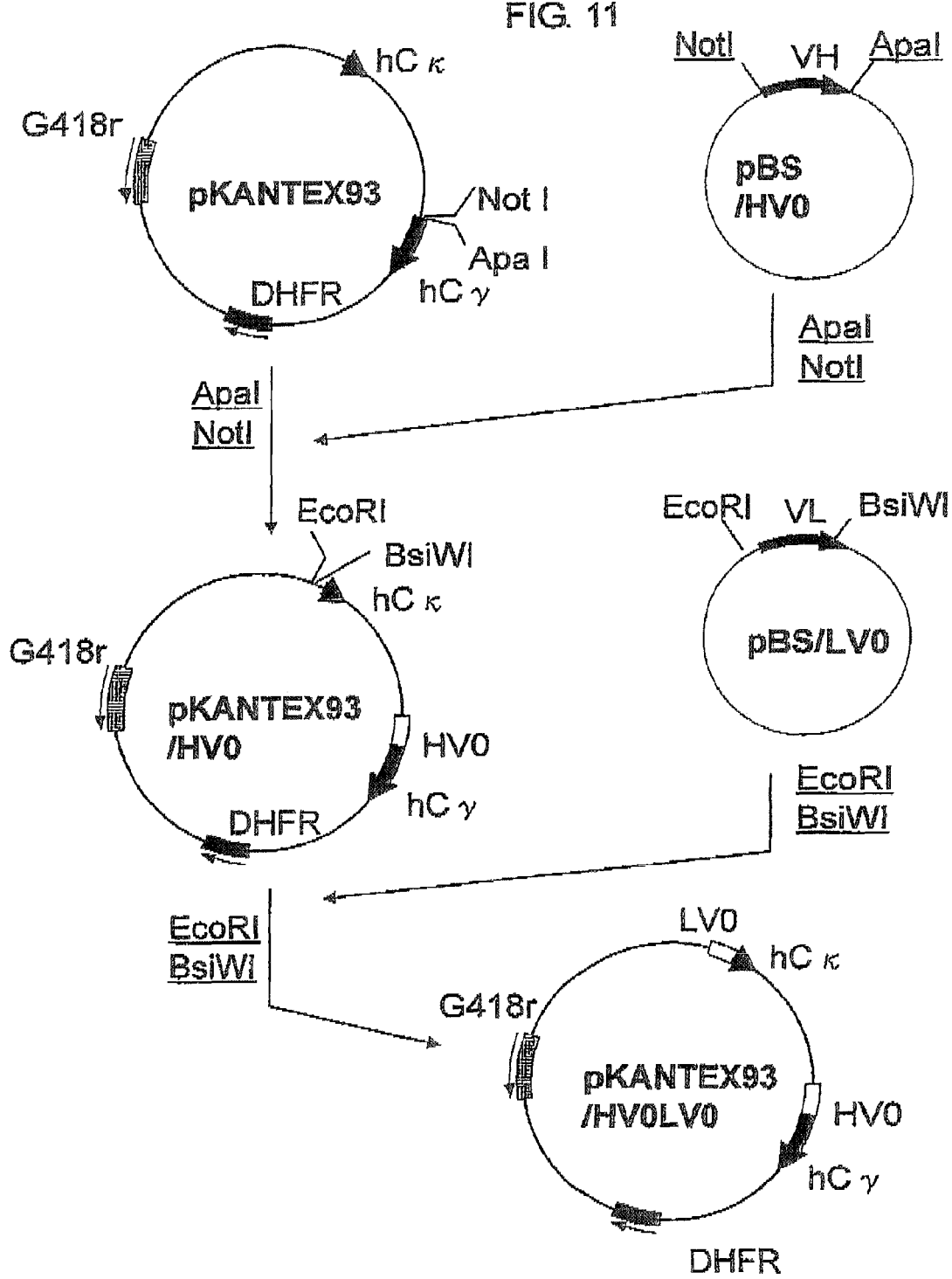
FIG. 11 shows construction steps of an anti-PERP humanized antibody.

(4) Construction of the Anti-PERP Humanized Antibody Expression Vector cDNA encoding each of HV0 and LV0 produced in Examples (2) and (3) or cDNA encoding each of modified gene thereof was inserted into an appropriate position of a vector pKANTEX93 for expression of humanized antibody described in WO97/10354 to construct various anti-PERP humanized expression vectors (FIG. 11).

Anti-PERP humanized antibodies having no consensus sequence of an N-linked sugar chain, 11 kinds of HV0LV0, HV8LV0, HV0LV7, HV4LV2, HV4LV3, HV8LV7, HV4LV7, HV4LV5-2, HV5-2LV4, HV5-3LV4 and HV4LV4, were produced.

(5) Stable Expression Using Animal Cells of the Anti-PERP Humanized Antibody and Obtaining of a Purified Antibody Stable expression using animal cells of anti-PERP humanized antibody and purification of the antibody from the supernatant of the culture were carried in a manner similar to the methods described in (2)-2 and (3) in Example 1.

EXAMPLE 4

Evaluation of Activity of the Anti-PERP Humanized Antibody Having No Consensus Sequence of an N-Linked Sugar Chain (1) Production of Human PERP (hPERP)-Expressing Cells A transformant of CHO/DG44 (KC861) was produced using pcPERPmH a manner similar to (1) of Reference Example 1. As a result, a transformant (KC1359) wherein hPERP is expressed in a medium degree and a transformant (KC9033) wherein it is expressed in a high degree were obtained.

(2) Binding Activity to PERP on the Membrane Surface (Fluorescent Antibody Technique)

Binding activity of an anti-PERP humanized antibody having no consensus sequence of an N-linked sugar chain purified in (5) of Example 3 to CHO/PERP (KC1359) expressing a polypeptide encoded by the PERP gene, or PC9 cells used in (1) of Example 1 was measured using a fluorescent antibody technique as described below.

CHO/PERP or PC9 cells (2 to $3 \times 10^5$ per well) were dispensed in a 96-well U-shaped plate, a modified antibody wherein the anti-PERP humanized antibody having no consensus sequence of an N-linked sugar chain was diluted in eight stages in a 2-fold dilution starting from 10 μg/ml using a buffer for FCM (1% BSA-PBS, 0.02% EDTA and 0.05% $NaN_3$) was dispensed in an amount of 100 μL/well or the modified antibody diluted in eight stages in a 5-fold dilution starting from 10 μg/ml and a reaction was carried out on ice for 30 minutes. After washing with a buffer for FCM once, a solution in which a PE-labeled anti-human IgG (H+L) antibody (manufactured by Beckmann-Coulter) diluted 50-fold with a buffer for FCM was added thereto in an amount of 100 μL/well. After the mixture was allowed to react for 30 minutes on ice protecting from the light, it was washed with a buffer for FCM twice and fluorescence intensity was measured using a flow cytometer. As a positive control, the anti-PERP human chimeric antibody KM3481 described in Reference Example 2 or the anti-PERP human chimeric antibody KM3821 (KM3821) having no consensus sequence of an N-linked sugar chain produced in Example 1 was used.

As a result, HV0LV0 in which CDR of KM3821 was merely grafted to a human framework and HV0LV7 in which amino acid modification was carried out in only L chain showed almost no binding activity but, in HV8LV0 in which amino acid modification was carried out in H chain, its binding activity increased to an extent of about ⅕ of KM3821 (FIG. 12-A). Further, in HV4LV2 and HV4LV3 in which amino acid modification residue numbers were decreased and amino acid modifications were carried out in both H chain and L chain, the binding activity increased to equal to that of HV8LV0 (FIG. 12-B).

Furthermore, in HV4LV7 and HV8LV7 in which amino acid modification residue numbers were increased, the binding activity increased compared with HV4LV3 and both antibodies had binding activity similar that of KM3821 (FIG. 13-A).

From these results, since there is a possibility that the amino acid modification of $G^3T^5Y^{35}A^{42}$ other than the amino acid modification residues $L^{46}F^{70}L^{77}$ of L chain modified of HV4LV3 or the amino acid modification of $S^{30}K^{44}G^{45}I^{49}$ other than the amino acid modification residues of $G^{27}P^{41}V^{72}A^{97}$ modified of HV4 relates to increase in the activity, binding activity of the anti-PERP humanized antibody in which further amino acid modification was carried out in VH was measured as follows.

The result was that, in all of HV5-2LV4, HV5-3LV4, HV4LV4 and HV4LV5-2, the activity increased than HV4LV3 having binding activity similar to KM3821 (FIG. 13-C). It became apparent that, among these, HV4LV4 having the least amino acid modification residue numbers was a variable region wherein an amino acid modification from $Y^{35}$ to $F^{35}$ of L chain was added to the amino acid modification of HV4LV3 and the modification of $Y^{35}$ greatly related to activity increase of the anti-PERP humanized antibody having no consensus sequence of an N-linked sugar chain. Also, the binding activity to human lung cancer cell line PC-9 has similar reactivity (FIG. 14-A, B, C).

(3) ADCC Activity of the Modified Antibody

ADCC activity of the modified antibodies, HV5-2LV4, HV5-3LV4, HV4LV4 and HV4LV5-2, was measured according to the following method.

(3-1) Preparation of Target Cell Solution

Human pancreatic cancer cell line BxPC-3 and human lung cancer cell line PC-9 were cultured using an RPMI 1640-FBS (10) medium [an RPMI 1640 medium (manufactured by Invitrogen) containing 10% FCS and 50 µg/mL of gentamicin], and human PERP expression CHO/DG44 cells (KC1359 and KC9033) were cultured using an IMDM-CHO medium [an IMDM medium (manufactured by Invitrogen) containing 10% FCS, 1×HT supplement (manufacture by Invitrogen), 50 µg/mL of gentamicin and 0.5 mg/mL of G418 (manufactured by Nacalai Tesque)]. Each cell was subjected to extended culturing and washed with RPMI 1640-FBS (1) [an RPMI 1640 medium (manufactured by Invitrogen) containing 1% FBS and containing no Phenol Red] which was a medium for measurement of ADCC activity by centrifugation and suspension, and a cell concentration was adjusted to $2\times10^5$ cells/mL by a medium for the measurement of ADCC activity to obtain a target cell solution.

(3-2) Preparation of Effector Cell Solution

Venous blood (50 mL) was collected from a healthy person, and 0.5 mL of heparin sodium (manufactured by Shimizu Seiyaku) was added thereto, followed by gently mixing. A monocyte (PBMC) fraction was separated from the mixture by using a Polymorphoprep (manufactured by Nycomed) according to the instructions attached thereto. The separated PBMC fraction was centrifuged by a medium for the measurement of ADCC activity, washed twice and appropriately suspended to obtain an effector cell solution.

(3-3) Measurement of ADCC Activity

The target cell solution (50 µL) ($1\times10^4$ cells/well) prepared in the above (2)-1 was dispensed in a 96-well U-shaped bottom plate (manufactured by Falcon). Then, 50 µL of the effector cell solution prepared in (2)-2 (which was diluted so as to give the ratio of the effector cells to the target cells 20:1) was added thereto. Further, 50 µL of the modified antibody which was diluted in eight stages in a 5-fold dilution starting from 3 µg/mL with a medium for the measurement of ADCC activity was added to give the total volume 150 µL, followed by reaction at 37° C. for 4 hours. After the reaction, the plate was centrifuged and measurement was carried out by obtaining the absorbance data of lactic acid dehydrogenase (LDH) in the supernatant using an LDH-Cytotoxic Test (manufactured by Wako Pure Chemicals) according to the instructions attached thereto. Absorbance data of spontaneous release of effector cells were obtained using a medium for the measurement of ADCC activity, instead of the effector cells solution and the antibody solution, and absorbance data of spontaneous release of effector cells were obtained using a medium for the measurement of ADCC activity, instead of the target cell solution and the antibody solution by carrying out operation similar to the above. Absorbance data of total release of target cells were obtained by using a medium for the measurement of ADCC activity, instead of the antibody solution and the effector cell solution, destroying cells by adding 20 µL of 9% Triton X-100 solution 45 minutes before the completion of the reaction and carrying out operation similar to the above. The ADCC activity was determined by the following formula. Also, KM3821 was used as a control and the ADCC activity was measured in a manner similar to Example 2.

As a result, HV8LV7, HV5-3LV4 and HV4LV4 produced at this time in which the binding activity to CHO/PERP was comparable to that of KM3821 had ADCC activity comparable to that of KM3821. Further, these antibodies had ADCC activity similar that of KM3821 for all target cells of human lung cancer cell line (FIG. 15), human pancreatic cancer cell line BxPC-3 (FIG. 16) and high CHO/PERP-expressing cell line (KC9033) (FIG. 17) have ADCC activity similar to KM3821. However, it was found that HV5-2LV4 has a tendency to have slightly lower ADCC activity than that of KM3821.

EXAMPLE 5

Epitope Analysis of KM3821 which Specifically Recognizes Three-Dimensional Structure of an Extracellular Region of a Polypeptide Encoded by the PERP Gene (1) Construction of Mutant PERP Expression Vector In order to modify the amino acid residues which are different with amino acid residues in mouse by comparing amino acid residues of an extracellular region loop 1 or loop 2 of human PERP and mouse PERP, each mutant PERP expression vector was produced (FIG. 18) by using the human PERP expression vector pcPERPmH produced in Reference Example 1 as a template and using a primer having an amino acid modification and a primer specific to pcDNA3.1+ vector (SEQ ID NO:112 or 113). Genetic codons of the amino acid residues after the amino acid residue modification, it were selected so as to give genetic codons found in the mouse PERP (accession No. NP_071315). Hereinafter, unless otherwise indicated, the reaction was carried out by PCR of 25 to 35 cycles, one cycle consisting of reaction at 94° C. for 30 seconds, reaction at 58° C. for 30 seconds and reaction at 72° C. for 60 seconds. The PCR was carried out using a KOD-plus polymerase (manufactured by TOYOBO). Also, hereinafter, the synthetic oligo DNAs used were manufactured by Fasmac. Hereinafter, the amino acid residue to be modified is shown by an alphabet and the amino acid residue number was described on the right shoulder thereof.

(a) Mutant PERP in which $D^{40}G^{42}K^{50}S^{52}Q^{53}E^{62}E^{63}$ was Modified to $N^{40}I^{42}R^{50}F^{52}D^{53}D^{62}D^{63}$ (Hereinafter Referred to as mL-1)

By using pcPERPmH produced in Reference Example 1 as a template, PCR was carried out using a primer positioned at the vector side (SEQ ID NO:112) and a synthetic oligo DNA containing mutation amino acid positioned in the PERP (SEQ ID NO:103), electrophoresis was carried out using 1.5% agarose and gene fragments of about 0.3 kbp were extracted with Gel Extraction Kit (manufactured by Qiagen) to obtain 5'-mL-1 gene fragments. Similarly, by using the pcPERPmH as a template, PCR was carried out using a primer positioned at the vector side (SEQ ID NO:113) and a synthetic oligo DNA containing mutation amino acid positioned in the PERP (SEQ ID NO:102) to obtain 3'-mL-1 gene fragments of about 0.7 kbp. PCR was carried out using the obtained gene fragments and primer (SEQ ID NOs:112 and 113) at the vector side and the amplified gene fragments of about 0.8 kbp were extracted with Gel Extraction Kit (manufactured by Qiagen). After the extraction, an enzymatic treatment was carried out using specific restriction enzymes EcoRI and XbaI and agarose electrophoresis was carried out to thereby extract gene fragments of about 0.7 kbp in a manner similar to the above. The obtained gene fragments were treated with restriction enzymes EcoRI and XbaI and inserted into an appropriate position of pcDNA3.1+ to prepare a vector pcDNA3.1+/mL-1 containing the desired gene (SEQ ID NO:96).

(b) Mutant PERP in which $T^{138}A^{141}T^{146}$ was Modified to $R^{138}D^{141}N^{146}$ (Hereinafter Referred to as mL-2)

In a manner similar to (a), primer positioned at the vector side (SEQ ID NO:112) and a synthetic oligo DNA containing mutation amino acid positioned in the PERP (SEQ ID NO:105) were used to prepare 5'-mL-2 gene fragments of about 0.6 kbp. On the other hand, a primer positioned at the vector side (SEQ ID NO:113) and a synthetic oligo DNA containing mutation amino acid positioned in the PERP (SEQ ID NO:104) were used to obtain 3'-mL-2 gene fragments of about 0.4 kbp. PCR reaction was carried out using the obtained gene fragments and primers at the vector side (SEQ ID NOs:112 and 113) to prepare a vector pcDNA3.1+/mL-2 containing the desired gene (SEQ ID NO: 97).

(c) Mutant PERP in which $D^{40}G^{42}K^{50}S^{52}Q^{53}E^{62}E^{63}T^{138}A^{141}T^{146}$ was Modified to $N^{40}I^{42}R^{50}F^{52}D^{53}D^{62}D^{63}R^{38}D^{141}N^{146}$ (Hereinafter Referred to as mPERP)

In a manner similar to (a), by using pcDNA3.1+/mL-2 produced in (b) as a template, PCR was carried out using primer positioned at the vector side (SEQ ID NO:112) and synthetic oligo DNA containing mutation amino acid positioned in the PERP (SEQ ID NO:103) to obtain 5'-mPERP gene fragments of about 0.3 kbp. Similarly, by using pcDNA3.1+/mL-2 as a template, PCR was carried out using primer positioned at the vector side (SEQ ID NO:113) and synthetic oligo DNA containing mutation amino acid positioned in the PERP gene (SEQ ID NO:102) to obtain 3'-mPERP gene fragments of about 0.7 kbp. PCR was carried out using the obtained gene fragments and primers at the vector side (SEQ ID NOs:112 and 113) to obtain a vector pcDNA3.1+/mPERP containing the desired gene (SEQ ID NO:98).

(d) Mutant PERP in which $D^{40}G^{42}$ was Modified to $N^{40}I^{42}$ (Hereinafter Referred to as DG)

In a manner similar to (a), 5'-DG gene fragments of about 0.35 kbp were produced using primer positioned at the vector side (SEQ ID NO:112) and a synthetic oligo DNA containing mutation amino acid positioned in the PERP gene (SEQ ID NO:107). On the other hand, 3'-DG gene fragments of about 0.7 kbp were produced using primer positioned at the vector side (SEQ ID NO:112) and synthetic oligo DNA containing mutation amino acid positioned in the PERP gene (SEQ ID NO:106). PCR was carried out using the obtained gene fragments and primers at the vector side (SEQ ID NOs:112 and 113) to obtain a vector pcDNA3.1+/DG containing the desired gene (SEQ ID NO:99).

(e) Mutant PERP in which $K^{50}S^{52}Q^{53}$ was Modified to $R^{50}F^{52}D^{53}$ (Hereinafter Referred to as KSQ)

In a manner similar to (a), 5'-KSQ gene fragments of about 0.4 kbp were produced using primer positioned at the vector side (SEQ ID NO:112) and synthetic oligo DNA containing mutation amino acid positioned in the PERP gene (SEQ ID NO:109). On the other hand, 3'-KSQ gene fragments of about 0.6 kbp were produced using a primer positioned at the vector side (SEQ ID NO:113) and synthetic oligo DNA containing mutation amino acid positioned in the PERP gene (SEQ ID NO:108). PCR was carried out using the obtained gene fragments and primers at the vector side (SEQ ID NOs:112 and 113) to prepare a vector pcDNA3.1+/KSQ containing the desired gene (SEQ ID NO:100).

(f) Mutant PERP in which $E^{62}E^{63}$ was Modified to $D^{62}D^{63}$ (Hereinafter Referred to as EE)

In a manner similar to (a), 5'-EE gene fragments of about 0.4 kbp were produced using a primer positioned at the vector side (SEQ ID NO:112) and synthetic oligo DNA containing mutation amino acid positioned in the PERP gene (SEQ ID NO: 111). On the other hand, 3'-EE gene fragments of about 0.6 kbp were produced using primer positioned at the vector side (SEQ ID NO:113) and synthetic oligo DNA containing mutation amino acid positioned in the PERP gene (SEQ ID NO:110). PCR was carried out using the resulting gene fragments and primers of vector side (SEQ ID NOs:112 and 113) to prepare a vector pcDNA3.1+/EE containing the desired gene (SEQ ID NO:101).

(2) Monkey PERP Gene Cloning

When a search was carried out for a *Macaca fascicularis* cDNA library from the National Institute of Infectious Diseases using the human PERP gene sequence as a search tool, it showed a high homology to cDNA clone (QmoA-11464) from the medulla oblongata of *Macaca fascicularis*. From the amino acid sequence (SEQ ID NO:116) expected from this gene, it was found that, in the monkey PERP extracellular loop 1 and loop 2, two amino acids were different in extracellular region of the human PERP. Therefore, the monkey PERP gene was cloned to produce the cells expressing the monkey PERP.

By using an expression vector pME18SFL3 containing the monkey PERP gene as a template, PCR was carried out using synthetic oligo DNAs containing the sequences of specific restriction enzymes EcoRI and HindIII (SEQ ID NOs:114 and 115) to thereby amplify the desired gene. The amplified gene fragments were treated with restriction enzymes EcoRI and HindIII. An expression vector pBS-mycHis in which Myc tag and His tag can be inserted into the C terminal of protein was treated with restriction enzymes EcoRI and HindIII so that insertion was carried out whereby the codons of amino acids appropriately meet to thereby produce pBS-PERP tag. Further, the expression vector pBS-PERP tag was subjected to a restriction enzyme treatment using restriction enzymes EcoRI and HindIII and the resulting gene fragments were inserted into EcoRI and HindIII sites of pcDNA3.1+ vector to thereby obtain a vector pcDNA3.1+/monPERP containing the desired monkey PERPmH (SEQ ID NO:117).

(3) Construction of Mutant PERP Expression Cells

Each expression vector produced in the above Example 5(1) and human PERP expression vector pcPERPmH produced in Reference Example 1 were subjected to gene introduction into CHO/DG44 (KC 861) by an electroporation method to prepare transformants. After the electroporation, mutant PERP expression cells acquiring a drug resistance to G 418 (manufactured by Nacalai Tesque) were produced. After the electroporation, G 418 (manufactured by Nacalai Tesque) was added in the final concentration of 0.6 mg/mL, followed by culturing for 10 to 20 days to thereby produce various transformants into which the mutant PERP was introduced, CHO/hPERP, CHO/mPERP, CHO/mL-1, CHO/mL-2, CHO/DG, CHO/KSQ and CHO/EE.

(4) Investigation in Reactivity of KM3821 to Human PERP Expression Cells or Mutant PERP Expression Cells Binding activity of the anti-PERP chimeric antibody having no consensus sequence of an N-linked sugar chain purified in (5) of Example 3 to the human PERP produced in the above (2) of Example 5 or mutant PERP transformant was carried out using a fluorescent antibody method as follows.

(5) Reaction of Anti-PERP Humanized Antibody Having No Consensus Sequence of an N-Linked Sugar Chain A solution (100 µL/well) in which each anti-PERP chimeric antibody having no consensus sequence of an N-linked sugar chain was diluted with a buffer for FCM (1% BSA-PBS, 0.02% EDTA and 0.05% NaN$_3$) to an extent of 10 µg/mL was dispensed to 1 to 3×10$^5$/well of each fresh transformant or the transformant which was subjected to the above intracellular staining treatment, followed by reaction on ice for 30 to 60 minutes. After washing with a buffer for FCM once, a solution in which a PE-labeled human IgG (H+L) antibody (manufactured by Beckman Coulter) was diluted 50-fold with a buffer for FCM was added thereto in an amount of 100 µL/well. After the reaction on ice protecting from the light for 30 to 60 minutes, the mixture was washed with a buffer for FCM twice and fluorescent intensity was measured using a flow cytometer.

Reactivity of KM3821 to each mutant PERP in an extracellular staining in FIG. 19 was shown in terms of reactivity (%) to each mutant PERP or monkey PERP wherein the reactivity of KM3821 to hPERP was defined 100%.

As a result, KM3821 did not react at all with mPERP having an extracellular region of the mouse PERP and with mL-1 wherein only loop 1 of extracellular region of PERP was the amino acids in mouse, but reacted with mL-2 wherein only loop 2 of PERP extracellular region was the amino acids in mouse, so that it was apparent that KM3821 reacts with loop 1 of an extracellular region of the human PERP (FIG. 19). Further, although KM3821 reacted with KSQ wherein position 50, position 52 and position 53 corresponding to central part of loop 1 of extracellular region of PERP were amino acids of mouse, reactivity of KM3821 decreased to an extent of 1/10 or less to DG wherein position 40 and position 42 were the amino acids in mouse in comparison with the reactivity to hPERP and, in the case of EE wherein position at 62 and position 63 were the amino acids in mouse, reactivity of KM3821 also decreased to an extent of about 1/3 in comparison with hPERP (FIG. 19).

On the other hand, in KM3821, the amino acid at position 42 in loop 1 of extracellular region of PERP and the amino acid at position 138 in loop 2 reacted with the monkey PERP (where the amino acids were different from those of the human PERP) in the same manner as in hPERP and, therefore, it is likely that the amino acids at positions 42 and 138 have little affection to the binding of KM3821 to hPERP.

From the above result, it was clarified that KM3821 strongly recognized Asp at position 40 in loop 1 of an extracellular region of the human PERP and that recognized the three-dimensional structure comprising this amino acid residue, Glu at position 62 and Glu at position 63 (FIG. 19 and FIG. 20).

REFERENCE EXAMPLE 1

Production of the Anti-PERP Monoclonal Antibody Which Specifically Recognizes Three-Dimensional Structure of an Extracellular Region of a Polypeptide Encoded by the PERP Gene and Binds to the Extracellular Region (1) Production of PERP Expression Cells A solution containing 1 µL of a human PERP gene-containing plasmid HEMBA 1006335 (GenBank Accession No. AK 074585, 1 ng/µL), 2 µL of 10×ExTaq buffer, 2 µL of 2 mmol/L dNTP, each of 2 µL of 10 µmol/L of primers consisting of nucleotide sequences represented by SEQ ID NO:7 and SEQ ID NO:8, 0.5 µL of ExTaq polymerase (manufactured by Takara Shuzo) and 10.5 µL of sterile water was heated at 94° C. for 5 minutes and reaction was carried out by 25 cycles, one cycle consisting of reaction at 94° C. for 30 seconds, reaction at 65° C. for 30 seconds and reaction at 72° C. for 1 minute, followed by reaction at 72° C. for 7 minutes. The reaction product was separated by agarose gel electrophoresis and an amplified fragment of about 0.6 kb was extracted with Geneclean Spin Kit (manufactured by BIO 101). The fragment was ligated with pCRII-TOPO vector using TOPO TA cloning kit (manufactured by Invitrogen) and *Escherichia coli* DH5α was transformed by a method of Cohen, et al. [*Proc. Natl. Acad. Sci., USA,* 69, 2110 (1972)]. A plasmid was extracted from the resulting transformant using a plasmid extraction kit (manufactured by Qiagen) to obtain plasmid pCRII-PERP containing the human PERP gene.

As a cloning vector to add myc-His tag sequence to the 3'-terminal of the PERP fragment, pBSmH was produced as follows.

pcDNA 3.1(−)/myc-His C (manufactured by Invitrogen) was digested with PmeI and, by the same method as above, a DNA fragment containing a gene encoding myc-His tag of about 170 bp was obtained. The fragment was ligated using a DNA ligation kit ver.2 (manufactured by Takara Shuzo) to pBluescript II SK (−) (manufactured by Stratagene) in which its terminal was blunted with T4 DNA polymerase (manufactured by Takara Shuzo) after digesting with XbaI and KpnI, and then *Escherichia coli* DH5α was transformed. A plasmid was extracted from the resulting transformant with a plasmid extracting kit (manufactured by Qiagen) to prepare plasmid pBSmH. The pBSmH plasmid was digested with a restriction enzyme XbaI to give two fragments of about 2.9 kbp and about 160 kbp.

The above pCRII-PERP was digested with EcoRI and XbaI to obtain a fragment containing the PERP gene. The fragment was ligated by a DNA ligation kit ver.2 (manufactured by Takara Shuzo) to pBSmH digested with EcoRI and XbaI and then *Escherichia coli* DH5α was transformed. A plasmid was extracted from the resulting transformant with a plasmid extracting kit (manufactured by Qiagen) to obtain plasmid pBS-PERPmH.

pBS-PERPmH was digested with EcoRI and HindIII to prepare a fragment containing a gene encoding the PERP gene and myc-His tag. The fragment was ligated by a DNA ligation kit ver.2 (manufactured by Takara Shuzo) to pcDNA 3.1+ (manufactured by Invitrogen) digested with EcoRI and HindIII and then *Escherichia coli* DH5α was transformed. A plasmid was extracted from the resulting transformant with a plasmid extracting kit (manufactured by Qiagen) to give plasmid pcPERPmH which was an expression plasmid of human PERP.

The pcPERPmH was introduced into CHO/DG44 cells [*Somatic Cell and Molecular Genetics*, 12(6), 555 (1986)] according to an electroporation method [*Cytotechnology*, 3, 133 (1990)] as follows.

The cells which were cultured in an IMDM medium (manufactured by Life Technology) to which 10% fetal bovine serum (manufactured by Life Technology), 1×HT supplement (manufactured by Life Technology) and 1% penicillin-streptomycin (manufactured by Life Technology) were added (hereinafter referred to as "A3 medium") were used. The CHO/DE44 cells were suspended in a K-PBS buffer (137 nmol/L potassium chloride, 2.7 nmol/L sodium chloride, 8.1 mmol/L disodium monohydrogen phosphate, 1.5 nmol/L monosodium dihydrogen phosphate and 4 mmol/L magnesium chloride buffer) to obtain a concentration of $8 \times 10^6$ cells/mL and the cell suspension was mixed with 4 μg of the above-described expression plasmid pcPERPmH. The mixed solution was transferred to a cuvette (distance between electrodes: 2 mm) and gene introduction was carried out using a Gene Pulser II apparatus (manufactured by Biorad) under such conditions that the pulse voltage was 0.35 kV and the electric capacity was 250 μF. The cuvette was allowed to stand on ice and then the cell suspension in the cuvette was suspended in A3 medium and cultured at 37° C. in a 5% $CO_2$ incubator. After the culturing for one day, the medium was exchanged to A3 medium to which 0.5 mg/mL of G418 (manufactured by Carbiochem) was added, followed by culturing. During the culturing, dilution was carried out and subculture was continued and, after about two weeks from introduction of the gene, a transformant cell line having resistance to G418 was produced.

The resulting transformant cells were diluted with A3 medium to which 0.5 mg/mL of G418 was added to give a cell density of 1.25 cells/mL, 200 μL thereof was dispensed in each of a 96-well plate and cloning by a limiting dilution method was carried out.

The resulting transformant cells (1 to $5 \times 10^5$ cells) were dissolved in 15 μL of 1×PAGE buffer, heated at 95° C. for 5 minutes, fractionated by SDS-polyacrylamide electrophoresis [*Antibodies—A Laboratory Manual* (Cold Spring Harbor Laboratory, 1988)] and blotted to a PVDF membrane. After blocking with BSA-PBS, reaction with anti-myc monoclonal antibody 9E10 (manufactured by MBL) was carried out at room temperature for 1 hour. After washing with Tween-PBS, reaction with a peroxidase-labeled anti-mouse immunoglobulin antibody (manufactured by Dako) as the second antibody was carried out at room temperature for 1 hour. After sufficiently washing it with Tween-PBS, detection was carried out using an ECL-detection kit (manufactured by Amersham), followed by photosensitizing on an X-ray film.

Figure 5:
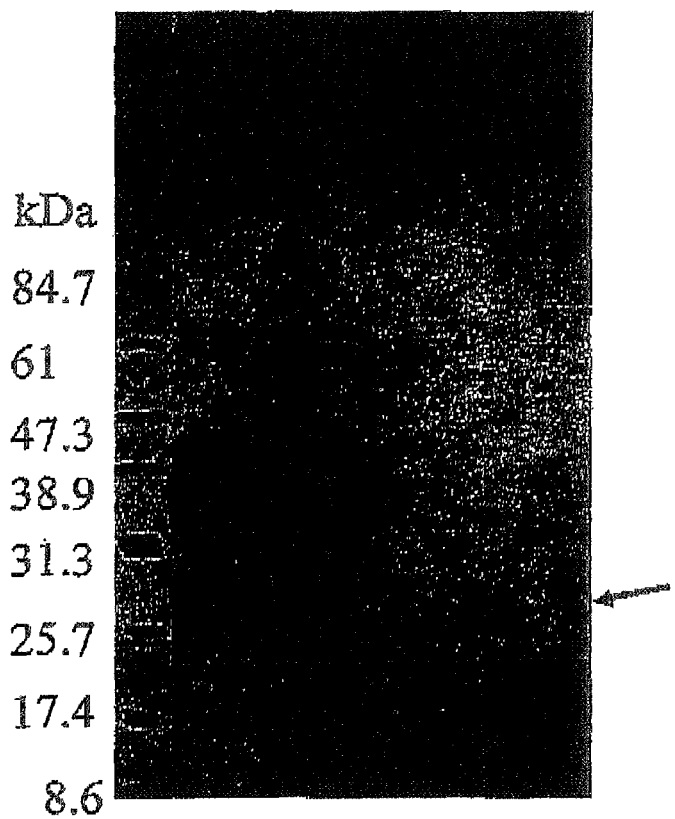
FIG. 5 shows the result of PERP expression for each clone of cells into which the PERP gene is introduced by Western blotting using an anti-Myc antibody. Clone numbers in the drawing show each clone of 4 kinds of PERP/CHO cells. PERP-negative cell shows CHO/DG44 cell into which no gene is introduced. The arrow in the drawing shows about 25 kDa which is a molecular weight of a polypeptide chain encoded by the PERP gene.

The result is shown in FIG. 5. A cell line in which a signal was recognized around the molecular weight of 25 kDa was designated as a PERP-expressing cell line (hereinafter referred to as "PERP/CHO cell").

(2) Production of Anti-PERP Monoclonal Antibody (2)-1 Production of Immunogen

The PERP-expressing cell line produced in the above (1) was cultured on an Iscove's Modified Dulbecco's medium containing 10% fetal bovine serum (manufactured by Invitrogen) for 2 to 3 days and suspended in PBS to obtain cell numbers per mouse of $6 \times 10^6$ to $1 \times 10^7$ cells.

(2)-2 Immunization of the Animals and Preparation of Antibody-Producing Cells

The cells produced in (2)-1 of Reference Example 1 were administered to 3 female Balb/c mice 6 weeks old together with $1 \times 10^9$ cells of pertussis vaccine (manufactured by Serum Laboratory in Chiba Prefecture). After one week from the administration, administrations were carried out once a week 5 times in total. Blood was partially collected from the fundus of eye of the mice, an antibody titer thereof in the blood was measured by an immunofluorescent staining method using the following cells by FMAT 8100 HTS system (manufactured by Applied Biosystem) and a flow cytometer (manufactured by Beckman Coulter) and, after 3 days from the final immunization, spleens were excised from the mice in which a sufficient antibody titer was obtained.

The spleen was finely cut in MEM (minimum essential medium) medium (manufactured by Nissui Pharmaceutical), loosened by tweezers and centrifuged (250×g for 5 minutes). To the resulting precipitation fraction was added a Tris-ammonium hydrochloride buffer (pH 7.6) and reaction was carried out for 1 to 2 minutes to remove erythrocytes. The resulting precipitate fraction (cell fraction) was washed 3 times with MEM and used for cell fusion.

(2)-3 Fluorescent Antibody Staining Method Using Cells (FMAT: Fluorometric Microvolume Assay Technology)

With regard to the cells for the assay, PERP/CHO cells and CHO/DG44 cells produced in (1) of Reference Example 1 were used. The cells which were cultured on an Iscove's Modified Dulbecco's medium containing 10% fetal bovine serum (manufactured by Invitrogen) for 2 to 3 days and peeled off with a Tripsin-EDTA solution (manufactured by Invitrogen) were suspended on the same medium, seeded onto a black 96-well plates for FMAT at $7 \times 10^3$ cells/100 μL medium/well and cultured overnight. Mouse anti-serum to be immunized or cultured supernatant of hybridoma cells was dispensed into the plate at 5 μL/well as a primary antibody, and ALEXA 647-labeled anti-mouse immunoglobulin G (H+L) (manufactured by Molecular Probe) was dispensed at 50 μL/well as a secondary antibody, and the plate was allowed to stand for 4 hours under shading the light. Wavelength of 650 to 685 nm excited by laser beam of 633 nm He/Ne was measured by an FMAT 8100 HTS system (manufactured by Applied Biosystem).

(2)-4 Fluorescent Antibody Staining Method Using Cells (Flow Cytometry)

As the cells for the assay, PERP/CHO cells and CHO/DG44 cells produced in (1) of Reference Example 1 were used. Cells which were cultured on an Iscove's Modified Dulbecco's medium containing 10% fetal bovine serum (manufactured by Invitrogen) for 2 to 3 days and peeled off with a 0.02% EDTA solution (manufactured by Nacalai Tesque) were washed with PBS and, in order to avoid the non-specific adsorption of antibody, they were blocked for 20 minutes at ice temperature using BSA-PBS. They were dispensed into a 96-well U-shaped plate so as to give a density of $1 \times 10^6$ cells/100 μL/BSA-PBS, followed by centrifugation (1,800 rpm for 2 minutes), then supernatant was removed and mouse anti-serum to be immunized or cultured supernatant of hybridoma cells was dispensed at 50 μL/well as a primary antibody, followed by reaction at ice temperature for 30 minutes. Washing was carried out 3 times by a centrifugation method using PBS and ALEXA 488-labeled anti-mouse immunoglobulin G (H+L) (manufactured by Molecular Probe) was dispensed at 20 μL/well as a secondary antibody, followed by reaction at ice temperature for 30 minutes under shading the light. Washing with PBS was carried out once again, followed by suspension in PBS, and wavelength of 510 to 530 nm excited with laser beam of 488 nm Ar was measured by a flow cytometer (manufactured by Beckman Coulter).

(2)-5 Production of Mouse Myeloma Cells

8-Azaguanine-resistant mouse myeloma cell line P3X63Ag8U.1:P3-U1 [ATCC CRL-1597: *European Journal of Immunology*, 6, 511 (1976)] was cultured on a normal medium (RPMI medium to which 10% fetal bovine serum was added) and $2\times10^7$ cells or more were ensured upon cell fusion and used for cell fusion.

(2)-6 Production of Hybridoma

The mouse splenic cells obtained in the above (2)-2 and the myeloma cells obtained in (2)-5 were mixed to give a ratio of 10:1 and centrifuged (250×g for 5 minutes), the supernatant was discarded, the precipitated cells were well loosened, then a mixed solution of 2 g of polyethylene glycol 1000 (PEG-1000), 2 ml of MEM medium and 0.7 mL of dimethyl sulfoxide were added thereto at 0.2 to 1 mL/$10^8$ mouse spleen cells under stirring at 37° C., 1 to 2 mL of MEM medium was added thereto several times every 1 to 2 minutes and MEM medium was added to give a total volume of 50 mL. After centrifugation (900 rpm for 5 minutes), the supernatant was discarded and the cells were gently loosened and gently suspended in 100 mL of an HAT medium by suction and sucking out using a measuring pipette.

The suspension was added to a 96-well culture plate at 200 μL/well and cultured in a 5% $CO_2$ incubator at 37° C. for 10 to 14 days. After the culturing, the culture supernatant was examined by the immunofluorescent staining methods described in (2)-3 and (2)-4 of this Reference Example, wells which reacted with PERP/CHO cells and did not react with CHO/DG44 cells were selected, cloning was repeated twice by a limiting dilution method from the cells contained therein and an anti-PERP antibody-producing hybridoma KM3411 (FERM BP-8643) was established.

Figure 6:
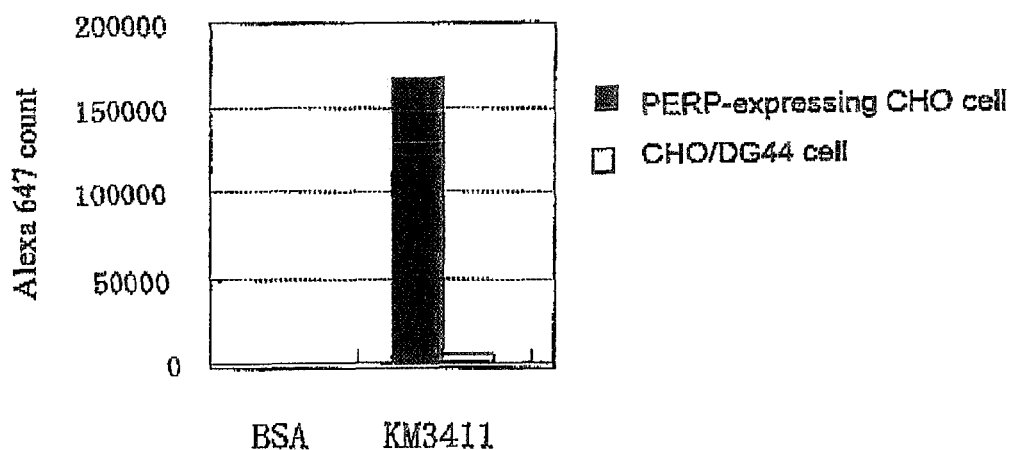
FIG. 6 shows reactivity of KM3411 in FMAT. In the graph, the ordinate shows the accumulated value of fluorescence intensity and cell numbers.

FIG. 6 shows reactivity of monoclonal antibody contained in the culture supernatant of hybridoma KM3411 to PERP/CHO cells and CHO/DG44 cells by an FMAT method. The monoclonal antibody KM3411 produced by the hybridoma KM3411 specifically reacts only with the PERP/CHO cells.

(2)-7 Purification of Monoclonal Antibody

The hybridoma obtained in (2)-5 of Reference Example 1 was intraperitoneally injected at 5 to $20\times10^6$ cells/mouse into each of the pristane-treated female nude mice 8 weeks old (BALB/c). After 10 to 21 days, ascites were collected (1 to 8 mL/mouse) from the mice in which ascites were stored as a result of the fact that the hybridoma became ascites cancer.

The ascites were centrifuged (1,200×g for 5 minutes) to remove the solid. Pure IgG monoclonal antibody was produced by purification using a caprylic acid precipitation method [*Antibodies—A Laboratory Manual*, Cold Spring Harbor Laboratory (1988)]. When a subclass of the purified anti-PERP mouse antibody KM3411 was decided by ELISA using a subclass typing kit, the subclass of the anti-PERP mouse antibody KM3411 was IgG1.

(2)-8 Investigation of Reactivity of Monoclonal Antibody—Fluorescent Cell Staining (Flow Cytometry)

Figure 7:
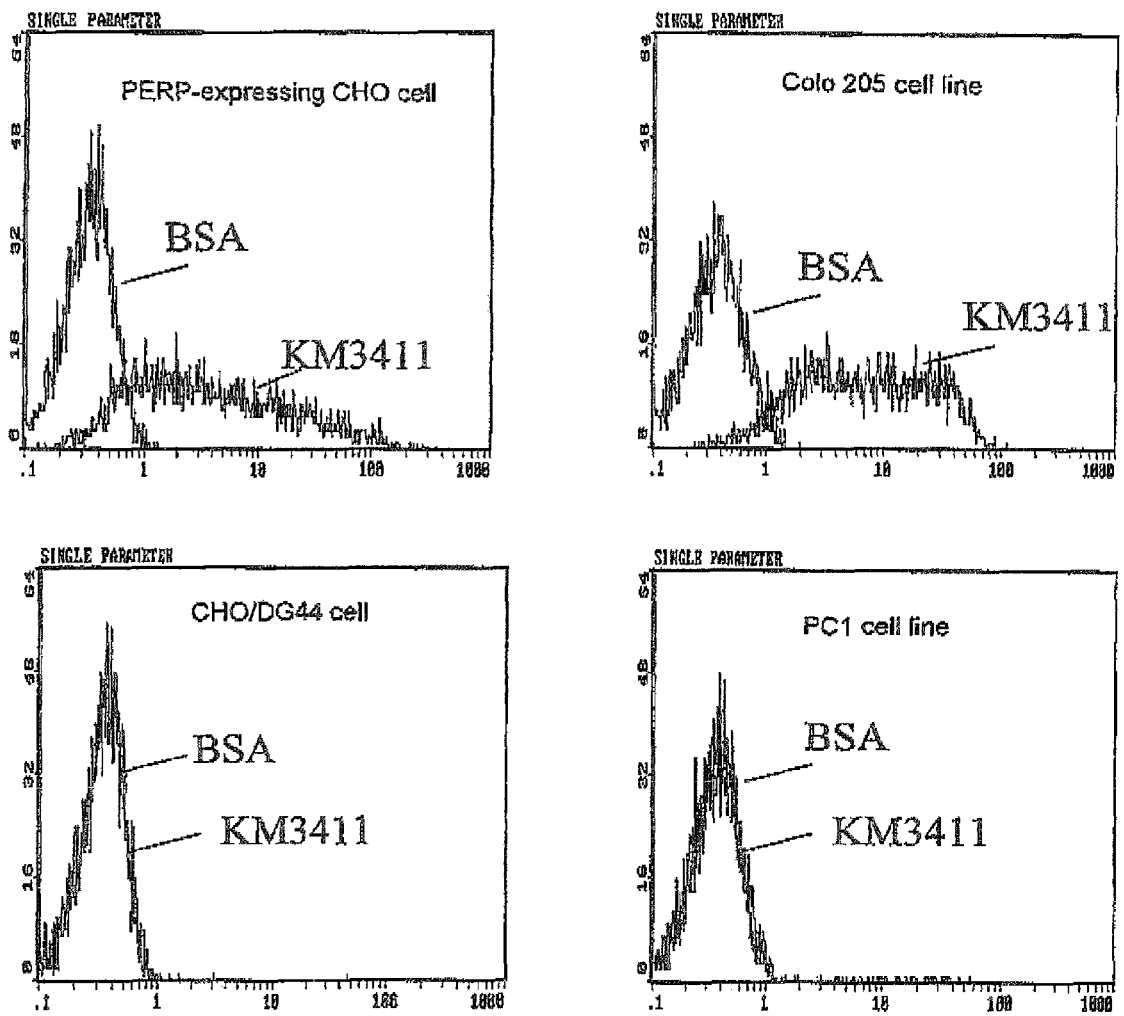
FIG. 7 shows reactivity of KM3411 in flow cytometry. The ordinate and the abscissa in each drawings show cell numbers and fluorescence intensity, respectively.

The experiment was carried out according to the method described in the above (2)-4. The result is shown in FIG. 7. KM3411 reacted with PERP/CHO cells and colorectal cancer cell line Colo 205 and did not react with CHO/DG44 cells and PC1 in which PERP mRNA was not expressed.

REFERENCE EXAMPLE 2

Production of Anti-PERP Chimeric Antibody which Specifically Recognizes Three-Dimensional Structure of an Extracellular Region of a Polypeptide Encoded by the Perp Gene and Binds to the Extracellular Region (1) Isolation and analysis of cDNA Encoding Variable Region of Anti-PERP Mouse Antibody which Specifically Recognizes Three-Dimensional Structure of an Extracellular Region of a Polypeptide Encoded by the PERP Gene and Binds to the Extracellular Region (1)-1 Production of mRNA from Anti-PERP Mouse Antibody-Producing Hybridoma From the hybridoma KM3411 described in Reference Example 1, about 39 μg (from $4\times10^7$ hybridoma cells) of mRNA was produced using Fast Track 2.0 Kit (manufactured by Invitrogen) which was a kit for preparation of mRNA according to the manufacture's instructions attached thereto.

(1)-2 Gene Cloning of H-Chain and L-Chain Variable Regions of Anti-PERP Mouse Antibody KM3411 mRNA (1 μg) of the anti-PERP mouse antibody KM3411 produced in the above (1)-1 was subjected to BD SMART™ RACE cDNA Amplification Kit (manufactured by BD Biosciences) in accordance with the manufacture's instructions attached thereto to give cDNA having the sequence of BD SMART II™ Oligonucleotide attached to the kit at the 5'-terminal. The cDNA was used as a template and PCR was carried out using a universal primer Amix attached to the kit and a mouse Ig(γ)-specific primer represented by SEQ ID NO:41 so that the cDNA fragment of VH was amplified. Another PCR was carried out using a mouse Ig(κ)-specific primer represented by SEQ ID NO:42 in place of the Ig(γ)-specific primer to amplify the cDNA fragment of VL.

PCR was carried out by heating at 94° C. for 45 minutes; 5 cycles, one cycle consisting of reaction at 94° C. for 15 seconds and reaction at 72° C. for 3 minutes; 5 cycles, one cycle consisting of reaction at 94° C. for 15 seconds, reaction at 70° C. for 30 seconds and reaction at 72° C. for 3 minutes; and 30 cycles, one cycle consisting of reaction at 94° C. for 15 seconds, reaction at 68° C. for 30 seconds and reaction at 72° C. for 3 minutes, followed by reaction at 72° C. for 10 minutes. The PCR was carried out using a GeneAmp PCR System 9700 (manufactured by Applied Biosystems). The resulting PCR product had a size of about 500 bp in each of the H chain and the L chain.

In order to determine the nucleotide sequence of the resulting PCR product, about 0.05 pmol of DNA produced by digesting pBluescript II SK(−) vector (manufactured by Stratagene) with SmaI and about 0.5 pmol of each of the PCR products produced above were added to 6 μL of Solution I of Takara DNA Ligation Kit, ver.2 (manufactured by Takara Shuzo) and 0.3 μL of a restriction enzyme SmaI to give a total volume of 12.3 μL, followed by reaction at 22° C. overnight. *Escherichia coli* DH5α (manufactured by TOYOBO) was transformed using the thus obtained recombinant plasmid DNA solution. Each plasmid DNA was produced from the clone of the transformant, followed by reaction using a Big Dye Terminator Cycle Sequencing FS Ready Reaction Kit (manufactured by PE Biosystems) according to the manufacture's instructions attached thereto and then the nucleotide sequence was analyzed using a sequencer ABI PRISM 3700 manufactured by the same company. As a result, a plasmid pKM3411H#9 containing a full-length H chain cDNA and a plasmid pKM3411L#4 containing an L-chain cDNA in which ATG sequence presumed to be an initiation codon was present at the 5' terminal of cDNA were produced.

(1)-3 Analysis of Amino Acid Sequence of V Region of the Anti-PERP Mouse Antibody A full length of nucleotide sequence contained in the plasmid pKM3411H#9 is represented by SEQ ID NO:43, a full length of amino acid sequence of a secretory VH containing a signal sequence deduced from the above sequence is represented by SEQ ID NO:37, a full length of nucleotide sequence of VL contained in the plasmid pKM3411L#4 is represented by SEQ ID NO:44 and a full length of amino acid sequence of a secretory VL containing a signal sequence deduced from the above sequence is represented by SEQ ID NO:38. From the comparison with sequence data of known mouse antibodies [*SEQUENCES of Proteins of Immunological Interest*, U.S. Dept. Health and Human Services (1991)] and from the comparison with the result of analysis of the N-terminal amino acid sequences in the H chain and the L chain of the purified anti-PERP mouse antibody KM3411 using a protein sequencer (PPSQ-10 manufactured by Shimadzu), it has been clear that each of the isolated cDNAs is a full-length cDNA encoding the anti-PERP mouse antibody KM3411 containing a secretory signal sequence; in the H chain, the amino acid sequence from positions 1 to 18 in the amino acid sequence represented by SEQ ID NO37 is the secretory signal sequence; and, in the L chain, the amino acid sequence from positions 1 to 22 in the amino acid sequence represented by SEQ ID NO:38 is the secretory signal sequence.

Then, novelty of the amino acid sequences of VH and VL of the anti-PERP mouse antibody KM3411 was examined. GCG Package (version 9.1, manufactured by Genetics Computer Group) was used as a sequence analysis system and amino acid sequence database of known proteins were searched by BLASTP method [*Nucleic Acid Res.*, 25, 3389 (1997)]. As a result, no completely identical amino acid sequence was found for both VH and VL and it was confirmed that VH and VL of the anti-PERP mouse antibody KM3411 have novel amino acid sequences.

Furthermore, CDRs of VH and VL of the anti-PERP mouse antibody KM3411 were identified by comparing them with the amino acid sequences of known antibodies. Amino acid sequences of CDR1, CDR2 and CDR3 of VH of the anti-PERP mouse antibody KM3411 were represented by SEQ ID NOs:3, 45 and 5, respectively, and amino acid sequences of CDR1, CDR2 and CDR3 of VL thereof were represented by SEQ ID NOs:11, 12 and 13, respectively.

(2) Stable Expression Using Animal Cells of Anti-PERP Chimeric Antibody (2)-1 Construction of Anti-PERP Chimeric Antibody-Expressing Vector pKANTEX3411

Anti-PERP chimeric antibody-expressing vector pKANTEX3411 was constructed as follows using the vector for humanized antibody expression, pKANTEX93, described in WO 97/10354 and plasmids pKM3411H#9 and pKM3411L#4 produced in the above (1)-2.

In order to prepare cDNA encoding VH of the anti-PERP mouse antibody KM3411 by PCR, synthetic DNAs having the nucleotide sequences represented by SEQ ID NOs:46 and 47 were designed and synthesized, and in order to prepare cDNA encoding VL, synthetic DNAs having the nucleotide sequences represented by SEQ ID NOs:48 and 49 were designed and synthesized. Each synthetic DNA (manufactured by Genset) contains a restriction enzyme recognizing sequence at the 5' terminal for cloning to pKANTEX93. The plasmid pKM3411H#9 (20 ng) produced in the above (1)-2 was added to a buffer containing 50 µL of PCR Buffer #1 (manufactured by TOYOBO) attached to KOD DNA Polymerase, 0.2 mmol/L dNTPs, 1 mmol/L magnesium chloride and 0.5 µmol/L of synthetic DNAs having the nucleotide sequence represented by SEQ ID NOs:46 and 47. After heating at 94° C. for 3 minutes using a thermal cycler, 2.5 units of KOD DNA Polymerase (manufactured by TOYOBO) was added thereto and reaction was carried out by 25 cycles, one cycle consisting of reaction at 94° C. for 30 seconds, reaction at 58° C. for 30 seconds and reaction at 74° C. for 1 minute. Similarly, 20 ng of the plasmid pKM3411L#4 produced in (1)-2 of Reference Example 2 was added to a buffer containing 50 µL of PCR Buffer #1 (manufactured by TOYOBO) attached to KOD DNA Polymerase, 0.2 mmol/L dNTPs, 1 mmol/L magnesium chloride and 0.5 µmol/L of synthetic DNAs having the nucleotide sequence represented by SEQ ID NOs:48 and 49 and then PCR was carried out according to the above-described method. The reaction solution (40 µL) was subjected to agarose gel electrophoresis and subjected to QIAquick Gel Extraction Kit (manufactured by Qiagen) to recover a PCR product of VH of about 0.47 kb and a PCR product of VL in about 0.45 kb.

Figure 8:
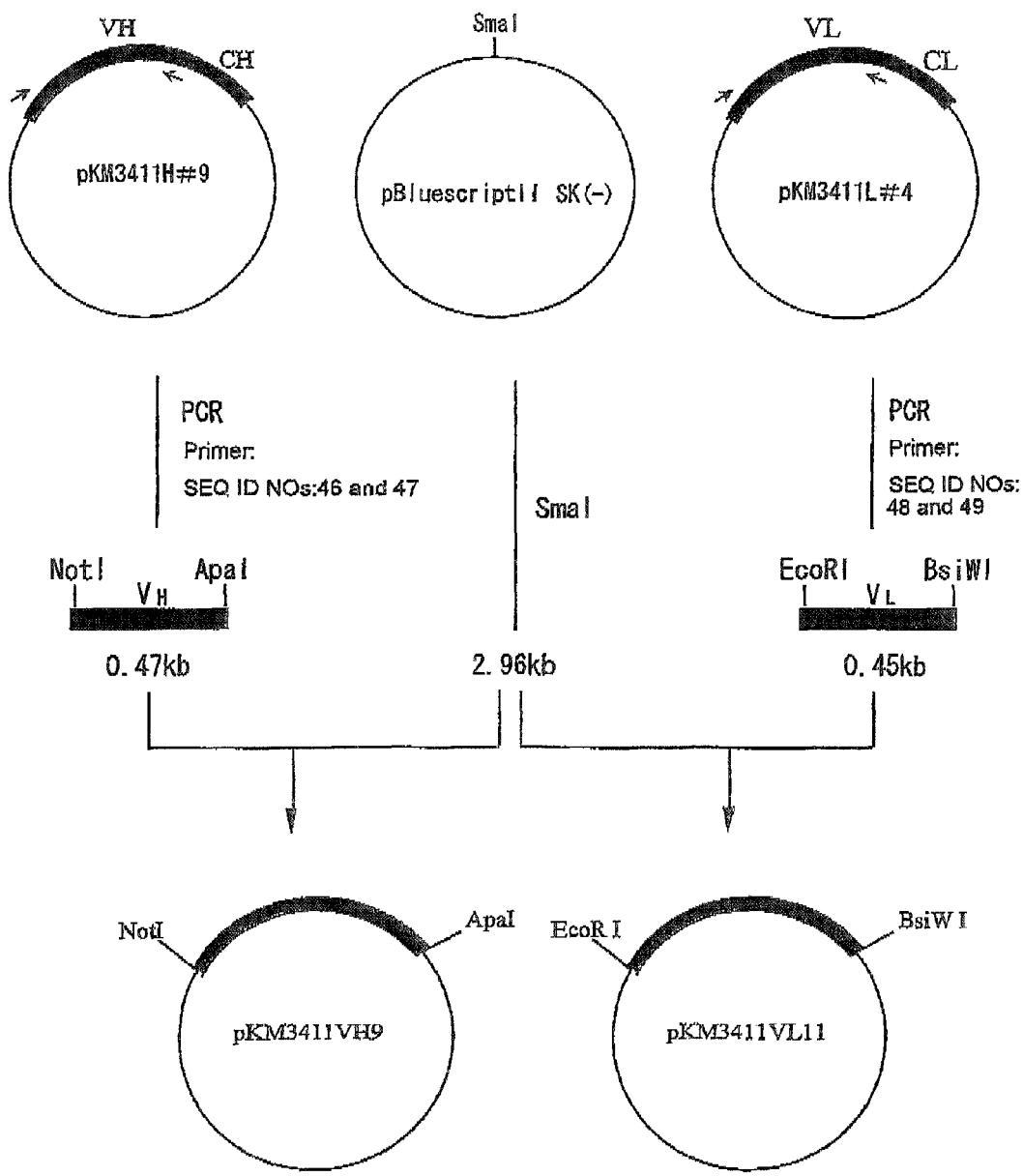
FIG. 8 shows a step for construction of plasmids pKM3411VH9 and pKM3411VL11.

Then, 0.05 pmol of DNA obtained by digesting a plasmid pBluescript II SK(-) (manufactured by Stratagene) with a restriction enzyme SmaI (manufactured by Takara Shuzo) and 0.5 pmol of each of the above-produced each PCR product were added to sterile water to give a volume of 10 µL, and 10 µL of solution I of Takara ligation kit ver.2 (manufactured by Takara Shuzo) and 0.5 µL of a restriction enzyme SmaI (manufactured by Takara Shuzo) were further added thereto, followed by reaction at 22° C. overnight. *Escherichia coli* DH5α (manufactured by TOYOBO) was transformed using the above-produced recombinant DNA solution. From the clone of the resulting transformant, each plasmid DNA was produced, followed by reaction using a Big Dye Terminator Cycle Sequencing FS Ready Reaction Kit (manufactured by PE Biosystems) according to the manufacture's instructions attached thereto, the nucleotide sequence was analyzed using DNA Sequencer ABI PRISM 3700 of the same company and it was confirmed that the plasmids pKM3411VH9 and pKM3411VL11 shown in FIG. 8 having desired nucleotide sequences were produced.

Then, each of vector for humanized antibody expression, pKANTEX93, and the above-produced pKM3411VL11 was digested with a restriction enzyme BsiWI (manufactured by New England BioLab) and then digested with a restriction enzyme EcoRI (manufactured by Takara Shuzo). The reaction solution after the digestion was subjected to agarose gel electrophoresis and each of EcoRI-BsiWI fragment of VL of about 0.45 kb and EcoRI-BsiWI fragment of pKANTEX93 of about 12.7 kb was recovered using QIAquick Gel Extraction Kit (manufactured by Qiagen).

Figure 9:
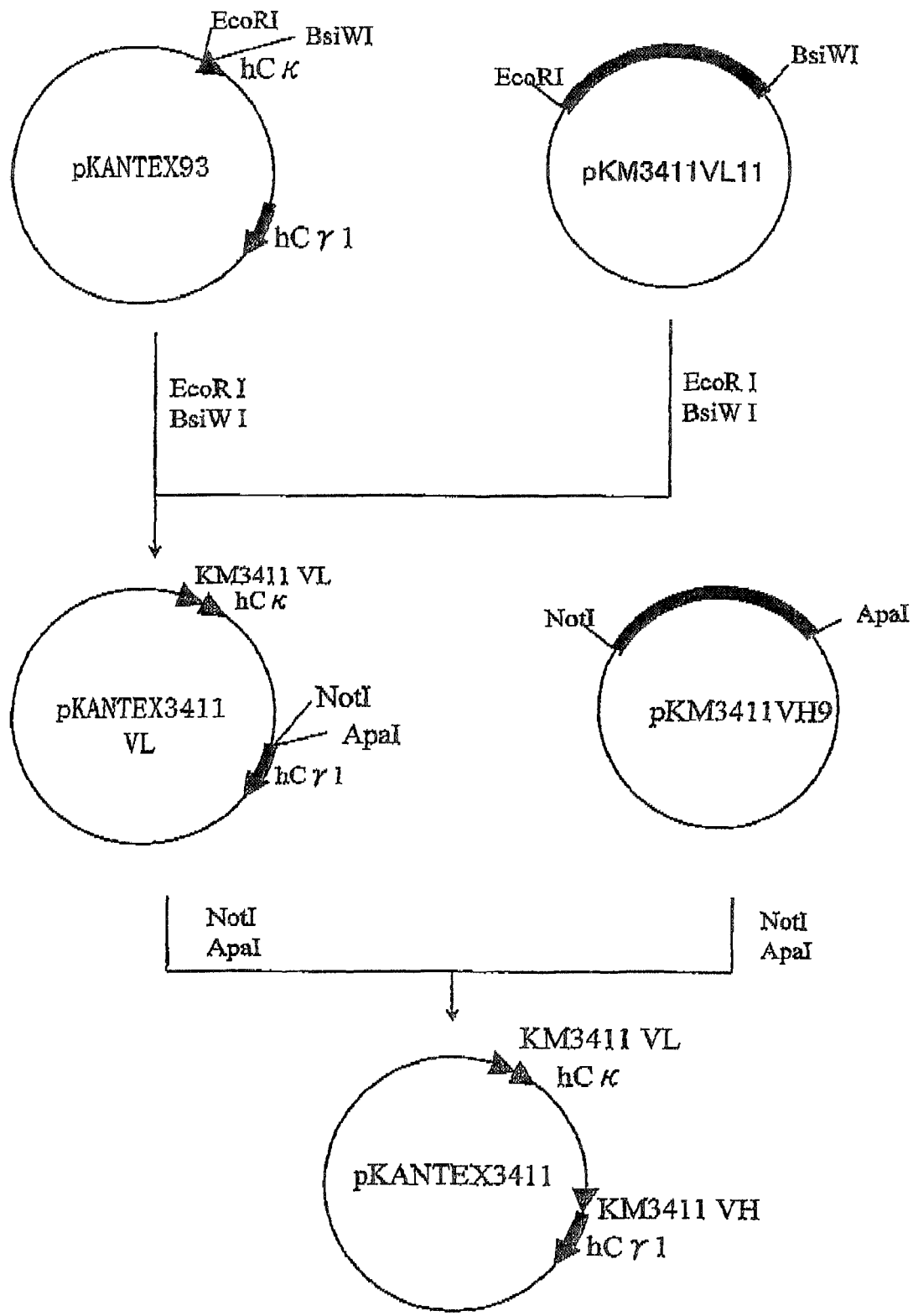
FIG. 9 shows a step for construction of a plasmid pKANTEX3411.

The resulting 2 different fragments were ligated using Ligation High (manufactured by TOYOBO) according to the manufacture's instructions attached thereto and the resulting recombinant plasmid DNA solution was used for the transformation of the *Escherichia coli* DH5α (manufactured by TOYOBO). From a clone of the resulting transformant, each plasmid DNA was produced and treated with restriction enzyme to confirm that a plasmid pKANTEX3411 VL as shown in FIG. 9 into which the desired EcoRI-BsiWI fragment of about 0.45 kb was inserted was obtained.

Then, each of the above-produced pKANTEX3411VL and pKM3411VH9 was digested with a restriction enzyme ApaI (manufactured by Takara Shuzo) and then with a restriction enzyme NotI (manufactured by Takara Shuzo). The reaction solution after the digestion was subjected to agarose gel electrophoresis and each of ApaI-NotI fragment derived from pKANTEX3411VL of about 13.2 kb and ApaI-NotI fragment derived from pKM3411VH of about 0.47 kb was recovered. The resulting 2 kinds of fragments were ligated using Ligation High (manufactured by TOYOBO) according to the manufacture's instructions attached thereto and, using the resulting recombinant plasmid DNA solution, *Escherichia coli* DH5α (manufactured by TOYOBO) was transformed. Each plasmid DNA was produced from the resulting clone of the transformant and treated with to confirm that restriction enzyme that a plasmid pKANTEX3411 as shown in FIG. 9 into which the desired ApaI-NotI fragment of about 0.47 kb was inserted was produced. With regard to the plasmid, after the reaction was carried out using BigDye Terminator Cycle Sequencing FS Ready Reaction Kit (manufactured by PE Biosystems) according to the manufacture's instructions attached thereto and the nucleotide sequence was analyzed by DNA Sequencer ABI PRISM 3700 of the same company and, as a result, it was confirmed that the desired plasmid in which each of cDNA encoding VH of the KM3411 and cDNAs encoding VL was cloned was produced.

(2)-2 Expression in Animal Cells of Anti-PERP Chimeric Antibody

Expression of the anti-PERP chimeric antibody in animal cells was carried out using the anti-PERP chimeric antibody expressing vector pKANTEX3411 produced in the above (2)-1 of by a usual method [*Antibody Engineering, A Practical Guide*, W. H. Freeman and Company (1992)] and a transformant KM3481 into which pKANTEX3411 was introduced was produced.

(3) Production of Purified Antibody

After the transformant produced in the above (2)-2 was cultured by a usual culturing method, the cell suspension was recovered and centrifuged at 3,000 rpm and at 4° C. for 5 minutes and the recovered culture supernatant was sterilized by filtering through a Millex GV Filter (manufactured by Millipore) having a pore size of 0.22 μm. From the resulting culture supernatant, an anti-PERP chimeric antibody KM3481 was purified using a Mab Select (manufactured by Amersham Bioscience) column according to the manufacture's instructions attached thereto.

Degree of purification and expressed molecular size of the resulting anti-PERP chimeric antibody KM3481 were confirmed by SDS-PAGE using a gradient gel (manufactured by Atto; catalog no. E-T520L) according to the manufacture's instructions attached thereto. Anti-PERP mouse antibody KM3411 was electrophoresed as a control at the same time.

Figure 10:
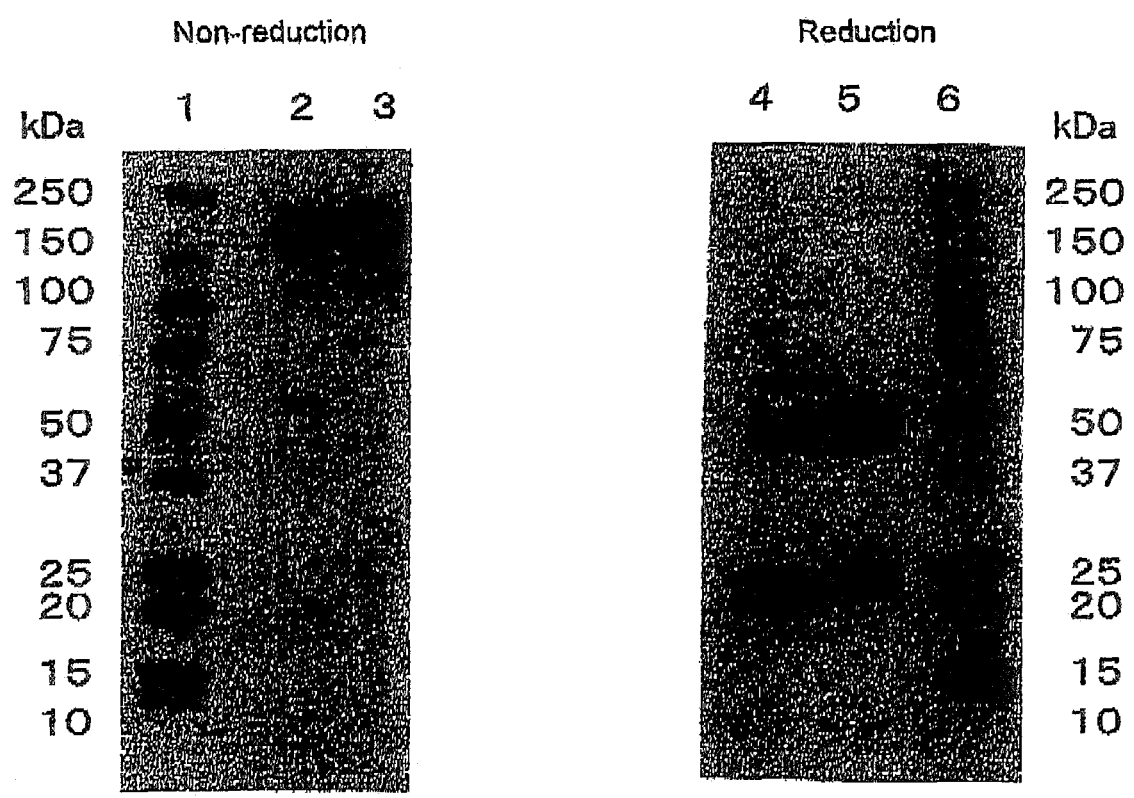
FIG. 10 shows electrophoretic patterns of the purified anti-PERP chimeric antibody by SDS-PAGE (using 5 to 20% gradient gel). Left and right sides are results of electrophoresis carried out under non-reducing condition and reducing conditions, respectively. Lanes 1 and 6, lanes 2 and 4 and lanes 3 and 5 show electrophoretic patterns of a molecular weight marker, anti-PERP mouse antibody KM3411 and anti-PERP chimeric antibody KM3481, respectively.

The result is shown in FIG. 10. In the purified anti-PERP chimeric antibody KM3481, one band for molecular weight of about 150 kilodaltons (hereinafter referred to as "Kd") was found under non-reducing conditions, and two bands of about 50 Kd and about 25 Kd were found under reducing conditions. Those molecular weights coincide with the report [*Antibodies—A Laboratory Manual*, Cold Spring Harbor Laboratory, Chapter 14 (1988), *Monoclonal Antibodies—Principles and practice*, Academic Press Limited (1996)] that under non-reducing conditions, antibodies of the IgG class have a molecular weight of about 150 Kd and under reducing conditions, and S—S bond in the molecule is cleaved to decompose into an H chain having a molecular weight of about 50 Kd and an L chain having a molecular weight of about 25 Kd. Thus, it was confirmed that the anti-PERP chimeric antibody KM3481 was expressed as an antibody molecule having a correct structure.

While the invention has been described in detail and with reference to specific embodiments thereof, it will be apparent to one skill in the art that various changes and modifications can be made therein without departing from the spirit and scope thereof.

This application is based on Japanese patent application No. 2005-352297 filed Dec. 6, 2005, the entire contents of which are incorporated hereinto by reference. All references cited herein are incorporated in their entirety.

The invention claimed is:

1. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof specifically binds to an epitope comprising Asp(40), Glu(62) and Glu(63) of SEQ ID NO:2, and wherein said antibody or antigen-binding fragment thereof has no consensus sequence of an N-linked sugar chain in a variable region.

2. The antibody or antigen-binding fragment thereof according to claim 1, wherein said antibody or antigen-binding fragment thereof has no consensus sequence of an N-linked sugar chain in all CDRs in the VH and VL regions.

3. The antibody or antigen-binding fragment thereof according to claim 1, wherein the antibody is selected from the group consisting of a human chimeric antibody, a humanized antibody and a human antibody.

4. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof specifically binds to an extracellular region of human PERP protein in its naturally-existing conformation, wherein said PERP protein consists of the amino acid sequence of SEQ ID NO: 2, wherein said antibody or antigen-binding fragment thereof has no consensus sequence of an N-linked sugar chain in a variable region, and wherein the VH region comprises the amino acid sequence of any one of SEQ ID NOs: 14 to 19.

5. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof specifically binds to an extracellular region of human PERP protein in its naturally-existing conformation, wherein said PERP protein consists of the amino acid sequence of SEQ ID NO: 2, wherein said antibody or antigen-binding fragment thereof has no consensus sequence of an N-linked sugar chain in a variable region, and wherein the VL region comprises the amino acid sequence of SEQ ID NO: 20.

6. The antibody or antigen-binding fragment thereof according to claim 4, wherein the VL region comprises the amino acid sequence of SEQ ID NO: 20.

7. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof specifically binds to an extracellular region of human PERP protein in its naturally-existing conformation, wherein said PERP protein consists of the amino acid sequence of SEQ ID NO: 2, wherein said antibody or antigen-binding fragment thereof has no consensus sequence of an N-linked sugar chain in a variable region,
and wherein the VH region comprises the amino acid sequence of any one of SEQ ID NOs: 30 to 35, or an amino acid sequence in which at least one substitution is introduced into the amino acid sequence of any one of SEQ ID NOs: 30 to 35, wherein said substitution is selected from the group consisting of: substitution of Gly at position 27 with Phe; substitution of Ser at position 30 with Thr; substitution of Pro at position 41 with Phe; substitution of Lys at position 44 with Asn; substitution of Gly at position 45 with Arg; substitution of Ile at position 49 with Met; substitution of Val at position 72 with Arg and; substitution of Ala at position 97 with Thr.

8. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof specifically binds to an extracellular region of human PERP protein in its naturally-existing conformation, wherein said PERP protein consists of the amino acid sequence of SEQ ID NO: 2, wherein said antibody or antigen-binding fragment thereof has no consensus sequence of an N-linked sugar chain in a variable region,
and wherein the VL region comprises the amino acid sequence of SEQ ID NO: 36, or an amino acid sequence in which at least one substitution is introduced into the amino acid sequence of SEQ ID NO: 36, said substitution selected from the group consisting of: substitution of Gln at position 3 with Val; substitution of Thr at position 5 with Ile; substitution of Tyr at position 35 with Phe; substitution of Ala at position 42 with Ser; substitution of Leu at position 46 with Trp; substitution of Asp at position 69 with Ser; substitution of Phe at position 70 with Tyr; substitution of Thr at position 71 with Ser and; substitution of Leu at position 77 with Met.

9. The antibody or antigen-binding fragment according to claims 7,
wherein the VL region comprises the amino acid sequence of SEQ ID NO: 36, or an amino acid sequence in which at least one substitution is introduced into the amino acid sequence of SEQ ID NO: 36, said substitution selected from the group consisting of: substitution of Gln at position 3 with Val; substitution of Thr at position 5 with Ile; substitution of Tyr at position 35 with Phe; substitution of Ala at position 42 with Ser; substitution of Leu at position 46 with Trp; substitution of Asp at position 69 with Ser; substitution of Phe at position 70 with Tyr; substitution of Thr at position 71 with Ser and; substitution of Leu at position 77 with Met.

10. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof specifically binds to an extracellular region of human PERP protein in its naturally-existing conformation, wherein said PERP protein consists of the amino acid sequence of SEQ ID NO: 2, wherein said antibody or antigen-binding fragment thereof has no consensus sequence of an N-linked sugar chain in a variable region, and wherein the VH region comprises the amino acid sequence of any one of SEQ ID NOs: 51 to 56.

11. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof specifically binds to an extracellular region of human PERP protein in its naturally-existing conformation, wherein said PERP protein consists of the amino acid sequence of SEQ ID NO: 2, wherein said antibody or antigen-binding fragment thereof has no consensus sequence of an N-linked sugar chain in a variable region, and wherein the VL region comprises the amino acid sequence of any one of SEQ ID NOs: 58 to 63.

12. The antibody or antigen-binding fragment thereof according to claim 10, wherein the VL region comprises the amino acid sequence of any one of SEQ ID NOs: 58 to 63.

13. An isolated antibody, or antigen-binding fragment thereof, comprising a heavy chain variable (VH) region with 3 complementarity determining regions (CDRs), and a light chain variable (VL) region with 3 CDRs, wherein said antibody or antigen-binding fragment thereof has no consensus sequence of an N-linked sugar chain in a variable region, and wherein said antibody or antigen-binding fragment thereof binds to an epitope recognized by a monoclonal antibody produced by hybridoma KM3411 (FERM BP-8643).

14. The antigen-binding fragment according to claim 1, wherein said antigen-binding fragment is selected from the group consisting of: Fab; Fab'; F(ab')$_2$; a single chain antibody (scFv); a dimerized V region (diabody); a disulfide stabilized V region (dsFv) and; a CDR-containing peptide.

15. The antibody or antigen-binding fragment thereof according to claim 13, wherein the antibody or antigen-binding fragment is monoclonal.

16. A process for producing the antibody or antigen-binding fragment thereof of claim 1, comprising culturing a transformant in a medium to form and accumulate the antibody or antigen-binding fragment thereof in the culture, and recovering the antibody or the antigen-binding fragment thereof from the culture, said transformant being obtainable by introducing into a host cell a recombinant vector comprising a DNA encoding the antibody or antigen-binding fragment thereof of claim 1.

\* \* \* \* \*

SEQUENCE LISTING

<160> NUMBER OF SEQ ID NOS: 117

<210> SEQ ID NO 1
<211> LENGTH: 1941
<212> TYPE: DNA
<213> ORGANISM: Homo sapience

<400> SEQUENCE: 1

```
gcttttgtgg cggcgcccgc gctcgcaggc cactctctgc tgtcgcccgt cccgcgcgct      60
cctccgaccc gctccgctcc gctccgctcg gccccgcgcc gcccgtcaac atgatccgct     120
gcggcctggc ctgcgagcgc tgccgctgga tcctgccccct gctcctactc agcgccatcg     180
ccttcgacat catcgcgctg gccggccgcg gctggttgca gtctagcgac cacggccaga     240
cgtcctcgct gtggtggaaa tgctcccaag agggcggcgg cagcgggtcc tacgaggagg     300
gctgtcagag cctcatggag tacgcgtggg gtagagcagc ggctgccatg ctcttctgtg     360
gcttcatcat cctggtgatc tgtttcatcc tctccttctt cgccctctgt ggacccccaga     420 tgcttgtctt cctgagagtg attggaggtc tccttgcctt ggctgctgtg ttccagatca     480
tctccctggt aatttacccc gtgaagtaca cccagacctt caccttcat gccaaccctg     540
```

```
ctgtcactta catctataac tgggcctacg gctttgggtg ggcagccacg attatcctga    600
ttggctgtgc cttcttcttc tgctgcctcc ccaactacga agatgacctt ctgggcaatg    660
ccaagcccag gtacttctac acatctgcct aacttgggaa tgaatgtggg agaaaatcgc    720
tgctgctgag atggactcca gaagaagaaa ctgtttctcc aggcgacttt gaacccattt    780
tttggcagtg ttcatattat taaactagtc aaaaatgcta aaataatttg ggagaaaata    840
ttttttaagt agtgttatag tttcatgttt atctttattt atgttttgtg aagttgtgtc    900
ttttcactaa ttacctatac tatgccaata tttcctatct atccataaca tttatactac    960
atttgtaaga gaatatgcac gtgaaactta acactttata aggtaaaaat gaggtttcca   1020
agatttaata atctgatcaa gttcttgtta tttccaaata gaatggactc ggtctgttaa   1080
gggctaagga gaagaggaag ataaggttaa aagttgttaa tgaccaaaca ttctaaaaga   1140
aatgcaaaaa aaaagtttat tttcaagcct tcgaactatt taaggaaagc aaaatcattt   1200
cctaaatgca tatcatttgt gagaatttct cattaatatc ctgaatcatt cattttagct   1260
aaggcttcat gttgactcga tatgtcatct aggaaagtac tatttcatgg tccaaacctg   1320
ttgccatagt tggtaaggct ttcctttaag tgtgaaatat ttagatgaaa ttttctcttt   1380
taaagttctt tatagggtta gggtgtggga aaatgctata ttaataaatc tgtagtgttt   1440 tgtgttata tgttcagaac cagagtagac tggattgaaa gatggactgg gtctaattta   1500
tcatgactga tagatctgtt aagttgtgta gtaaagcatt aggagggtca ttcttgtcac   1560
aaaagtgcca ctaaacagc ctcaggagaa taaatgactt gcttttctaa atctcaggtt   1620
tatctgggct ctatcatata gacaggcttc tgatagtttg caactgtaag cagaaaccta   1680
catatagtta aaatcctggt ctttcttggt aaacagattt taaatgtctg atataaaaca   1740
tgccacagga gaattcgggg atttgagttt ctctgaatag catatatatg atgcatcgga   1800
taggtcatta tgattttta ccatttcgac ttacataatg aaaaccaatt cattttaaat   1860
atcagattat tattttgtaa gttgtggaaa aagctaattg tagttttcat tatgaagttt   1920
tcccaataaa ccaggtattc t                                             1941
```

<210> SEQ ID NO 2
<211> LENGTH: 193
<212> TYPE: PRT
<213> ORGANISM: Homo sapience

<400> SEQUENCE: 2

```
Met Ile Arg Cys Gly Leu Ala Cys Glu Arg Cys Arg Trp Ile Leu Pro
  1               5                  10                  15

Leu Leu Leu Leu Ser Ala Ile Ala Phe Asp Ile Ile Ala Leu Ala Gly
             20                  25                  30

Arg Gly Trp Leu Gln Ser Ser Asp His Gly Gln Thr Ser Ser Leu Trp
         35                  40                  45

Trp Lys Cys Ser Gln Glu Gly Gly Ser Gly Ser Tyr Glu Glu Gly
     50                  55                  60

Cys Gln Ser Leu Met Glu Tyr Ala Trp Gly Arg Ala Ala Ala Ala Met
 65                  70                  75                  80

Leu Phe Cys Gly Phe Ile Ile Leu Val Ile Cys Phe Ile Leu Ser Phe
                 85                  90                  95

Phe Ala Leu Cys Gly Pro Gln Met Leu Val Phe Leu Arg Val Ile Gly
            100                 105                 110

Gly Leu Leu Ala Leu Ala Ala Val Phe Gln Ile Ile Ser Leu Val Ile
        115                 120                 125
```

```
Tyr Pro Val Lys Tyr Thr Gln Thr Phe Thr Leu His Ala Asn Pro Ala
            130                 135                 140

Val Thr Tyr Ile Tyr Asn Trp Ala Tyr Gly Phe Gly Trp Ala Ala Thr
145                 150                 155                 160

Ile Ile Leu Ile Gly Cys Ala Phe Phe Cys Cys Leu Pro Asn Tyr
                165                 170                 175

Glu Asp Asp Leu Leu Gly Asn Ala Lys Pro Arg Tyr Phe Tyr Thr Ser
            180                 185                 190

Ala

<210> SEQ ID NO 3
<211> LENGTH: 6
<212> TYPE: PRT
<213> ORGANISM: Mus musculus

<400> SEQUENCE: 3

Thr Glu Tyr Ala Trp Asn
 1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ile Gly Tyr Thr Gly Arg Thr Asn Tyr Ala Pro Ser Leu Lys Ser
 1               5                  10                  15

<210> SEQ ID NO 5
<211> LENGTH: 3
<212> TYPE: PRT
<213> ORGANISM: Mus musculus

<400> SEQUENCE: 5

Met Asp Tyr
 1

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ile Gly Tyr Thr Gly Arg Thr Tyr Ser Pro Ser Leu Lys Ser
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ile Gly Tyr Thr Gly Arg Thr Ser Tyr Ser Pro Ser Leu Lys Ser
 1               5                  10                  15

<210> SEQ ID NO 8
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ile Gly Tyr Thr Gly Arg Thr Gly Tyr Ser Pro Ser Leu Lys Ser
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Ile Gly Tyr Thr Gly Arg Thr Ser Tyr Ala Pro Ser Leu Lys Ser
 1               5                  10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ile Gly Tyr Thr Gly Arg Thr Gly Tyr Ala Pro Ser Leu Lys Ser
 1               5                  10                  15

<210> SEQ ID NO 11
<211> LENGTH: 10
<212> TYPE: PRT
<213> ORGANISM: Mus musculus

<400> SEQUENCE: 11

Ser Ala Ser Ser Ser Val Ser Tyr Met His
 1               5                  10

<210> SEQ ID NO 12
<211> LENGTH: 7
<212> TYPE: PRT
<213> ORGANISM: Mus musculus

<400> SEQUENCE: 12

Ser Thr Ser Asn Leu Ala Ser
 1               5

<210> SEQ ID NO 13
<211> LENGTH: 9
<212> TYPE: PRT
<213> ORGANISM: Mus musculus

<400> SEQUENCE: 13

Gln Gln Arg Ser Ser Tyr Pro Pro Thr
 1               5

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
```

```
                                         -continued
     peptide

<400> SEQUENCE: 14

Asp Val Gln Leu Gln Glu Ser Gly Pro Gly Leu Val Lys Pro Ser Gln
 1               5                  10                  15

Ser Leu Ser Leu Thr Cys Thr Val Thr Gly Phe Ser Ile Thr Thr Glu
             20                  25                  30

Tyr Ala Trp Asn Trp Ile Arg Gln Phe Pro Gly Asn Arg Leu Glu Trp
         35                  40                  45

Met Gly Tyr Ile Gly Tyr Thr Gly Arg Thr Asn Tyr Ala Pro Ser Leu
     50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Thr Arg Met Asp Tyr Trp Gly Gln Gly Thr Ser Val Thr Val Ser Ser
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Val Gln Leu Gln Glu Ser Gly Pro Gly Leu Val Lys Pro Ser Gln
 1               5                  10                  15

Ser Leu Ser Leu Thr Cys Thr Val Thr Gly Phe Ser Ile Thr Thr Glu
             20                  25                  30

Tyr Ala Trp Asn Trp Ile Arg Gln Phe Pro Gly Asn Arg Leu Glu Trp
         35                  40                  45

Met Gly Tyr Ile Gly Tyr Thr Gly Arg Thr Tyr Tyr Ser Pro Ser Leu
     50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Thr Arg Met Asp Tyr Trp Gly Gln Gly Thr Ser Val Thr Val Ser Ser
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Val Gln Leu Gln Glu Ser Gly Pro Gly Leu Val Lys Pro Ser Gln
 1               5                  10                  15

Ser Leu Ser Leu Thr Cys Thr Val Thr Gly Phe Ser Ile Thr Thr Glu
             20                  25                  30

Tyr Ala Trp Asn Trp Ile Arg Gln Phe Pro Gly Asn Arg Leu Glu Trp
         35                  40                  45

Met Gly Tyr Ile Gly Tyr Thr Gly Arg Thr Ser Tyr Ser Pro Ser Leu
     50                  55                  60
```

```
Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Thr Arg Met Asp Tyr Trp Gly Gln Gly Thr Ser Val Thr Val Ser Ser
            100                 105                 110
```

<210> SEQ ID NO 17
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Phe Ser Ile Thr Thr Glu
                 20                  25                  30

Tyr Ala Trp Asn Trp Ile Arg Gln Phe Pro Gly Asn Arg Leu Glu Trp
             35                  40                  45

Met Gly Tyr Ile Gly Tyr Thr Gly Arg Thr Gly Tyr Ser Pro Ser Leu
         50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Thr Arg Met Asp Tyr Trp Gly Gln Gly Thr Ser Val Thr Val Ser Ser
            100                 105                 110
```

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Phe Ser Ile Thr Thr Glu
                 20                  25                  30

Tyr Ala Trp Asn Trp Ile Arg Gln Phe Pro Gly Asn Arg Leu Glu Trp
             35                  40                  45

Met Gly Tyr Ile Gly Tyr Thr Gly Arg Thr Ser Tyr Ala Pro Ser Leu
         50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Thr Arg Met Asp Tyr Trp Gly Gln Gly Thr Ser Val Thr Val Ser Ser
            100                 105                 110
```

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Asp Val Gln Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Thr Glu
            20                  25                  30

Tyr Ala Trp Asn Trp Ile Arg Gln Phe Pro Gly Asn Arg Leu Glu Trp
        35                  40                  45

Met Gly Tyr Ile Gly Tyr Thr Gly Arg Thr Gly Tyr Ala Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
            85                  90                  95

Thr Arg Met Asp Tyr Trp Gly Gln Gly Thr Ser Val Thr Val Ser Ser
        100                 105                 110

<210> SEQ ID NO 20
<211> LENGTH: 106
<212> TYPE: PRT
<213> ORGANISM: Mus musculus

<400> SEQUENCE: 20

Gln Ile Val Leu Ile Gln Ser Pro Val Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
            85                  90                  95

Phe Gly Ala Gly Thr Lys Leu Glu Leu Lys
        100                 105

<210> SEQ ID NO 21
<211> LENGTH: 112
<212> TYPE: PRT
<213> ORGANISM: Mus musculus

<400> SEQUENCE: 21

Asp Val Gln Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Thr Glu
            20                  25                  30

Tyr Ala Trp Asn Trp Ile Arg Gln Phe Pro Gly Asn Arg Leu Glu Trp
        35                  40                  45

Met Gly Tyr Ile Gly Tyr Thr Gly Arg Thr Asn Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
            85                  90                  95

```
Thr Arg Met Asp Tyr Trp Gly Gln Gly Thr Ser Val Thr Val Ser Ser
            100                 105                 110
```

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
gtgtctcgag tgatagagat tcgactttig agagatgggg cgtagttagt tc      52

<210> SEQ ID NO 23
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
gtgtctcgag tgatagagat tcgactttig agagatgggc tgtagtaagt tc      52

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gtgtctcgag tgatagagat tcgactttig agagatgggc tgtaggaagt tc      52

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
gtgtctcgag tgatagagat tcgactttig agagatgggc tgtagccagt tc      52

<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
gtgtctcgag tgatagagat tcgactttig agagatgggg cgtaggaagt tc      52

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
gtgtctcgag tgatagagat tcgactttig agagatgggg cgtagccagt tc      52

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
aaggaaaaaa gcggccgcac atcgctctca ctggaggctg                40

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Thr Glu
            20                  25                  30

Tyr Ala Trp Asn Trp Ile Arg Gln Pro Pro Gly Lys Gly Leu Glu Trp
        35                  40                  45

Ile Gly Tyr Ile Gly Tyr Thr Gly Arg Thr Asn Tyr Ser Pro Ser Leu
    50                  55                  60

Lys Ser Arg Ile Thr Ile Ser Val Asp Thr Ser Lys Asn Gln Phe Ser
65                  70                  75                  80

Leu Gln Leu Ser Ser Val Thr Ala Glu Asp Thr Ala Thr Tyr Tyr Cys
                85                  90                  95

Ala Arg Met Asp Tyr Trp Gly Gln Gly Thr Leu Val Thr Val Ser Ser
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Thr Glu
            20                  25                  30

Tyr Ala Trp Asn Trp Ile Arg Gln Pro Pro Gly Lys Gly Leu Glu Trp
        35                  40                  45

Ile Gly Tyr Ile Gly Tyr Thr Gly Arg Thr Asn Tyr Ala Pro Ser Leu
    50                  55                  60

Lys Ser Arg Ile Thr Ile Ser Val Asp Thr Ser Lys Asn Gln Phe Ser
65                  70                  75                  80

Leu Gln Leu Ser Ser Val Thr Ala Glu Asp Thr Ala Thr Tyr Tyr Cys
                85                  90                  95

Ala Arg Met Asp Tyr Trp Gly Gln Gly Thr Leu Val Thr Val Ser Ser
            100                 105                 110

<210> SEQ ID NO 31

<211> LENGTH: 112
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Glu
            20                  25                  30

Tyr Ala Trp Asn Trp Ile Arg Gln Pro Pro Gly Lys Gly Leu Glu Trp
        35                  40                  45

Ile Gly Tyr Ile Gly Tyr Thr Gly Arg Thr Tyr Tyr Ser Pro Ser Leu
    50                  55                  60

Lys Ser Arg Ile Thr Ile Ser Val Asp Thr Ser Lys Asn Gln Phe Ser
65                  70                  75                  80

Leu Gln Leu Ser Ser Val Thr Ala Glu Asp Thr Ala Thr Tyr Tyr Cys
                85                  90                  95

Ala Arg Met Asp Tyr Trp Gly Gln Gly Thr Leu Val Thr Val Ser Ser
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Glu
            20                  25                  30

Tyr Ala Trp Asn Trp Ile Arg Gln Pro Pro Gly Lys Gly Leu Glu Trp
        35                  40                  45

Ile Gly Tyr Ile Gly Tyr Thr Gly Arg Thr Ser Tyr Ser Pro Ser Leu
    50                  55                  60

Lys Ser Arg Ile Thr Ile Ser Val Asp Thr Ser Lys Asn Gln Phe Ser
65                  70                  75                  80

Leu Gln Leu Ser Ser Val Thr Ala Glu Asp Thr Ala Thr Tyr Tyr Cys
                85                  90                  95

Ala Arg Met Asp Tyr Trp Gly Gln Gly Thr Leu Val Thr Val Ser Ser
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Glu
            20                  25                  30

Tyr Ala Trp Asn Trp Ile Arg Gln Pro Pro Gly Lys Gly Leu Glu Trp

```
                    35                  40                  45
Ile Gly Tyr Ile Gly Tyr Thr Gly Arg Thr Gly Tyr Ser Pro Ser Leu
         50                  55                  60

Lys Ser Arg Ile Thr Ile Ser Val Asp Thr Ser Lys Asn Gln Phe Ser
 65                  70                  75                  80

Leu Gln Leu Ser Ser Val Thr Ala Glu Asp Thr Ala Thr Tyr Tyr Cys
                 85                  90                  95

Ala Arg Met Asp Tyr Trp Gly Gln Gly Thr Leu Val Thr Val Ser Ser
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Thr Glu
                 20                  25                  30

Tyr Ala Trp Asn Trp Ile Arg Gln Pro Pro Gly Lys Gly Leu Glu Trp
             35                  40                  45

Ile Gly Tyr Ile Gly Tyr Thr Gly Arg Thr Ser Tyr Ala Pro Ser Leu
         50                  55                  60

Lys Ser Arg Ile Thr Ile Ser Val Asp Thr Ser Lys Asn Gln Phe Ser
 65                  70                  75                  80

Leu Gln Leu Ser Ser Val Thr Ala Glu Asp Thr Ala Thr Tyr Tyr Cys
                 85                  90                  95

Ala Arg Met Asp Tyr Trp Gly Gln Gly Thr Leu Val Thr Val Ser Ser
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Thr Glu
                 20                  25                  30

Tyr Ala Trp Asn Trp Ile Arg Gln Pro Pro Gly Lys Gly Leu Glu Trp
             35                  40                  45

Ile Gly Tyr Ile Gly Tyr Thr Gly Arg Thr Gly Tyr Ala Pro Ser Leu
         50                  55                  60

Lys Ser Arg Ile Thr Ile Ser Val Asp Thr Ser Lys Asn Gln Phe Ser
 65                  70                  75                  80

Leu Gln Leu Ser Ser Val Thr Ala Glu Asp Thr Ala Thr Tyr Tyr Cys
                 85                  90                  95

Ala Arg Met Asp Tyr Trp Gly Gln Gly Thr Leu Val Thr Val Ser Ser
            100                 105                 110

<210> SEQ ID NO 36
```

```
<211> LENGTH: 106
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Ser Ser Tyr Pro Pro Thr
                85                  90                  95

Phe Gly Gln Gly Thr Lys Val Glu Ile Lys
            100                 105

<210> SEQ ID NO 37
<211> LENGTH: 130
<212> TYPE: PRT
<213> ORGANISM: Mus musculus

<400> SEQUENCE: 37

Met Arg Val Leu Ile Leu Leu Trp Leu Phe Thr Ala Phe Pro Gly Ile
 1               5                  10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Phe Ser Ile Thr
        35                  40                  45

Thr Glu Tyr Ala Trp Asn Trp Ile Arg Gln Phe Pro Gly Asn Arg Leu
    50                  55                  60

Glu Trp Met Gly Tyr Ile Gly Tyr Thr Gly Arg Thr Asn Tyr Ser Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Thr Arg Met Asp Tyr Trp Gly Gln Gly Thr Ser Val Thr Val
        115                 120                 125

Ser Ser
    130

<210> SEQ ID NO 38
<211> LENGTH: 128
<212> TYPE: PRT
<213> ORGANISM: Mus musculus

<400> SEQUENCE: 38

Met His Phe Gln Val Gln Ile Phe Ser Phe Leu Leu Ile Ser Ala Ser
 1               5                  10                  15

Val Ile Met Ser Arg Gly Gln Ile Val Leu Ile Gln Ser Pro Val Ile
            20                  25                  30

Met Ser Ala Ser Pro Gly Glu Lys Val Thr Ile Thr Cys Ser Ala Ser
```

```
                35                  40                  45
Ser Ser Val Ser Tyr Met His Trp Phe Gln Gln Lys Pro Gly Thr Ser
        50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Pro Thr Phe Gly Ala Gly Thr Lys Leu Glu Leu Lys
            115                 120                 125

<210> SEQ ID NO 39
<211> LENGTH: 33
<212> TYPE: DNA
<213> ORGANISM: artificial sequence
<220> FEATURE:
<223> OTHER INFORMATION: Description of Artificial Sequence: Synthetic
      DNA

<400> SEQUENCE: 39
ccggaattcg ccaccatgat ccgctgcggc ctg                             33

<210> SEQ ID NO 40
<211> LENGTH: 28
<212> TYPE: DNA
<213> ORGANISM: artificial sequence
<220> FEATURE:
<223> OTHER INFORMATION: Description of Artificial Sequence: Synthetic
      DNA

<400> SEQUENCE: 40
cccaagcttg ggcagatgtg tagaagta                                   28

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
ccagggtcac catggagtta gtttgggcag                                 30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
gaagcacacg actgaggcac ctccagatgt                                 30

<210> SEQ ID NO 43
<211> LENGTH: 390
<212> TYPE: DNA
<213> ORGANISM: Mus musculus
<220> FEATURE:
<221> NAME/KEY: CDS
<222> LOCATION: (1)..(390)

<400> SEQUENCE: 43
```

```
atg aga gtg ctg att ctt ttg tgg ctg ttc aca gcc ttt cct ggt atc        48
Met Arg Val Leu Ile Leu Leu Trp Leu Phe Thr Ala Phe Pro Gly Ile
 1               5                  10                  15 ctg tct gat gtg cag ctt cag gag tcg gga cct ggc ctg gtg aaa cct        96
Leu Ser Asp Val Gln Leu Gln Glu Ser Gly Pro Gly Leu Val Lys Pro
             20                  25                  30 tct cag tct ctg tcc ctc acc tgc act gtc act ggc ttc tca atc acc       144
Ser Gln Ser Leu Ser Leu Thr Cys Thr Val Thr Gly Phe Ser Ile Thr
         35                  40                  45 act gaa tat gcc tgg aac tgg atc cgg cag ttt cca gga aac aga ctg       192
Thr Glu Tyr Ala Trp Asn Trp Ile Arg Gln Phe Pro Gly Asn Arg Leu
     50                  55                  60 gag tgg atg ggc tat ata ggc tac act ggt aga act aac tac agc cca       240
Glu Trp Met Gly Tyr Ile Gly Tyr Thr Gly Arg Thr Asn Tyr Ser Pro
 65                  70                  75                  80 tct ctc aaa agt cga atc tct atc act cga gac act tcc aag aac cag       288
Ser Leu Lys Ser Arg Ile Ser Ile Thr Arg Asp Thr Ser Lys Asn Gln
                 85                  90                  95 ttc ttc ctg cag ttg aat tct gtg act act gag gac aca gcc aca tat       336
Phe Phe Leu Gln Leu Asn Ser Val Thr Thr Glu Asp Thr Ala Thr Tyr
            100                 105                 110 tac tgt aca agg atg gac tac tgg ggt caa gga acc tca gtc acc gtc       384
Tyr Cys Thr Arg Met Asp Tyr Trp Gly Gln Gly Thr Ser Val Thr Val
        115                 120                 125 tcc tca                                                                390
Ser Ser
    130

<210> SEQ ID NO 44
<211> LENGTH: 384
<212> TYPE: DNA
<213> ORGANISM: Mus musculus
<220> FEATURE:
<221> NAME/KEY: CDS
<222> LOCATION: (1)..(384)

<400> SEQUENCE: 44 atg cat ttt caa gtg cag att ttc agc ttc ctg cta atc agt gcc tca        48
Met His Phe Gln Val Gln Ile Phe Ser Phe Leu Leu Ile Ser Ala Ser
 1               5                  10                  15 gtc ata atg tcc aga gga caa att gtt ctc ata cag tct cca gta atc        96
Val Ile Met Ser Arg Gly Gln Ile Val Leu Ile Gln Ser Pro Val Ile
             20                  25                  30 atg tct gca tct cca ggg gag aag gtc act ata acc tgc agt gcc agt       144
Met Ser Ala Ser Pro Gly Glu Lys Val Thr Ile Thr Cys Ser Ala Ser
         35                  40                  45 tca agt gta agt tac atg cac tgg ttc cag cag aag cca ggc act tct       192
Ser Ser Val Ser Tyr Met His Trp Phe Gln Gln Lys Pro Gly Thr Ser
     50                  55                  60 ccc aaa ctc tgg att tat agc aca tcc aac ctg gct tct gga gtc cct       240
Pro Lys Leu Trp Ile Tyr Ser Thr Ser Asn Leu Ala Ser Gly Val Pro
 65                  70                  75                  80 gct cgc ttc agt ggc agt gga tct ggg acc tct tac tca ctc aca att       288
Ala Arg Phe Ser Gly Ser Gly Ser Gly Thr Ser Tyr Ser Leu Thr Ile
                 85                  90                  95 agc cga atg gag gct gaa gat gct gcc act tat tac tgc cag caa agg       336
Ser Arg Met Glu Ala Glu Asp Ala Ala Thr Tyr Tyr Cys Gln Gln Arg
            100                 105                 110 agt tct tac cca ccc acg ttc ggt gct ggg acc aag ctg gag ctg aaa       384
Ser Ser Tyr Pro Pro Thr Phe Gly Ala Gly Thr Lys Leu Glu Leu Lys
        115                 120                 125
```

```
<210> SEQ ID NO 45
<211> LENGTH: 16
<212> TYPE: PRT
<213> ORGANISM: Mus musculus

<400> SEQUENCE: 45

Tyr Ile Gly Tyr Thr Gly Arg Thr Asn Tyr Ser Pro Ser Leu Lys Ser
 1               5                  10                  15

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
aaggaaaaaa gcggccgcac atcgctctca ctggaggctg                              40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
cgatgggccc ttggtggagg ctgaggagac ggtgactgag                              40

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
ccggaattca cttatgagaa tagcagtaat tagctaggga cc                           42

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
agccaccgta cgtttcagct ccagcttggt cccagcaccg aac                          43

<210> SEQ ID NO 50
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Description of Artificial Sequence: Synthetic
      DNA

<400> SEQUENCE: 50 atg aga gtg ctg att ctt ttg tgg ctg ttc aca gcc ttt cct ggt atc         48
Met Arg Val Leu Ile Leu Leu Trp Leu Phe Thr Ala Phe Pro Gly Ile
 1               5                  10                  15 ctg tct cag gtg cag ctg cag gag tcg ggt cca gga ctg gtg aag cct         96
```

```
Leu Ser Gln Val Gln Leu Gln Glu Ser Gly Pro Gly Leu Val Lys Pro
            20                  25                  30 tcg cag acc ctg tcc ctc acc tgc act gtc tct ggt ggc tcc atc agc      144
Ser Gln Thr Leu Ser Leu Thr Cys Thr Val Ser Gly Gly Ser Ile Ser
        35                  40                  45 act gaa tat gcc tgg aac tgg atc agg cag ccc cca ggg aag ggc ctg      192
Thr Glu Tyr Ala Trp Asn Trp Ile Arg Gln Pro Pro Gly Lys Gly Leu
    50                  55                  60 gag tgg att ggg tat ata ggc tac act ggt aga act aac tac gca cca      240
Glu Trp Ile Gly Tyr Ile Gly Tyr Thr Gly Arg Thr Asn Tyr Ala Pro
 65                  70                  75                  80 tct ctc aaa agt cga ata acc ata tca gta gac acg tcc aag aac cag      288
Ser Leu Lys Ser Arg Ile Thr Ile Ser Val Asp Thr Ser Lys Asn Gln
                 85                  90                  95 ttc tcc ctg cag ctg agc tct gtg acc gcc gag gac acg gct acg tat      336
Phe Ser Leu Gln Leu Ser Ser Val Thr Ala Glu Asp Thr Ala Thr Tyr
            100                 105                 110 tac tgt gcg aga atg gac tac tgg ggc caa ggg acc ctg gtc acc gtc      384
Tyr Cys Ala Arg Met Asp Tyr Trp Gly Gln Gly Thr Leu Val Thr Val
        115                 120                 125 tcc tca                                                              390
Ser Ser
    130

<210> SEQ ID NO 51
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Description of Artificial Sequence: Synthetic
      DNA

<400> SEQUENCE: 51 atg aga gtg ctg att ctt ttg tgg ctg ttc aca gcc ttt cct ggt atc       48
Met Arg Val Leu Ile Leu Leu Trp Leu Phe Thr Ala Phe Pro Gly Ile
  1               5                  10                  15 ctg tct cag gtg cag ctg cag gag tcg ggt cca gga ctg gtg aag cct       96
Leu Ser Gln Val Gln Leu Gln Glu Ser Gly Pro Gly Leu Val Lys Pro
            20                  25                  30 tcg cag acc ctg tcc ctc acc tgc act gtc tct ggt ttc tcc atc acc      144
Ser Gln Thr Leu Ser Leu Thr Cys Thr Val Ser Gly Phe Ser Ile Thr
        35                  40                  45 act gaa tat gcc tgg aac tgg atc agg cag ttt cca ggg aac aga ctg      192
Thr Glu Tyr Ala Trp Asn Trp Ile Arg Gln Phe Pro Gly Asn Arg Leu
    50                  55                  60 gag tgg atg ggg tat ata ggc tac act ggt aga act aac tac gca cca      240
Glu Trp Met Gly Tyr Ile Gly Tyr Thr Gly Arg Thr Asn Tyr Ala Pro
 65                  70                  75                  80 tct ctc aaa agt cga ata acc ata tca cga gac acg tcc aag aac cag      288
Ser Leu Lys Ser Arg Ile Thr Ile Ser Arg Asp Thr Ser Lys Asn Gln
                 85                  90                  95 ttc tcc ctg cag ctg agc tct gtg acc gcc gag gac acg gct acg tat      336
Phe Ser Leu Gln Leu Ser Ser Val Thr Ala Glu Asp Thr Ala Thr Tyr
            100                 105                 110 tac tgt aca aga atg gac tac tgg ggc caa ggg acc ctg gtc acc gtc      384
Tyr Cys Thr Arg Met Asp Tyr Trp Gly Gln Gly Thr Leu Val Thr Val
        115                 120                 125 tcc tca                                                              390
Ser Ser
    130
```

<210> SEQ ID NO 52
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Description of Artificial Sequence: Synthetic DNA

<400> SEQUENCE: 52

```
atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
 1               5                  10                  15 ctg tct cag gtg cag ctg cag gag tcg ggt cca gga ctg gtg aag cct      96
Leu Ser Gln Val Gln Leu Gln Glu Ser Gly Pro Gly Leu Val Lys Pro
             20                  25                  30 tcg cag acc ctg tcc ctc acc tgc act gtc tct ggt ttc tcc atc agc     144
Ser Gln Thr Leu Ser Leu Thr Cys Thr Val Ser Gly Phe Ser Ile Ser
         35                  40                  45 act gaa tat gcc tgg aac tgg atc agg cag ttt cca ggg aag ggc ctg     192
Thr Glu Tyr Ala Trp Asn Trp Ile Arg Gln Phe Pro Gly Lys Gly Leu
     50                  55                  60 gag tgg att ggg tat ata ggc tac act ggt aga act aac tac gca cca     240
Glu Trp Ile Gly Tyr Ile Gly Tyr Thr Gly Arg Thr Asn Tyr Ala Pro
 65                  70                  75                  80 tct ctc aaa agt cga ata acc ata tca gta gac acg tcc aag aac cag     288
Ser Leu Lys Ser Arg Ile Thr Ile Ser Val Asp Thr Ser Lys Asn Gln
                 85                  90                  95 ttc tcc ctg cag ctg agc tct gtg acc gcc gag gac acg gct acg tat     336
Phe Ser Leu Gln Leu Ser Ser Val Thr Ala Glu Asp Thr Ala Thr Tyr
            100                 105                 110 tac tgt aca aga atg gac tac tgg ggc caa ggg acc ctg gtc acc gtc     384
Tyr Cys Thr Arg Met Asp Tyr Trp Gly Gln Gly Thr Leu Val Thr Val
        115                 120                 125 tcc tca                                                              390
Ser Ser
    130
```

<210> SEQ ID NO 53
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Description of Artificial Sequence: Synthetic DNA

<400> SEQUENCE: 53

```
atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
 1               5                  10                  15 ctg tct cag gtg cag ctg cag gag tcg ggt cca gga ctg gtg aag cct      96
Leu Ser Gln Val Gln Leu Gln Glu Ser Gly Pro Gly Leu Val Lys Pro
             20                  25                  30 tcg cag acc ctg tcc ctc acc tgc act gtc tct ggt ttc tcc atc agc     144
Ser Gln Thr Leu Ser Leu Thr Cys Thr Val Ser Gly Phe Ser Ile Ser
         35                  40                  45 act gaa tat gcc tgg aac tgg atc agg cag ttt cca ggg aag ggc ctg     192
Thr Glu Tyr Ala Trp Asn Trp Ile Arg Gln Phe Pro Gly Lys Gly Leu
     50                  55                  60 gag tgg att ggg tat ata ggc tac act ggt aga act aac tac gca cca     240
Glu Trp Ile Gly Tyr Ile Gly Tyr Thr Gly Arg Thr Asn Tyr Ala Pro
```

```
tct ctc aaa agt cga ata acc ata tca cga gac acg tcc aag aac cag      288
Ser Leu Lys Ser Arg Ile Thr Ile Ser Arg Asp Thr Ser Lys Asn Gln
                85                  90                  95 ttc tcc ctg cag ctg agc tct gtg acc gcc gag gac acg gct acg tat      336
Phe Ser Leu Gln Leu Ser Ser Val Thr Ala Glu Asp Thr Ala Thr Tyr
            100                 105                 110 tac tgt aca aga atg gac tac tgg ggc caa ggg acc ctg gtc acc gtc      384
Tyr Cys Thr Arg Met Asp Tyr Trp Gly Gln Gly Thr Leu Val Thr Val
        115                 120                 125 tcc tca                                                              390
Ser Ser
    130

<210> SEQ ID NO 54
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Description of Artificial Sequence: Synthetic
      DNA

<400> SEQUENCE: 54 atg aga gtg ctg att ctt ttg tgg ctg ttc aca gcc ttt cct ggt atc       48
Met Arg Val Leu Ile Leu Leu Trp Leu Phe Thr Ala Phe Pro Gly Ile
 1               5                  10                  15 ctg tct cag gtg cag ctg cag gag tcg ggt cca gga ctg gtg aag cct       96
Leu Ser Gln Val Gln Leu Gln Glu Ser Gly Pro Gly Leu Val Lys Pro
            20                  25                  30 tcg cag acc ctg tcc ctc acc tgc act gtc tct ggt ttc tcc atc acc      144
Ser Gln Thr Leu Ser Leu Thr Cys Thr Val Ser Gly Phe Ser Ile Thr
        35                  40                  45 act gaa tat gcc tgg aac tgg atc agg cag ttt cca ggg aag ggc ctg      192
Thr Glu Tyr Ala Trp Asn Trp Ile Arg Gln Phe Pro Gly Lys Gly Leu
    50                  55                  60 gag tgg att ggg tat ata ggc tac act ggt aga act aac tac gca cca      240
Glu Trp Ile Gly Tyr Ile Gly Tyr Thr Gly Arg Thr Asn Tyr Ala Pro
 65                  70                  75                  80 tct ctc aaa agt cga ata acc ata tca gta gac acg tcc aag aac cag      288
Ser Leu Lys Ser Arg Ile Thr Ile Ser Val Asp Thr Ser Lys Asn Gln
                85                  90                  95 ttc tcc ctg cag ctg agc tct gtg acc gcc gag gac acg gct acg tat      336
Phe Ser Leu Gln Leu Ser Ser Val Thr Ala Glu Asp Thr Ala Thr Tyr
            100                 105                 110 tac tgt aca aga atg gac tac tgg ggc caa ggg acc ctg gtc acc gtc      384
Tyr Cys Thr Arg Met Asp Tyr Trp Gly Gln Gly Thr Leu Val Thr Val
        115                 120                 125 tcc tca                                                              390
Ser Ser
    130

<210> SEQ ID NO 55
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Description of Artificial Sequence: Synthetic
      DNA

<400> SEQUENCE: 55
```

```
atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
 1               5                  10                  15 ctg tct cag gtg cag ctg cag gag tcg ggt cca gga ctg gtg aag cct      96
Leu Ser Gln Val Gln Leu Gln Glu Ser Gly Pro Gly Leu Val Lys Pro
             20                  25                  30 tcg cag acc ctg tcc ctc acc tgc act gtc tct ggt ttc tcc atc acc     144
Ser Gln Thr Leu Ser Leu Thr Cys Thr Val Ser Gly Phe Ser Ile Thr
         35                  40                  45 act gaa tat gcc tgg aac tgg atc agg cag ccc cca ggg aag ggc ctg     192
Thr Glu Tyr Ala Trp Asn Trp Ile Arg Gln Pro Pro Gly Lys Gly Leu
 50                  55                  60 gag tgg atg ggg tat ata ggc tac act ggt aga act aac tac gca cca     240
Glu Trp Met Gly Tyr Ile Gly Tyr Thr Gly Arg Thr Asn Tyr Ala Pro
 65                  70                  75                  80 tct ctc aaa agt cga ata acc ata tca cga gac acg tcc aag aac cag     288
Ser Leu Lys Ser Arg Ile Thr Ile Ser Arg Asp Thr Ser Lys Asn Gln
             85                  90                  95 ttc tcc ctg cag ctg agc tct gtg acc gcc gag gac acg gct acg tat     336
Phe Ser Leu Gln Leu Ser Ser Val Thr Ala Glu Asp Thr Ala Thr Tyr
            100                 105                 110 tac tgt aca aga atg gac tac tgg ggc caa ggg acc ctg gtc acc gtc     384
Tyr Cys Thr Arg Met Asp Tyr Trp Gly Gln Gly Thr Leu Val Thr Val
        115                 120                 125 tcc tca                                                             390
Ser Ser
    130

<210> SEQ ID NO 56
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Description of Artificial Sequence: Synthetic
      DNA

<400> SEQUENCE: 56 atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
 1               5                  10                  15 ctg tct cag gtg cag ctg cag gag tcg ggt cca gga ctg gtg aag cct      96
Leu Ser Gln Val Gln Leu Gln Glu Ser Gly Pro Gly Leu Val Lys Pro
             20                  25                  30 tcg cag acc ctg tcc ctc acc tgc act gtc tct ggt ttc tcc atc agc     144
Ser Gln Thr Leu Ser Leu Thr Cys Thr Val Ser Gly Phe Ser Ile Ser
         35                  40                  45 act gaa tat gcc tgg aac tgg atc agg cag ttt cca ggg aag ggc ctg     192
Thr Glu Tyr Ala Trp Asn Trp Ile Arg Gln Phe Pro Gly Lys Gly Leu
 50                  55                  60 gag tgg atg ggg tat ata ggc tac act ggt aga act aac tac gca cca     240
Glu Trp Met Gly Tyr Ile Gly Tyr Thr Gly Arg Thr Asn Tyr Ala Pro
 65                  70                  75                  80 tct ctc aaa agt cga ata acc ata tca cga gac acg tcc aag aac cag     288
Ser Leu Lys Ser Arg Ile Thr Ile Ser Arg Asp Thr Ser Lys Asn Gln
             85                  90                  95 ttc tcc ctg cag ctg agc tct gtg acc gcc gag gac acg gct acg tat     336
Phe Ser Leu Gln Leu Ser Ser Val Thr Ala Glu Asp Thr Ala Thr Tyr
            100                 105                 110 tac tgt aca aga atg gac tac tgg ggc caa ggg acc ctg gtc acc gtc     384
Tyr Cys Thr Arg Met Asp Tyr Trp Gly Gln Gly Thr Leu Val Thr Val
        115                 120                 125
```

```
tcc tca                                                              390
Ser Ser
    130

<210> SEQ ID NO 57
<211> LENGTH: 384
<212> TYPE: DNA
<213> ORGANISM: Artificial sequence
<220> FEATURE:
<221> NAME/KEY: CDS
<222> LOCATION: (1)..(384)
<223> OTHER INFORMATION: Description of Artificial Sequence: Synthetic
      DNA

<400> SEQUENCE: 57 atg cat ttt caa gtg cag att ttc agc ttc ctg cta atc agt gcc tca    48
Met His Phe Gln Val Gln Ile Phe Ser Phe Leu Leu Ile Ser Ala Ser
  1               5                  10                  15 gtc ata atg tcc aga gga gac atc cag atg acc cag tct cca tcc tcc    96
Val Ile Met Ser Arg Gly Asp Ile Gln Met Thr Gln Ser Pro Ser Ser
             20                  25                  30 ctg tct gca tct gta gga gac aga gtc acc atc act tgt agt gcc agt   144
Leu Ser Ala Ser Val Gly Asp Arg Val Thr Ile Thr Cys Ser Ala Ser
         35                  40                  45 tca agt gta agt tac atg cac tgg tat cag cag aaa cca ggg aaa gcc   192
Ser Ser Val Ser Tyr Met His Trp Tyr Gln Gln Lys Pro Gly Lys Ala
     50                  55                  60 cct aag ctc ctg atc tat agc aca tcc aac ctg gct tct ggg gtc cca   240
Pro Lys Leu Leu Ile Tyr Ser Thr Ser Asn Leu Ala Ser Gly Val Pro
 65                  70                  75                  80 tca agg ttc agt ggc agt gga tct ggg aca gat ttc act ctc acc atc   288
Ser Arg Phe Ser Gly Ser Gly Ser Gly Thr Asp Phe Thr Leu Thr Ile
                 85                  90                  95 agc agc ctg cag cct gaa gat ttt gca act tat tac tgt cag caa agg   336
Ser Ser Leu Gln Pro Glu Asp Phe Ala Thr Tyr Tyr Cys Gln Gln Arg
            100                 105                 110 agt tct tac cca ccc acg ttc ggc caa ggg acc aag gta gag atc aaa   384
Ser Ser Tyr Pro Pro Thr Phe Gly Gln Gly Thr Lys Val Glu Ile Lys
        115                 120                 125

<210> SEQ ID NO 58
<211> LENGTH: 384
<212> TYPE: DNA
<213> ORGANISM: Artificial sequence
<220> FEATURE:
<221> NAME/KEY: CDS
<222> LOCATION: (1)..(384)
<223> OTHER INFORMATION: Description of Artificial Sequence: Synthetic
      DNA

<400> SEQUENCE: 58 atg cat ttt caa gtg cag att ttc agc ttc ctg cta atc agt gcc tca    48
Met His Phe Gln Val Gln Ile Phe Ser Phe Leu Leu Ile Ser Ala Ser
  1               5                  10                  15 gtc ata atg tcc aga gga gac atc gtt atg ata cag tct cca tcc tcc    96
Val Ile Met Ser Arg Gly Asp Ile Val Met Ile Gln Ser Pro Ser Ser
             20                  25                  30 ctg tct gca tct gta gga gac aga gtc acc atc act tgt agt gcc agt   144
Leu Ser Ala Ser Val Gly Asp Arg Val Thr Ile Thr Cys Ser Ala Ser
         35                  40                  45 tca agt gta agt tac atg cac tgg ttc cag cag aaa cca ggg aaa tct   192
Ser Ser Val Ser Tyr Met His Trp Phe Gln Gln Lys Pro Gly Lys Ser
     50                  55                  60 cct aag ctc tgg atc tat agc aca tcc aac ctg gct tct ggg gtc cca   240
```

```
Pro Lys Leu Trp Ile Tyr Ser Thr Ser Asn Leu Ala Ser Gly Val Pro
 65                  70                  75                  80 tca agg ttc agt ggc agt gga tct ggg aca gat tac act ctc acc atc      288
Ser Arg Phe Ser Gly Ser Gly Ser Gly Thr Asp Tyr Thr Leu Thr Ile
                 85                  90                  95 agc agc atg cag cct gaa gat ttt gca act tat tac tgt cag caa agg      336
Ser Ser Met Gln Pro Glu Asp Phe Ala Thr Tyr Tyr Cys Gln Gln Arg
            100                 105                 110 agt tct tac cca ccc acg ttc ggc caa ggg acc aag gta gag atc aaa      384
Ser Ser Tyr Pro Pro Thr Phe Gly Gln Gly Thr Lys Val Glu Ile Lys
        115                 120                 125

<210> SEQ ID NO 59
<211> LENGTH: 384
<212> TYPE: DNA
<213> ORGANISM: Artificial sequence
<220> FEATURE:
<221> NAME/KEY: CDS
<222> LOCATION: (1)..(384)
<223> OTHER INFORMATION: Description of Artificial Sequence: Synthetic
      DNA

<400> SEQUENCE: 59 atg cat ttt caa gtg cag att ttc agc ttc ctg cta atc agt gcc tca       48
Met His Phe Gln Val Gln Ile Phe Ser Phe Leu Leu Ile Ser Ala Ser
  1               5                  10                  15 gtc ata atg tcc aga gga gac atc cag atg acc cag tct cca tcc tcc       96
Val Ile Met Ser Arg Gly Asp Ile Gln Met Thr Gln Ser Pro Ser Ser
             20                  25                  30 ctg tct gca tct gta gga gac aga gtc acc atc act tgt agt gcc agt      144
Leu Ser Ala Ser Val Gly Asp Arg Val Thr Ile Thr Cys Ser Ala Ser
         35                  40                  45 tca agt gta agt tac atg cac tgg tat cag cag aaa cca ggg aaa gcc      192
Ser Ser Val Ser Tyr Met His Trp Tyr Gln Gln Lys Pro Gly Lys Ala
     50                  55                  60 cct aag ctc tgg atc tat agc aca tcc aac ctg gct tct ggg gtc cca      240
Pro Lys Leu Trp Ile Tyr Ser Thr Ser Asn Leu Ala Ser Gly Val Pro
 65                  70                  75                  80 tca agg ttc agt ggc agt gga tct ggg aca gat tac act ctc acc atc      288
Ser Arg Phe Ser Gly Ser Gly Ser Gly Thr Asp Tyr Thr Leu Thr Ile
                 85                  90                  95 agc agc ctg cag cct gaa gat ttt gca act tat tac tgt cag caa agg      336
Ser Ser Leu Gln Pro Glu Asp Phe Ala Thr Tyr Tyr Cys Gln Gln Arg
            100                 105                 110 agt tct tac cca ccc acg ttc ggc caa ggg acc aag gta gag atc aaa      384
Ser Ser Tyr Pro Pro Thr Phe Gly Gln Gly Thr Lys Val Glu Ile Lys
        115                 120                 125

<210> SEQ ID NO 60
<211> LENGTH: 384
<212> TYPE: DNA
<213> ORGANISM: Artificial sequence
<220> FEATURE:
<221> NAME/KEY: CDS
<222> LOCATION: (1)..(384)
<223> OTHER INFORMATION: Description of Artificial Sequence: Synthetic
      DNA

<400> SEQUENCE: 60 atg cat ttt caa gtg cag att ttc agc ttc ctg cta atc agt gcc tca       48
Met His Phe Gln Val Gln Ile Phe Ser Phe Leu Leu Ile Ser Ala Ser
  1               5                  10                  15 gtc ata atg tcc aga gga gac atc cag atg acc cag tct cca tcc tcc       96
Val Ile Met Ser Arg Gly Asp Ile Gln Met Thr Gln Ser Pro Ser Ser
             20                  25                  30
```

```
ctg tct gca tct gta gga gac aga gtc acc atc act tgt agt gcc agt    144
Leu Ser Ala Ser Val Gly Asp Arg Val Thr Ile Thr Cys Ser Ala Ser
        35                  40                  45 tca agt gta agt tac atg cac tgg tat cag cag aaa cca ggg aaa gcc    192
Ser Ser Val Ser Tyr Met His Trp Tyr Gln Gln Lys Pro Gly Lys Ala
 50                  55                  60 cct aag ctc tgg atc tat agc aca tcc aac ctg gct tct ggg gtc cca    240
Pro Lys Leu Trp Ile Tyr Ser Thr Ser Asn Leu Ala Ser Gly Val Pro
 65                  70                  75                  80 tca agg ttc agt ggc agt gga tct ggg aca gat tac act ctc acc atc    288
Ser Arg Phe Ser Gly Ser Gly Ser Gly Thr Asp Tyr Thr Leu Thr Ile
                 85                  90                  95 agc agc atg cag cct gaa gat ttt gca act tat tac tgt cag caa agg    336
Ser Ser Met Gln Pro Glu Asp Phe Ala Thr Tyr Tyr Cys Gln Gln Arg
            100                 105                 110 agt tct tac cca ccc acg ttc ggc caa ggg acc aag gta gag atc aaa    384
Ser Ser Tyr Pro Pro Thr Phe Gly Gln Gly Thr Lys Val Glu Ile Lys
                115                 120                 125

<210> SEQ ID NO 61
<211> LENGTH: 384
<212> TYPE: DNA
<213> ORGANISM: Artificial sequence
<220> FEATURE:
<221> NAME/KEY: CDS
<222> LOCATION: (1)..(384)
<223> OTHER INFORMATION: Description of Artificial Sequence: Synthetic
      DNA

<400> SEQUENCE: 61 atg cat ttt caa gtg cag att ttc agc ttc ctg cta atc agt gcc tca     48
Met His Phe Gln Val Gln Ile Phe Ser Phe Leu Leu Ile Ser Ala Ser
 1               5                  10                  15 gtc ata atg tcc aga gga gac atc cag atg acc cag tct cca tcc tcc     96
Val Ile Met Ser Arg Gly Asp Ile Gln Met Thr Gln Ser Pro Ser Ser
             20                  25                  30 ctg tct gca tct gta gga gac aga gtc acc atc act tgt agt gcc agt    144
Leu Ser Ala Ser Val Gly Asp Arg Val Thr Ile Thr Cys Ser Ala Ser
        35                  40                  45 tca agt gta agt tac atg cac tgg tat cag cag aaa cca ggg aaa tct    192
Ser Ser Val Ser Tyr Met His Trp Tyr Gln Gln Lys Pro Gly Lys Ser
 50                  55                  60 cct aag ctc tgg atc tat agc aca tcc aac ctg gct tct ggg gtc cca    240
Pro Lys Leu Trp Ile Tyr Ser Thr Ser Asn Leu Ala Ser Gly Val Pro
 65                  70                  75                  80 tca agg ttc agt ggc agt gga tct ggg aca gat tac act ctc acc atc    288
Ser Arg Phe Ser Gly Ser Gly Ser Gly Thr Asp Tyr Thr Leu Thr Ile
                 85                  90                  95 agc agc ctg cag cct gaa gat ttt gca act tat tac tgt cag caa agg    336
Ser Ser Leu Gln Pro Glu Asp Phe Ala Thr Tyr Tyr Cys Gln Gln Arg
            100                 105                 110 agt tct tac cca ccc acg ttc ggc caa ggg acc aag gta gag atc aaa    384
Ser Ser Tyr Pro Pro Thr Phe Gly Gln Gly Thr Lys Val Glu Ile Lys
                115                 120                 125

<210> SEQ ID NO 62
<211> LENGTH: 384
<212> TYPE: DNA
<213> ORGANISM: Artificial sequence
<220> FEATURE:
<221> NAME/KEY: CDS
<222> LOCATION: (1)..(384)
<223> OTHER INFORMATION: Description of Artificial Sequence: Synthetic
      DNA
```

<400> SEQUENCE: 62

| | | | | | | | | | | | | | | | | |
|---|---|---|---|---|---|---|---|---|---|---|---|---|---|---|---|---|
| atg | cat | ttt | caa | gtg | cag | att | ttc | agc | ttc | ctg | cta | atc | agt | gcc | tca | 48 |
| Met | His | Phe | Gln | Val | Gln | Ile | Phe | Ser | Phe | Leu | Leu | Ile | Ser | Ala | Ser | |
| 1 | | | | 5 | | | | | 10 | | | | | 15 | | |

| gtc | ata | atg | tcc | aga | gga | gac | atc | cag | atg | acc | cag | tct | cca | tcc | tcc | 96 |
|---|---|---|---|---|---|---|---|---|---|---|---|---|---|---|---|---|
| Val | Ile | Met | Ser | Arg | Gly | Asp | Ile | Gln | Met | Thr | Gln | Ser | Pro | Ser | Ser | |
| | | | 20 | | | | | 25 | | | | | 30 | | | |

| ctg | tct | gca | tct | gta | gga | gac | aga | gtc | acc | atc | act | tgt | agt | gcc | agt | 144 |
|---|---|---|---|---|---|---|---|---|---|---|---|---|---|---|---|---|
| Leu | Ser | Ala | Ser | Val | Gly | Asp | Arg | Val | Thr | Ile | Thr | Cys | Ser | Ala | Ser | |
| | | | 35 | | | | | 40 | | | | | 45 | | | |

| tca | agt | gta | agt | tac | atg | cac | tgg | ttc | cag | cag | aaa | cca | ggg | aaa | gcc | 192 |
|---|---|---|---|---|---|---|---|---|---|---|---|---|---|---|---|---|
| Ser | Ser | Val | Ser | Tyr | Met | His | Trp | Phe | Gln | Gln | Lys | Pro | Gly | Lys | Ala | |
| | 50 | | | | | 55 | | | | | 60 | | | | | |

| cct | aag | ctc | tgg | atc | tat | agc | aca | tcc | aac | ctg | gct | tct | ggg | gtc | cca | 240 |
|---|---|---|---|---|---|---|---|---|---|---|---|---|---|---|---|---|
| Pro | Lys | Leu | Trp | Ile | Tyr | Ser | Thr | Ser | Asn | Leu | Ala | Ser | Gly | Val | Pro | |
| 65 | | | | | 70 | | | | | 75 | | | | | 80 | |

| tca | agg | ttc | agt | ggc | agt | gga | tct | ggg | aca | gat | tac | act | ctc | acc | atc | 288 |
|---|---|---|---|---|---|---|---|---|---|---|---|---|---|---|---|---|
| Ser | Arg | Phe | Ser | Gly | Ser | Gly | Ser | Gly | Thr | Asp | Tyr | Thr | Leu | Thr | Ile | |
| | | | | 85 | | | | | 90 | | | | | 95 | | |

| agc | agc | atg | cag | cct | gaa | gat | ttt | gca | act | tat | tac | tgt | cag | caa | agg | 336 |
|---|---|---|---|---|---|---|---|---|---|---|---|---|---|---|---|---|
| Ser | Ser | Met | Gln | Pro | Glu | Asp | Phe | Ala | Thr | Tyr | Tyr | Cys | Gln | Gln | Arg | |
| | | | 100 | | | | | 105 | | | | | 110 | | | |

| agt | tct | tac | cca | ccc | acg | ttc | ggc | caa | ggg | acc | aag | gta | gag | atc | aaa | 384 |
|---|---|---|---|---|---|---|---|---|---|---|---|---|---|---|---|---|
| Ser | Ser | Tyr | Pro | Pro | Thr | Phe | Gly | Gln | Gly | Thr | Lys | Val | Glu | Ile | Lys | |
| | | 115 | | | | | 120 | | | | | 125 | | | | |

<210> SEQ ID NO 63
<211> LENGTH: 384
<212> TYPE: DNA
<213> ORGANISM: Artificial sequence
<220> FEATURE:
<221> NAME/KEY: CDS
<222> LOCATION: (1)..(384)
<223> OTHER INFORMATION: Description of Artificial Sequence: Synthetic DNA

<400> SEQUENCE: 63

| atg | cat | ttt | caa | gtg | cag | att | ttc | agc | ttc | ctg | cta | atc | agt | gcc | tca | 48 |
|---|---|---|---|---|---|---|---|---|---|---|---|---|---|---|---|---|
| Met | His | Phe | Gln | Val | Gln | Ile | Phe | Ser | Phe | Leu | Leu | Ile | Ser | Ala | Ser | |
| 1 | | | | 5 | | | | | 10 | | | | | 15 | | |

| gtc | ata | atg | tcc | aga | gga | gac | atc | cag | atg | acc | cag | tct | cca | tcc | tcc | 96 |
|---|---|---|---|---|---|---|---|---|---|---|---|---|---|---|---|---|
| Val | Ile | Met | Ser | Arg | Gly | Asp | Ile | Gln | Met | Thr | Gln | Ser | Pro | Ser | Ser | |
| | | | 20 | | | | | 25 | | | | | 30 | | | |

| ctg | tct | gca | tct | gta | gga | gac | aga | gtc | acc | atc | act | tgt | agt | gcc | agt | 144 |
|---|---|---|---|---|---|---|---|---|---|---|---|---|---|---|---|---|
| Leu | Ser | Ala | Ser | Val | Gly | Asp | Arg | Val | Thr | Ile | Thr | Cys | Ser | Ala | Ser | |
| | | | 35 | | | | | 40 | | | | | 45 | | | |

| tca | agt | gta | agt | tac | atg | cac | tgg | tat | cag | cag | aaa | cca | ggg | aaa | tct | 192 |
|---|---|---|---|---|---|---|---|---|---|---|---|---|---|---|---|---|
| Ser | Ser | Val | Ser | Tyr | Met | His | Trp | Tyr | Gln | Gln | Lys | Pro | Gly | Lys | Ser | |
| | 50 | | | | | 55 | | | | | 60 | | | | | |

| cct | aag | ctc | tgg | atc | tat | agc | aca | tcc | aac | ctg | gct | tct | ggg | gtc | cca | 240 |
|---|---|---|---|---|---|---|---|---|---|---|---|---|---|---|---|---|
| Pro | Lys | Leu | Trp | Ile | Tyr | Ser | Thr | Ser | Asn | Leu | Ala | Ser | Gly | Val | Pro | |
| 65 | | | | | 70 | | | | | 75 | | | | | 80 | |

| tca | agg | ttc | agt | ggc | agt | gga | tct | ggg | aca | tct | tac | tca | ctc | acc | atc | 288 |
|---|---|---|---|---|---|---|---|---|---|---|---|---|---|---|---|---|
| Ser | Arg | Phe | Ser | Gly | Ser | Gly | Ser | Gly | Thr | Ser | Tyr | Ser | Leu | Thr | Ile | |
| | | | | 85 | | | | | 90 | | | | | 95 | | |

| agc | agc | ctg | cag | cct | gaa | gat | ttt | gca | act | tat | tac | tgt | cag | caa | agg | 336 |
|---|---|---|---|---|---|---|---|---|---|---|---|---|---|---|---|---|
| Ser | Ser | Leu | Gln | Pro | Glu | Asp | Phe | Ala | Thr | Tyr | Tyr | Cys | Gln | Gln | Arg | |
| | | | 100 | | | | | 105 | | | | | 110 | | | |

| agt | tct | tac | cca | ccc | acg | ttc | ggc | caa | ggg | acc | aag | gta | gag | atc | aaa | 384 |
|---|---|---|---|---|---|---|---|---|---|---|---|---|---|---|---|---|
| Ser | Ser | Tyr | Pro | Pro | Thr | Phe | Gly | Gln | Gly | Thr | Lys | Val | Glu | Ile | Lys | |
| | | 115 | | | | | 120 | | | | | 125 | | | | |

<210> SEQ ID NO 64
<211> LENGTH: 133
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
aaggcttcac cagtcctgga cccgactcct gcagctgcac ctgagacagg ataccaggaa     60
aggctgtgaa cagccacaaa agaatcagca ctctcatggt gaggggtcgc ggccgcactg    120
gccgtcgttt tac                                                       133

<210> SEQ ID NO 65
<211> LENGTH: 126
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 65
ccaggactgg tgaagccttc gcagaccctg tccctcacct gcactgtctc tggtggctcc     60
atcagcactg aatatgcctg gaactggatc aggcagcccc cagggaaggg cctggagtgg    120
attggg                                                               126

<210> SEQ ID NO 66
<211> LENGTH: 135
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
tcggcggtca cagagctcag ctgcagggag aactggttct tggacgtgtc tactgatatg     60
gttattcgac ttttgagaga tggtgcgtag ttagttctac cagtgtagcc tatataccca    120
atccactcca ggccc                                                     135

<210> SEQ ID NO 67
<211> LENGTH: 122
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 67
gagctctgtg accgccgagg acacggctac gtattactgt gcgagaatgg actactgggg     60
ccaagggacc ctggtcaccg tctcctcagc ctccaccaag ggcccgtcat agctgtttcc    120
tg                                                                   122

<210> SEQ ID NO 68
<211> LENGTH: 126
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
ccaggactgg tgaagccttc gcagaccctg tccctcacct gcactgtctc tggtttctcc     60

```
atcaccactg aatatgcctg gaactggatc aggcagtttc cagggaacag actggagtgg    120
atgggg                                                                126

<210> SEQ ID NO 69
<211> LENGTH: 135
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
tcggcggtca cagagctcag ctgcagggag aactggttct tggacgtgtc tcgtgatatg    60
gttattcgac ttttgagaga tggtgcgtag ttagttctac cagtgtagcc tatataccc    120 atccactcca gtctg                                                      135

<210> SEQ ID NO 70
<211> LENGTH: 123
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
tgagctctgt gaccgccgag gacacggcta cgtattactg tacaagaatg gactactggg    60
gccaagggac cctggtcacc gtctcctcag cctccaccaa gggcccgtca tagctgtttc    120
ctg                                                                   123

<210> SEQ ID NO 71
<211> LENGTH: 123
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
ggagactggg tcatctggat gtctcctctg gacattatga ctgaggcact gattagcagg    60
aagctgaaaa tctgcacttg aaaatgcatt ttgaggaggc gaattcactg gccgtcgttt    120
tac                                                                   123

<210> SEQ ID NO 72
<211> LENGTH: 125
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
tccagatgac ccagtctcca tcctccctgt ctgcatctgt aggagacaga gtcaccatca    60
cttgtagtgc cagttcaagt gtaagttaca tgcactggta tcagcagaaa ccagggaaag    120
ccccct                                                                125

<210> SEQ ID NO 73
<211> LENGTH: 122
<212> TYPE: DNA
<213> ORGANISM: Artificial Sequence
<220> FEATURE:
<223> OTHER INFORMATION: Description of Artificial Sequence: Synthetic
```

DNA

<400> SEQUENCE: 73
gcaggctgct gatggtgaga gtgaaatctg tcccagatcc actgccactg aaccttgatg     60
ggaccccaga agccaggttg gatgtgctat agatcaggag cttaggggct ttccctggtt    120
tc                                                                   122

<210> SEQ ID NO 74
<211> LENGTH: 128
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
ctcaccatca gcagcctgca gcctgaagat tttgcaactt attactgtca gcaaggagt      60 tcttacccac ccacgttcgg ccaagggacc aaggtagaga tcaaacgtac ggtcatagct    120
gtttcctg                                                             128

<210> SEQ ID NO 75
<211> LENGTH: 123
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
ggagactgta tcataacgat gtctcctctg gacattatga ctgaggcact gattagcagg     60
aagctgaaaa tctgcacttg aaaatgcatt ttgaggaggc gaattcactg gccgtcgttt    120
tac                                                                  123

<210> SEQ ID NO 76
<211> LENGTH: 125
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
tcgttatgat acagtctcca tcctccctgt ctgcatctgt aggagacaga gtcaccatca     60
cttgtagtgc cagttcaagt gtaagttaca tgcactggtt ccagcagaaa ccagggaaat    120
ctcct                                                                125

<210> SEQ ID NO 77
<211> LENGTH: 122
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
gcatgctgct gatggtgaga gtgtaatctg tcccagatcc actgccactg aaccttgatg     60
ggaccccaga agccaggttg gatgtgctat agatccagag cttaggagat ttccctggtt    120
tc                                                                   122

<210> SEQ ID NO 78

```
<211> LENGTH: 128
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 78
ctcaccatca gcagcatgca gcctgaagat tttgcaactt attactgtca gcaaaggagt      60
tcttacccac ccacgttcgg ccaagggacc aaggtagaga tcaaacgtac ggtcatagct     120
gtttcctg                                                              128

<210> SEQ ID NO 79
<211> LENGTH: 126
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 79
ccaggactgg tgaagccttc gcagaccctg tccctcacct gcactgtctc tggtttctcc      60
atcagcactg aatatgcctg gaactggatc aggcagtttc cagggaaggg cctggagtgg     120
attggg                                                                126

<210> SEQ ID NO 80
<211> LENGTH: 135
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 80
tcggcggtca cagagctcag ctgcagggag aactggttct ggacgtgtc tcgtgatatg       60 gttattcgac ttttgagaga tggtgcgtag ttagttctac cagtgtagcc tatataccca     120
atccactcca ggccc                                                      135

<210> SEQ ID NO 81
<211> LENGTH: 122
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 81
gcaggctgct gatggtgaga gtgtaatctg tcccagatcc actgccactg aaccttgatg      60
ggaccccaga agccaggttg gatgtgctat agatccagag cttagggct ttccctggtt     120 tc                                                                    122

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 82
ctgggacatc ttactcactc acca                                             24
```

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 83
tggtgagtga gtaagatgtc ccag                                          24

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 84
gttccaggca tattcagtgg tgatgg                                        26

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 85
actgaatatg cctggaactg g                                             21

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 86
ctaccagtgt agcctatata ccccatccac                                    30

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 87
tatataggct acactggtag aac                                           23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 88
gttctaccag tgtagcctat ata                                           23

<210> SEQ ID NO 89
<211> LENGTH: 30

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 89
caagtgtaag ttacatgcac tggttccagc                                       30

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 90
agtgcatgta acttacactt g                                                21

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 91
gatcaggcag cccccaggga agggcc                                           26

<210> SEQ ID NO 92
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 92
ggcccttccc tgggggctgc ctgatc                                           26

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 93
agcacatcca acctggcttc t                                                21

<210> SEQ ID NO 94
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 94
agccaggttg gatgtgctat agatccagag cttaggagat ttc                        43

<210> SEQ ID NO 95
<211> LENGTH: 21
<212> TYPE: DNA
<213> ORGANISM: Artificial Sequence
```

-continued

<220> FEATURE:
<223> OTHER INFORMATION: Description of Artificial Sequence: Synthetic
      DNA

<400> SEQUENCE: 95
agaagccagg ttggatgtgc t                                            21

<210> SEQ ID NO 96
<211> LENGTH: 657
<212> TYPE: DNA
<213> ORGANISM: Artificial sequence
<220> FEATURE:
<221> NAME/KEY: CDS
<222> LOCATION: (1)..(657)
<223> OTHER INFORMATION: Description of Artificial Sequence: Synthetic
      DNA

<400> SEQUENCE: 96

```
atg atc cgc tgc ggc ctg gcc tgc gag cgc tgc cgc tgg atc ctg ccc        48
Met Ile Arg Cys Gly Leu Ala Cys Glu Arg Cys Arg Trp Ile Leu Pro
 1               5                   10                  15 ctg ctc cta ctc agc gcc atc gcc ttc gac atc atc gcg ctg gcc ggc        96
Leu Leu Leu Leu Ser Ala Ile Ala Phe Asp Ile Ile Ala Leu Ala Gly
             20                  25                  30 cgc ggc tgg ttg cag tct agc aac cac atc cag acg tcc tcg ctg tgg       144
Arg Gly Trp Leu Gln Ser Ser Asn His Ile Gln Thr Ser Ser Leu Trp
         35                  40                  45 tgg agg tgc ttc gac gag ggc ggc ggc agc ggg tcc tac gac gat ggc       192
Trp Arg Cys Phe Asp Glu Gly Gly Gly Ser Gly Ser Tyr Asp Asp Gly
     50                  55                  60 tgt cag agc ctc atg gag tac gcg tgg ggt aga gca gcg gct gcc atg       240
Cys Gln Ser Leu Met Glu Tyr Ala Trp Gly Arg Ala Ala Ala Ala Met
 65                  70                  75                  80 ctc ttc tgt ggc ttc atc atc ctg gtg atc tgt ttc atc ctc tcc ttc       288
Leu Phe Cys Gly Phe Ile Ile Leu Val Ile Cys Phe Ile Leu Ser Phe
                 85                  90                  95 ttc gcc ctc tgt gga ccc cag atg ctt gtc ttc ctg aga gtg att gga       336
Phe Ala Leu Cys Gly Pro Gln Met Leu Val Phe Leu Arg Val Ile Gly
            100                 105                 110 ggt ctc ctt gcc ttg gct gct gtg ttc cag atc atc tcc ctg gta att       384
Gly Leu Leu Ala Leu Ala Ala Val Phe Gln Ile Ile Ser Leu Val Ile
        115                 120                 125 tac ccc gtg aag tac acc cag acc ttc acc ctt cat gcc aac cct gct       432
Tyr Pro Val Lys Tyr Thr Gln Thr Phe Thr Leu His Ala Asn Pro Ala
    130                 135                 140 gtc act tac atc tat aac tgg gcc tac ggc ttt ggg tgg gca gcc acg       480
Val Thr Tyr Ile Tyr Asn Trp Ala Tyr Gly Phe Gly Trp Ala Ala Thr
145                 150                 155                 160 att atc ctg att ggc tgt gcc ttc ttc ttc tgc tgc ctc ccc aac tac       528
Ile Ile Leu Ile Gly Cys Ala Phe Phe Phe Cys Cys Leu Pro Asn Tyr
                165                 170                 175 gaa gat gac ctt ctg ggc aat gcc aag ccc agg tac ttc tac aca tct       576
Glu Asp Asp Leu Leu Gly Asn Ala Lys Pro Arg Tyr Phe Tyr Thr Ser
            180                 185                 190 gcc caa gct tac gta gaa caa aaa ctc atc tca gaa gag gat ctg aat       624
Ala Gln Ala Tyr Val Glu Gln Lys Leu Ile Ser Glu Glu Asp Leu Asn
        195                 200                 205 agc gcc gtc gac cat cat cat cat cat cat tga                           657
Ser Ala Val Asp His His His His His His ***
    210                 215
```

<210> SEQ ID NO 97
<211> LENGTH: 657

<212> TYPE: DNA
<213> ORGANISM: Artificial sequence
<220> FEATURE:
<221> NAME/KEY: CDS
<222> LOCATION: (1)..(657)
<223> OTHER INFORMATION: Description of Artificial Sequence: Synthetic
      DNA

<400> SEQUENCE: 97

```
atg atc cgc tgc ggc ctg gcc tgc gag cgc tgc cgc tgg atc ctg ccc      48
Met Ile Arg Cys Gly Leu Ala Cys Glu Arg Cys Arg Trp Ile Leu Pro
1               5                   10                  15 ctg ctc cta ctc agc gcc atc gcc ttc gac atc atc gcg ctg gcc ggc      96
Leu Leu Leu Leu Ser Ala Ile Ala Phe Asp Ile Ile Ala Leu Ala Gly
            20                  25                  30 cgc ggc tgg ttg cag tct agc gac cac ggc cag acg tcc tcg ctg tgg     144
Arg Gly Trp Leu Gln Ser Ser Asp His Gly Gln Thr Ser Ser Leu Trp
        35                  40                  45 tgg aaa tgc tcc caa gag ggc ggc ggc agc ggg tcc tac gag gag ggc     192
Trp Lys Cys Ser Gln Glu Gly Gly Gly Ser Gly Ser Tyr Glu Glu Gly
    50                  55                  60 tgt cag agc ctc atg gag tac gcg tgg ggt aga gca gcg gct gcc atg     240
Cys Gln Ser Leu Met Glu Tyr Ala Trp Gly Arg Ala Ala Ala Ala Met
65                  70                  75                  80 ctc ttc tgt ggc ttc atc atc ctg gtg atc tgt ttc atc ctc tcc ttc     288
Leu Phe Cys Gly Phe Ile Ile Leu Val Ile Cys Phe Ile Leu Ser Phe
                85                  90                  95 ttc gcc ctc tgt gga ccc cag atg ctt gtc ttc ctg aga gtg att gga     336
Phe Ala Leu Cys Gly Pro Gln Met Leu Val Phe Leu Arg Val Ile Gly
            100                 105                 110 ggt ctc ctt gcc ttg gct gct gtg ttc cag atc atc tcc ctg gta att     384
Gly Leu Leu Ala Leu Ala Ala Val Phe Gln Ile Ile Ser Leu Val Ile
        115                 120                 125 tac ccc gtg aag tac acc cag acc ttc agg ctt cat gat aac cct gct     432
Tyr Pro Val Lys Tyr Thr Gln Thr Phe Arg Leu His Asp Asn Pro Ala
    130                 135                 140 gtc aat tac atc tat aac tgg gcc tac ggc ttt ggg tgg gca gcc acg     480
Val Asn Tyr Ile Tyr Asn Trp Ala Tyr Gly Phe Gly Trp Ala Ala Thr
145                 150                 155                 160 att atc ctg att ggc tgt gcc ttc ttc ttc tgc tgc ctc ccc aac tac     528
Ile Ile Leu Ile Gly Cys Ala Phe Phe Phe Cys Cys Leu Pro Asn Tyr
                165                 170                 175 gaa gat gac ctt ctg ggc aat gcc aag ccc agg tac ttc tac aca tct     576
Glu Asp Asp Leu Leu Gly Asn Ala Lys Pro Arg Tyr Phe Tyr Thr Ser
            180                 185                 190 gcc caa gct tac gta gaa caa aaa ctc atc tca gaa gag gat ctg aat     624
Ala Gln Ala Tyr Val Glu Gln Lys Leu Ile Ser Glu Glu Asp Leu Asn
        195                 200                 205 agc gcc gtc gac cat cat cat cat cat cat tga                         657
Ser Ala Val Asp His His His His His His ***
    210                 215
```

<210> SEQ ID NO 98
<211> LENGTH: 657
<212> TYPE: DNA
<213> ORGANISM: Artificial sequence
<220> FEATURE:
<221> NAME/KEY: CDS
<222> LOCATION: (1)..(657)
<223> OTHER INFORMATION: Description of Artificial Sequence: Synthetic
      DNA

<400> SEQUENCE: 98

```
atg atc cgc tgc ggc ctg gcc tgc gag cgc tgc cgc tgg atc ctg ccc      48
```

```
                Met Ile Arg Cys Gly Leu Ala Cys Glu Arg Cys Arg Trp Ile Leu Pro
                 1               5                  10                  15 ctg ctc cta ctc agc gcc atc gcc ttc gac atc atc gcg ctg gcc ggc         96
Leu Leu Leu Leu Ser Ala Ile Ala Phe Asp Ile Ile Ala Leu Ala Gly
             20                  25                  30 cgc ggc tgg ttg cag tct agc aac cac atc cag acg tcc tcg ctg tgg        144
Arg Gly Trp Leu Gln Ser Ser Asn His Ile Gln Thr Ser Ser Leu Trp
         35                  40                  45 tgg agg tgc ttc gac gag ggc ggc agc ggg tcc tac gac gat ggc            192
Trp Arg Cys Phe Asp Glu Gly Gly Ser Gly Ser Tyr Asp Asp Gly
     50                  55                  60 tgt cag agc ctc atg gag tac gcg tgg ggt aga gca gcg gct gcc atg        240
Cys Gln Ser Leu Met Glu Tyr Ala Trp Gly Arg Ala Ala Ala Ala Met
 65                  70                  75                  80 ctc ttc tgt gga ttc atc atc ctg gtg atc tgt ttc atc ctc tcc ttc        288
Leu Phe Cys Gly Phe Ile Ile Leu Val Ile Cys Phe Ile Leu Ser Phe
                 85                  90                  95 ttc gcc ctc tgt gga ccc cag atg ctt gtc ttc ctg aga gtg att gga        336
Phe Ala Leu Cys Gly Pro Gln Met Leu Val Phe Leu Arg Val Ile Gly
            100                 105                 110 ggt ctc ctt gcc ttg gct gct gtg ttc cag atc atc tcc ctg gta att        384
Gly Leu Leu Ala Leu Ala Ala Val Phe Gln Ile Ile Ser Leu Val Ile
        115                 120                 125 tac ccc gtg aag tac acc cag acc ttc agg ctt cat gat aac cct gct        432
Tyr Pro Val Lys Tyr Thr Gln Thr Phe Arg Leu His Asp Asn Pro Ala
    130                 135                 140 gtc aat tac atc tat aac tgg gcc tac ggc ttt ggg tgg gca gcc acg        480
Val Asn Tyr Ile Tyr Asn Trp Ala Tyr Gly Phe Gly Trp Ala Ala Thr
145                 150                 155                 160 att atc ctg att ggc tgt gcc ttc ttc ttc tgc tgc ctc ccc aac tac        528
Ile Ile Leu Ile Gly Cys Ala Phe Phe Phe Cys Cys Leu Pro Asn Tyr
                165                 170                 175 gaa gat gac ctt ctg ggc aat gcc aag ccc agg tac ttc tac aca tct        576
Glu Asp Asp Leu Leu Gly Asn Ala Lys Pro Arg Tyr Phe Tyr Thr Ser
            180                 185                 190 gcc caa gct tac gta gaa caa aaa ctc atc tca gaa gag gat ctg aat        624
Ala Gln Ala Tyr Val Glu Gln Lys Leu Ile Ser Glu Glu Asp Leu Asn
        195                 200                 205 agc gcc gtc gac cat cat cat cat cat cat tga                            657
Ser Ala Val Asp His His His His His His ***
    210                 215

<210> SEQ ID NO 99
<211> LENGTH: 657
<212> TYPE: DNA
<213> ORGANISM: Artificial sequence
<220> FEATURE:
<221> NAME/KEY: CDS
<222> LOCATION: (1)..(657)
<223> OTHER INFORMATION: Description of Artificial Sequence: Synthetic
      DNA

<400> SEQUENCE: 99 atg atc cgc tgc ggc ctg gcc tgc gag cgc tgc cgc tgg atc ctg ccc         48
Met Ile Arg Cys Gly Leu Ala Cys Glu Arg Cys Arg Trp Ile Leu Pro
 1               5                  10                  15 ctg ctc cta ctc agc gcc atc gcc ttc gac atc atc gcg ctg gcc ggc         96
Leu Leu Leu Leu Ser Ala Ile Ala Phe Asp Ile Ile Ala Leu Ala Gly
             20                  25                  30 cgc ggc tgg ttg cag tct agc aac cac atc cag acg tcc tcg ctg tgg        144
Arg Gly Trp Leu Gln Ser Ser Asn His Ile Gln Thr Ser Ser Leu Trp
         35                  40                  45
```

```
tgg aaa tgc tcc caa gag ggc ggc ggc agc ggg tcc tac gag gag ggc    192
Trp Lys Cys Ser Gln Glu Gly Gly Gly Ser Gly Ser Tyr Glu Glu Gly
     50                  55                  60 tgt cag agc ctc atg gag tac gcg tgg ggt aga gca gcg gct gcc atg    240
Cys Gln Ser Leu Met Glu Tyr Ala Trp Gly Arg Ala Ala Ala Ala Met
 65                  70                  75                  80 ctc ttc tgt ggc ttc atc atc ctg gtg atc tgt ttc atc ctc tcc ttc    288
Leu Phe Cys Gly Phe Ile Ile Leu Val Ile Cys Phe Ile Leu Ser Phe
                 85                  90                  95 ttc gcc ctc tgt gga ccc cag atg ctt gtc ttc ctg aga gtg att gga    336
Phe Ala Leu Cys Gly Pro Gln Met Leu Val Phe Leu Arg Val Ile Gly
                100                 105                 110 ggt ctc ctt gcc ttg gct gct gtg ttc cag atc atc tcc ctg gta att    384
Gly Leu Leu Ala Leu Ala Ala Val Phe Gln Ile Ile Ser Leu Val Ile
        115                 120                 125 tac ccc gtg aag tac acc cag acc ttc acc ctt cat gcc aac cct gct    432
Tyr Pro Val Lys Tyr Thr Gln Thr Phe Thr Leu His Ala Asn Pro Ala
130                 135                 140 gtc act tac atc tat aac tgg gcc tac ggc ttt ggg tgg gca gcc acg    480
Val Thr Tyr Ile Tyr Asn Trp Ala Tyr Gly Phe Gly Trp Ala Ala Thr
145                 150                 155                 160 att atc ctg att ggc tgt gcc ttc ttc ttc tgc tgc ctc ccc aac tac    528
Ile Ile Leu Ile Gly Cys Ala Phe Phe Phe Cys Cys Leu Pro Asn Tyr
                165                 170                 175 gaa gat gac ctt ctg ggc aat gcc aag ccc agg tac ttc tac aca tct    576
Glu Asp Asp Leu Leu Gly Asn Ala Lys Pro Arg Tyr Phe Tyr Thr Ser
                180                 185                 190 gcc caa gct tac gta gaa caa aaa ctc atc tca gaa gag gat ctg aat    624
Ala Gln Ala Tyr Val Glu Gln Lys Leu Ile Ser Glu Glu Asp Leu Asn
        195                 200                 205 agc gcc gtc gac cat cat cat cat cat cat tga                        657
Ser Ala Val Asp His His His His His His ***
    210                 215

<210> SEQ ID NO 100
<211> LENGTH: 657
<212> TYPE: DNA
<213> ORGANISM: Artificial sequence
<220> FEATURE:
<221> NAME/KEY: CDS
<222> LOCATION: (1)..(657)
<223> OTHER INFORMATION: Description of Artificial Sequence: Synthetic
      DNA

<400> SEQUENCE: 100 atg atc cgc tgc ggc ctg gcc tgc gag cgc tgc cgc tgg atc ctg ccc     48
Met Ile Arg Cys Gly Leu Ala Cys Glu Arg Cys Arg Trp Ile Leu Pro
  1               5                  10                  15 ctg ctc cta ctc agc gcc atc gcc ttc gac atc atc gcg ctg gcc ggc     96
Leu Leu Leu Leu Ser Ala Ile Ala Phe Asp Ile Ile Ala Leu Ala Gly
             20                  25                  30 cgc ggc tgg ttg cag tct agc gac cac ggc cag acg tcc tcg ctg tgg    144
Arg Gly Trp Leu Gln Ser Ser Asp His Gly Gln Thr Ser Ser Leu Trp
         35                  40                  45 tgg agg tgc ttc gac gag ggc ggc ggc agc ggg tcc tac gag gag ggc    192
Trp Arg Cys Phe Asp Glu Gly Gly Gly Ser Gly Ser Tyr Glu Glu Gly
     50                  55                  60 tgt cag agc ctc atg gag tac gcg tgg ggt aga gca gcg gct gcc atg    240
Cys Gln Ser Leu Met Glu Tyr Ala Trp Gly Arg Ala Ala Ala Ala Met
 65                  70                  75                  80 ctc ttc tgt ggc ttc atc atc ctg gtg atc tgt ttc atc ctc tcc ttc    288
Leu Phe Cys Gly Phe Ile Ile Leu Val Ile Cys Phe Ile Leu Ser Phe
                 85                  90                  95
```

```
ttc gcc ctc tgt gga ccc cag atg ctt gtc ttc ctg aga gtg att gga      336
Phe Ala Leu Cys Gly Pro Gln Met Leu Val Phe Leu Arg Val Ile Gly
            100                 105                 110 ggt ctc ctt gcc ttg gct gct gtg ttc cag atc atc tcc ctg gta att      384
Gly Leu Leu Ala Leu Ala Ala Val Phe Gln Ile Ile Ser Leu Val Ile
        115                 120                 125 tac ccc gtg aag tac acc cag acc ttc acc ctt cat gcc aac cct gct      432
Tyr Pro Val Lys Tyr Thr Gln Thr Phe Thr Leu His Ala Asn Pro Ala
    130                 135                 140 gtc act tac atc tat aac tgg gcc tac ggc ttt ggg tgg gca gcc acg      480
Val Thr Tyr Ile Tyr Asn Trp Ala Tyr Gly Phe Gly Trp Ala Ala Thr
145                 150                 155                 160 att atc ctg att ggc tgt gcc ttc ttc ttc tgc tgc ctc ccc aac tac      528
Ile Ile Leu Ile Gly Cys Ala Phe Phe Phe Cys Cys Leu Pro Asn Tyr
                165                 170                 175 gaa gat gac ctt ctg ggc aat gcc aag ccc agg tac ttc tac aca tct      576
Glu Asp Asp Leu Leu Gly Asn Ala Lys Pro Arg Tyr Phe Tyr Thr Ser
            180                 185                 190 gcc caa gct tac gta gaa caa aaa ctc atc tca gaa gag gat ctg aat      624
Ala Gln Ala Tyr Val Glu Gln Lys Leu Ile Ser Glu Glu Asp Leu Asn
        195                 200                 205 agc gcc gtc gac cat cat cat cat cat cat tga                          657
Ser Ala Val Asp His His His His His His ***
    210                 215

<210> SEQ ID NO 101
<211> LENGTH: 657
<212> TYPE: DNA
<213> ORGANISM: Artificial sequence
<220> FEATURE:
<221> NAME/KEY: CDS
<222> LOCATION: (1)..(657)
<223> OTHER INFORMATION: Description of Artificial Sequence: Synthetic
      DNA

<400> SEQUENCE: 101 atg atc cgc tgc ggc ctg gcc tgc gag cgc tgc cgc tgg atc ctg ccc       48
Met Ile Arg Cys Gly Leu Ala Cys Glu Arg Cys Arg Trp Ile Leu Pro
1               5                   10                  15 ctg ctc cta ctc agc gcc atc gcc ttc gac atc atc gcg ctg gcc ggc       96
Leu Leu Leu Leu Ser Ala Ile Ala Phe Asp Ile Ile Ala Leu Ala Gly
            20                  25                  30 cgc ggc tgg ttg cag tct agc gac cac ggc cag acg tcc tcg ctg tgg      144
Arg Gly Trp Leu Gln Ser Ser Asp His Gly Gln Thr Ser Ser Leu Trp
        35                  40                  45 tgg aaa tgc tcc caa gag ggc ggc ggc agc ggg tcc tac gac gat ggc      192
Trp Lys Cys Ser Gln Glu Gly Gly Gly Ser Gly Ser Tyr Asp Asp Gly
    50                  55                  60 tgt cag agc ctc atg gag tac gcg tgg ggt aga gca gcg gct gcc atg      240
Cys Gln Ser Leu Met Glu Tyr Ala Trp Gly Arg Ala Ala Ala Ala Met
65                  70                  75                  80 ctc ttc tgt ggc ttc atc atc ctg gtg atc tgt ttc atc ctc tcc ttc      288
Leu Phe Cys Gly Phe Ile Ile Leu Val Ile Cys Phe Ile Leu Ser Phe
                85                  90                  95 ttc gcc ctc tgt gga ccc cag atg ctt gtc ttc ctg aga gtg att gga      336
Phe Ala Leu Cys Gly Pro Gln Met Leu Val Phe Leu Arg Val Ile Gly
            100                 105                 110 ggt ctc ctt gcc ttg gct gct gtg ttc cag atc atc tcc ctg gta att      384
Gly Leu Leu Ala Leu Ala Ala Val Phe Gln Ile Ile Ser Leu Val Ile
        115                 120                 125 tac ccc gtg aag tac acc cag acc ttc acc ctt cat gcc aac cct gct      432
Tyr Pro Val Lys Tyr Thr Gln Thr Phe Thr Leu His Ala Asn Pro Ala
```

```
                130                 135                 140
gtc act tac atc tat aac tgg gcc tac ggc ttt ggg tgg gca gcc acg      480
Val Thr Tyr Ile Tyr Asn Trp Ala Tyr Gly Phe Gly Trp Ala Ala Thr
145                 150                 155                 160 att atc ctg att ggc tgt gcc ttc ttc ttc tgc tgc ctc ccc aac tac      528
Ile Ile Leu Ile Gly Cys Ala Phe Phe Phe Cys Cys Leu Pro Asn Tyr
                165                 170                 175 gaa gat gac ctt ctg ggc aat gcc aag ccc agg tac ttc tac aca tct      576
Glu Asp Asp Leu Leu Gly Asn Ala Lys Pro Arg Tyr Phe Tyr Thr Ser
            180                 185                 190 gcc caa gct tac gta gaa caa aaa ctc atc tca gaa gag gat ctg aat      624
Ala Gln Ala Tyr Val Glu Gln Lys Leu Ile Ser Glu Glu Asp Leu Asn
        195                 200                 205 agc gcc gtc gac cat cat cat cat cat cat tga                          657
Ser Ala Val Asp His His His His His His ***
    210                 215

<210> SEQ ID NO 102
<211> LENGTH: 86
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 102
gtctagcaac cacatccaga cgtcctcgct gtggtggagg tgcttcgacg agggcggcgg      60
cagcgggtcc tacgacgatg gctgtc                                          86

<210> SEQ ID NO 103
<211> LENGTH: 86
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 103
gacagccatc gtcgtaggac ccgctgccgc cgccctcgtc gaagcacctc caccacagcg      60
aggacgtctg gatgtggttg ctagac                                          86

<210> SEQ ID NO 104
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 104
gaccttcagg cttcatgata accctgctgt caattacatc                            40

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 105
gatgtaattg acagcagggt tatcatgaag cctgaaggtc                            40

<210> SEQ ID NO 106
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 106
gtctagcaac cacatccaga cg                                              22

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 107
cgtctggatg tggttgctag ac                                              22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 108
ggtggaggtg cttcgacgag gg                                              22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 109
ccctcgtcga agcacctcca cc                                              22

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 110
cctacgacga tggctgtc                                                   18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 111
gacagccatc gtcgtagg                                                   18

<210> SEQ ID NO 112
<211> LENGTH: 20
<212> TYPE: DNA
```

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 112
taatacgact cactataggg                                              20

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 113
tagaaggcac agtcgagg                                                18

<210> SEQ ID NO 114
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 114
ccggaattcg ccaccatgat ccgctgcggc ctg                                33

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 115
gggttcgaac ggcagatgtg tagaagta                                      28

<210> SEQ ID NO 116
<211> LENGTH: 582
<212> TYPE: DNA
<213> ORGANISM: Macaca fascicularis
<220> FEATURE:
<221> NAME/KEY: CDS
<222> LOCATION: (1)..(582)

<400> SEQUENCE: 116

```
atg atc cgc tgc ggc ctg gcc tgc gag cgc tgc cgc tgg atc ctg ccc        48
Met Ile Arg Cys Gly Leu Ala Cys Glu Arg Cys Arg Trp Ile Leu Pro
 1               5                  10                  15 ctg ctc cta ctc agc gcc atc gcc ttc gac atc atc gcg ctg gcc ggc        96
Leu Leu Leu Leu Ser Ala Ile Ala Phe Asp Ile Ile Ala Leu Ala Gly
             20                  25                  30 cgc ggc tgg ttg cag tcg agc gac cac atc cag acg tcc tcg ctg tgg       144
Arg Gly Trp Leu Gln Ser Ser Asp His Ile Gln Thr Ser Ser Leu Trp
         35                  40                  45 tgg aaa tgt tcc caa gag ggt ggc ggc agc ggg tcc tac gag gag ggc       192
Trp Lys Cys Ser Gln Glu Gly Gly Gly Ser Gly Ser Tyr Glu Glu Gly
     50                  55                  60 tgt cag agc ctc atg gag tac gca tgg ggt aga gca gcg gct gcc atg       240
Cys Gln Ser Leu Met Glu Tyr Ala Trp Gly Arg Ala Ala Ala Ala Met
 65                  70                  75                  80 ctc ttc tgt ggc ttc atc atc ctg gtg atc tgt ttc atc ctc tcc ttc       288
```

| | |
|---|---|
| Leu Phe Cys Gly Phe Ile Ile Leu Val Ile Cys Phe Ile Leu Ser Phe<br>                      85                      90                    95 | |
| ttc gcc ctc tgt gga ccc cag atg ctt gtc ttc cta aga gtg att gga<br>Phe Ala Leu Cys Gly Pro Gln Met Leu Val Phe Leu Arg Val Ile Gly<br>                  100                    105                    110 | 336 |
| ggt ctc ctt gcc ttg gct gct gtg ttc cag atc atc tcc ctg gta att<br>Gly Leu Leu Ala Leu Ala Ala Val Phe Gln Ile Ile Ser Leu Val Ile<br>        115                    120                    125 | 384 |
| tac ccc gtg aag tac acc cag acc ttc gcc ctt cat gcc aac ccc gct<br>Tyr Pro Val Lys Tyr Thr Gln Thr Phe Ala Leu His Ala Asn Pro Ala<br>              130                    135                    140 | 432 |
| gtc act tac atc tat aac tgg gcc tac ggc ttt ggc tgg gca gcc acg<br>Val Thr Tyr Ile Tyr Asn Trp Ala Tyr Gly Phe Gly Trp Ala Ala Thr<br>145                      150                    155                    160 | 480 |
| att atc ctg att ggc tgt gcc ttc ttc tgc tgc ctc ccc aac tac<br>Ile Ile Leu Ile Gly Cys Ala Phe Phe Cys Cys Leu Pro Asn Tyr<br>                  165                    170                    175 | 528 |
| gaa gat gac ctt ctg ggt aat gcc aag ccc agg tac ttc tac aca tct<br>Glu Asp Asp Leu Leu Gly Asn Ala Lys Pro Arg Tyr Phe Tyr Thr Ser<br>              180                    185                    190 | 576 |
| gcc taa<br>Ala *** | 582 |

```
<210> SEQ ID NO 117
<211> LENGTH: 657
<212> TYPE: DNA
<213> ORGANISM: Artificial sequence
<220> FEATURE:
<221> NAME/KEY: CDS
<222> LOCATION: (1)..(657)
<223> OTHER INFORMATION: Description of Artificial Sequence: Synthetic
      DNA

<400> SEQUENCE: 117
```

| | |
|---|---|
| atg atc cgc tgc ggc ctg gcc tgc gag cgc tgc cgc tgg atc ctg ccc<br>Met Ile Arg Cys Gly Leu Ala Cys Glu Arg Cys Arg Trp Ile Leu Pro<br>1                    5                      10                    15 | 48 |
| ctg ctc cta ctc agc gcc atc gcc ttc gac atc atc gcg ctg gcc ggc<br>Leu Leu Leu Leu Ser Ala Ile Ala Phe Asp Ile Ile Ala Leu Ala Gly<br>                20                    25                    30 | 96 |
| cgc ggc tgg ttg cag tcg agc gac cac atc cag acg tcc tcg ctg tgg<br>Arg Gly Trp Leu Gln Ser Ser Asp His Ile Gln Thr Ser Ser Leu Trp<br>        35                    40                    45 | 144 |
| tgg aaa tgt tcc caa gag ggt ggc ggc agc ggg tcc tac gag gag ggc<br>Trp Lys Cys Ser Gln Glu Gly Gly Gly Ser Gly Ser Tyr Glu Glu Gly<br>50                      55                    60 | 192 |
| tgt cag agc ctc atg gag tac gca tgg ggt aga gca gcg gct gcc atg<br>Cys Gln Ser Leu Met Glu Tyr Ala Trp Gly Arg Ala Ala Ala Ala Met<br>65                      70                    75                    80 | 240 |
| ctc ttc tgt ggc ttc atc atc ctg gtg atc tgt ttc atc ctc tcc ttc<br>Leu Phe Cys Gly Phe Ile Ile Leu Val Ile Cys Phe Ile Leu Ser Phe<br>                  85                      90                    95 | 288 |
| ttc gcc ctc tgt gga ccc cag atg ctt gtc ttc cta aga gtg att gga<br>Phe Ala Leu Cys Gly Pro Gln Met Leu Val Phe Leu Arg Val Ile Gly<br>                100                    105                    110 | 336 |
| ggt ctc ctt gcc ttg gct gct gtg ttc cag atc atc tcc ctg gta att<br>Gly Leu Leu Ala Leu Ala Ala Val Phe Gln Ile Ile Ser Leu Val Ile<br>        115                    120                    125 | 384 |
| tac ccc gtg aag tac acc cag acc ttc gcc ctt cat gcc aac ccc gct<br>Tyr Pro Val Lys Tyr Thr Gln Thr Phe Ala Leu His Ala Asn Pro Ala<br>              130                    135                    140 | 432 |
| gtc act tac atc tat aac tgg gcc tac ggc ttt ggc tgg gca gcc acg | 480 |

-continued

| | | | | | | | | | | | | | | | | |
|---|---|---|---|---|---|---|---|---|---|---|---|---|---|---|---|---|
| Val | Thr | Tyr | Ile | Tyr | Asn | Trp | Ala | Tyr | Gly | Phe | Gly | Trp | Ala | Ala | Thr | |
| 145 | | | | 150 | | | | | 155 | | | | | 160 | | |

| att | atc | ctg | att | ggc | tgt | gcc | ttc | ttc | ttc | tgc | tgc | ctc | ccc | aac | tac | 528 |
|---|---|---|---|---|---|---|---|---|---|---|---|---|---|---|---|---|
| Ile | Ile | Leu | Ile | Gly | Cys | Ala | Phe | Phe | Phe | Cys | Cys | Leu | Pro | Asn | Tyr | |
| | | | | 165 | | | | | 170 | | | | | 175 | | |

| gaa | gat | gac | ctt | ctg | ggt | aat | gcc | aag | ccc | agg | tac | ttc | tac | aca | tct | 576 |
|---|---|---|---|---|---|---|---|---|---|---|---|---|---|---|---|---|
| Glu | Asp | Asp | Leu | Leu | Gly | Asn | Ala | Lys | Pro | Arg | Tyr | Phe | Tyr | Thr | Ser | |
| | | | 180 | | | | | 185 | | | | | 190 | | | |

| gcc | caa | gct | tac | gta | gaa | caa | aaa | ctc | atc | tca | gaa | gag | gat | ctg | aat | 624 |
|---|---|---|---|---|---|---|---|---|---|---|---|---|---|---|---|---|
| Ala | Gln | Ala | Tyr | Val | Glu | Gln | Lys | Leu | Ile | Ser | Glu | Glu | Asp | Leu | Asn | |
| | | 195 | | | | | 200 | | | | | 205 | | | | |

| agc | gcc | gtc | gac | cat | cat | cat | cat | cat | tga | | | | | | | 657 |
|---|---|---|---|---|---|---|---|---|---|---|---|---|---|---|---|---|
| Ser | Ala | Val | Asp | His | His | His | His | His | *** | | | | | | | |
| 210 | | | | | 215 | | | | | | | | | | | |